(12) United States Patent
Ackermann et al.

(10) Patent No.: US 8,399,676 B2
(45) Date of Patent: *Mar. 19, 2013

(54) PIPERIDINE DERIVATIVES

(75) Inventors: Jean Ackermann, Riehen (CH); Aurelia Conte, Basel (CH); Daniel Hunziker, Moehlin (CH); Werner Neidhart, Hagenthal-le-Bas (FR); Matthias Nettekoven, Grenzach-Wyhlen (DE); Stanley Wertheimer, Croton, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 238 days.

This patent is subject to a terminal disclaimer.

(21) Appl. No.: 12/842,062

(22) Filed: Jul. 23, 2010

(65) Prior Publication Data

US 2011/0028515 A1 Feb. 3, 2011

(30) Foreign Application Priority Data

Jul. 30, 2009 (EP) .................................. 09166846

(51) Int. Cl.
*C07D 211/58* (2006.01)
*A61K 31/4468* (2006.01)
(52) U.S. Cl. ........ 546/223; 546/194; 546/205; 514/318; 514/319; 514/329
(58) Field of Classification Search .................. 546/194, 546/205, 223; 514/318, 319, 329
See application file for complete search history.

(56) References Cited

FOREIGN PATENT DOCUMENTS

EP 0121972 10/1984
WO 2008/110008 9/2008

OTHER PUBLICATIONS

International Search Report for PCT/EP2010/060854 dated Nov. 11, 2010.
Wang et al., Chemistry & Biology vol. 13 pp. 1019-1027 (2006).
Gregoire et al., Physiol. Rev. vol. 78 pp. 783-809 (1998).
Unger, R. H. Annu. Rev. Med. vol. 53 pp. 319-336 (2002).
Duncan et al., Annu. Rev. Nutr. vol. 27 pp. 79-101 (2007).
Jaworski et al., Am. J. Physiol. Gastrointest. Liver Physiol. vol. 293 pp. G1-G4 (2007).
Large et al., J. Lipid. Res. vol. 39 pp. 1688-1695 (1998).

*Primary Examiner* — David K O Dell
(74) *Attorney, Agent, or Firm* — George W. Johnston; Patricia S. Rocha-Tramaloni; Gene J. Yao

(57) ABSTRACT

Compounds of formula (I)

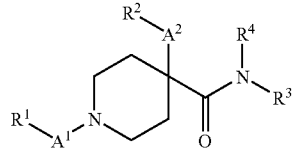

as well as pharmaceutically acceptable salts thereof can be used in the form of pharmaceutical compositions, wherein $A^1, A^2, R^1, R^2, R^3$ and $R^4$ have the significance given in claim 1.

16 Claims, No Drawings

PIPERIDINE DERIVATIVES

PRIORITY TO RELATED APPLICATION(S)

This application claims the benefit of European Patent Application No. 09166846.7, filed Jul. 30, 2009, which is hereby incorporated by reference in its entirety.

FIELD OF THE INVENTION

The present invention is concerned with novel piperidine derivatives useful as HSL inhibitors.

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess (Wang M. et al., Chem. Biol., 2006, 13, 1019-10271; Gregoire F. M. et al., Physiol. Rev., 1998, 78, 783-809). However, unlike TAG synthesis that also occurs at high levels in liver for very low density lipoprotein (VLDL) production, lipolysis for the provision of fatty acids as an energy source for use by other organs is unique to adipocytes. The release of free fatty acids (FFA) from TAG proceeds in an orderly and regulated manner (Unger R. H, Annu. Rev. Med. 2002, 53, 319-336; Duncan R. E. et al, 2007, Annu Rev Nutr, 27, 79-101; Jaworski K. Et al, 2007, Am J Physiol Gastrointest Liver Physiol, 293, G1-4), stimulated by catecholamines and regulated by hormones such as insulin, glucagon and epinephrine.

The most important enzyme in WAT believed responsible for hormone regulated hydrolysis of triglyceride is hormone sensitive lipase (HSL). This enzyme is also present in the liver, skeletal muscle, pancreas and adrenal glands. In the basal state, it has minimal activity against its substrate. Stimulation of adipocytes by hormones activates protein kinase A resulting in the phosphorylation of HSL and the lipid droplet coating protein perilipin. Phosphorylation of perilipin leads to its removal from the lipid droplet and migration of phosphorylated HSL from the cytosol to the lipid droplet where it catalyzes the hydrolysis of triglycerides (Wang M. et al., Chem. Biol., 2006, 13, 1019-10271).

Dysregulation of adipocyte lipolysis, resulting in elevated circulating non-esterified fatty acids (NEFA) is associated with obesity and co-morbidities including the development of type 2 diabetes (Unger R. H, Annu. Rev. Med. 2002, 53, 319-336). Obese or insulin resistant subjects have increased visceral adipose tissue depots. These depots contain elevated levels of HSL protein (Large, V. et al., 1998, J. Lipid. Res. 39, 1688-1695) and exhibit enhanced lipolytic activity as they are resistant to the insulin-mediated suppression of lipolysis. This results in increased plasma levels of free fatty acids, which further exacerbates insulin resistance due to the accumulation of triglycerides in tissues other than WAT such as liver, pancreas and muscle. The ectopic deposition of triglycerides results in pathological effects such as increased glucose production in the liver, decreased insulin secretion from the pancreas, and reduced glucose uptake and fatty acid oxidation in skeletal muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

SUMMARY OF THE INVENTION

The present invention relates to a compound according to formula (I),

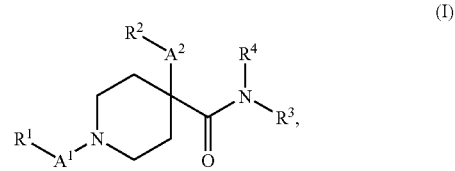

wherein $R^1$ is selected from the group consisting of: alkyl, cycloalkyl, cycloalkyalkyl, haloalkyl, thiophenyl, substituted thiophenyl, phenyl, substituted phenyl, benzyloxy, substituted benzyloxy, pyridinyl, substituted pyridinyl, pyrimidyl and substituted pyrimidyl, wherein substituted thiophenyl, substituted phenyl, substituted benzyloxy, substituted pyridinyl and substituted pyrimidyl are substituted with one to three substituents independently selected from the group consisting of: alkyl, cycloalkyl, halogen, hydroxy, alkoxy, cycloalkylalkoxy, haloalkyl, haloalkoxy, alkylsulfonyl and cycloalkylsulfonyl;

$R^2$ is selected from the group consisting of: hydrogen, alkyl and cycloalkyl;

$R^3$ is selected from the group consisting of: indanyl, substituted indanyl, pyridinyl, substituted pyridinyl, pyrimidyl, substituted pyrimidyl, phenyl and substituted phenyl, wherein substituted indanyl, substituted pyridinyl and substituted pyrimidyl are substituted with one to three substituents independently selected from the group consisting of: alkyl, cycloalkyl, halogen, hydroxy, alkoxy, cycloalkylalkoxy, haloalkyl, haloalkoxy and alkenyl, and wherein substituted phenyl is phenyl substituted with one substituent selected from the group consisting of: alkyl, cycloalkyl, halogen, hydroxy, alkoxy, cycloalkylalkoxy, haloalkyl, haloalkoxy and alkenyl;

$R^4$ is selected from the group consisting of: hydrogen, alkyl and cycloalkyl;

one of $R^5$ and $R^6$ is selected from the group consisting of: hydrogen, alkyl and cycloalkyl, and the other one is selected from the group consisting of: hydrogen, alkyl, cycloalkyl, phenyl and substituted phenyl, wherein substituted phenyl is phenyl substituted with one to three substituents independently selected from the group consisting of: alkyl, cycloalkyl, halogen, hydroxy, alkoxy, cycloalkylalkoxy, haloalkyl, haloalkoxy, alkylsulfonyl and cycloalkylsulfonyl;

$R^7$ is selected from the group consisting of: hydrogen, alkyl and cycloalkyl, wherein, when $R^1$ is benzyloxy, both $R^2$ and $R^7$ are hydrogen;

$A^1$ is selected from the group consisting of: carbonyl, —S(O)$_2$—, —NHC(O)— and —CR$^5$R$^6$—; and $A^2$ is —O— or —NR$^7$—;

or a pharmaceutically acceptable salt thereof;

with the proviso that said compound is not 1-benzyl-4-dimethylamino-piperidine-4-carboxylic acid (3-trifluoromethyl-phenyl)-amide or 4-dimethylamino-1-isopropyl-piperidine-4-carboxylic acid phenylamide.

The present invention relates also in part to a process for the preparation of the aforementioned compound.

The present invention further relates in part to a pharmaceutical composition comprising the aforementioned compound and a therapeutically inert carrier.

A yet further aspect of the present invention is a method for the treatment or prophylaxis of diabetes, dyslipidemia, atherosclerosis or obesity, said method comprising administering an effective amount of the aforementioned compound.

DETAILED DESCRIPTION OF THE INVENTION

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples are methyl, ethyl, propyl, isopropyl, butyl, isobutyl, tert-butyl, the isomeric pentyls, the isomeric hexyls, the isomeric heptyls or the isomeric octyls. Preferred alkyl are methyl, ethyl, isopropyl, tert-butyl or isomeric pentyls. Particularly preferred alkyl are methyl, isopropyl or tert-butyl.

The term "cycloalkyl", alone or in combination, signifies a cycloalkyl ring with 3 to 8 carbon atoms and preferably a cycloalkyl ring with 3 to 6 carbon atoms. Examples are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl or cyclooctyl. A preferred cycloalkyl is cyclopentyl.

The term "alkenyl", alone or in combination, signifies a straight-chain or branched-chain alkenyl group with 2 to 8 carbon atoms, preferably a straight or branched-chain alkenyl group with 2 to 6 carbon atoms and particularly preferred a straight or branched-chain alkenyl group with 2 to 4 carbon atoms. Examples are vinyl, propenyl, isopropenyl, methylpropenyl, dimethylpropenyl, methylbutenyl, dimethylbutenyl, trimethylbutenyl, butadienyl, methylbutadienyl, dimethylbutadienyl or trimethylbutadienyl. Preferred alkenyl is vinyl.

The term "hydroxy", alone or in combination, signifies the —OH group.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy or tert-butoxy, preferably methoxy or isopropoxy. A particularly preferred alkoxy is isopropoxy.

The terms "halogen", alone or in combination, signifies fluorine, chlorine, bromine or iodine and preferably fluorine or chlorine.

The term "haloalkyl", alone or in combination, signifies an alkyl group as defined before, wherein one or more hydrogen atoms are replaced by a halogen atom. Examples of haloalkyl are fluoromethyl, difluoromethyl, trifluoromethyl, trifluoroethyl, trifluoromethylethyl or pentafluoroethyl. A preferred haloalkyl is trifluoromethyl.

The term "haloalkoxy", alone or in combination, signifies an alkoxy group as defined before, wherein one or more hydrogen atoms are replaced by a halogen atom. Examples of haloalkyl are fluoromethoxy, difluoromethoxy, trifluoromethoxy, trifluoroethoxy, trifluoromethylethoxy, trifluorodimethylethoxy or pentafluoroethoxy. Preferred haloalkoxy is trifluoromethoxy.

The term "carbonyl", alone or in combination, signifies the —C(O)— group.

The term "protecting group" refers to groups which are used to tblock the reactivity of functional groups such as amino groups or hydroxy groups. Examples of protecting groups are tert-butyloxycarbonyl (Boc), benzyloxycarbonyl (Cbz), fluorenylmethyloxycarbonyl (Fmoc) or benzyl (Bn). A preferred protecting group is tert-butyloxycarbonyl (Boc).

Cleavage of protecting group can be done using standard methods known by the man skilled in the art such as hydrogenation or in the presence of an acid, e.g. HCl or TFA, preferably HCl, or a base, e.g. triethylamine.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particularly preferred pharmaceutically acceptable salts of compounds of formula (I) are the hydrochloride salts, methanesulfonic acid salts and citric acid salts.

The present invention relates to a compound according to formula (I),

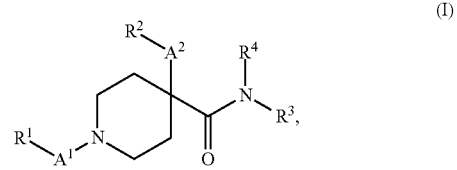

(I)

wherein $R^1$ is selected from the group consisting of: alkyl, cycloalkyl, cycloalkyalkyl, haloalkyl, thiophenyl, substituted thiophenyl, phenyl, substituted phenyl, benzyloxy, substituted benzyloxy, pyridinyl, substituted pyridinyl, pyrimidyl and substituted pyrimidyl, wherein substituted thiophenyl, substituted phenyl, substituted benzyloxy, substituted pyridinyl and substituted pyrimidyl are substituted with one to three substituents independently selected from the group consisting of: alkyl, cycloalkyl, halogen, hydroxy, alkoxy, cycloalkylalkoxy, haloalkyl, haloalkoxy, alkylsulfonyl and cycloalkylsulfonyl;

$R^2$ is selected from the group consisting of: hydrogen, alkyl and cycloalkyl;

$R^3$ is selected from the group consisting of: indanyl, substituted indanyl, pyridinyl, substituted pyridinyl, pyrimidyl, substituted pyrimidyl, phenyl and substituted phenyl, wherein substituted indanyl, substituted pyridinyl and substituted pyrimidyl are substituted with one to three substituents independently selected from the group consisting of: alkyl, cycloalkyl, halogen, hydroxy, alkoxy, cycloalkylalkoxy, haloalkyl, haloalkoxy and alkenyl, and wherein substituted phenyl is phenyl substituted with one substituent selected from the group consisting of: alkyl, cycloalkyl, halogen, hydroxy, alkoxy, cycloalkylalkoxy, haloalkyl, haloalkoxy and alkenyl;

$R^4$ is selected from the group consisting of: hydrogen, alkyl and cycloalkyl;

one of $R^5$ and $R^6$ is selected from the group consisting of: hydrogen, alkyl and cycloalkyl, and the other one is selected from the group consisting of: hydrogen, alkyl, cycloalkyl, phenyl and substituted phenyl, wherein substituted phenyl is phenyl substituted with one to three substituents independently selected from the group consisting of: alkyl, cycloalkyl, halogen, hydroxy, alkoxy, cycloalkylalkoxy, haloalkyl, haloalkoxy, alkylsulfonyl and cycloalkylsulfonyl;

$R^7$ is selected from the group consisting of: hydrogen, alkyl and cycloalkyl, wherein, when $R^1$ is benzyloxy, both $R^2$ and $R^7$ are hydrogen;

$A^1$ is selected from the group consisting of: carbonyl, —S(O)$_2$—, —NHC(O)— and —CR$^5$R$^6$—; and $A^2$ is —O— or —NR$^7$—;

or a pharmaceutically acceptable salt thereof;

with the proviso that said compound is not1-benzyl-4-dimethylamino-piperidine-4-carboxylic acid (3-trifluoromethylphenyl)-amide or 4-dimethylamino-1-isopropyl-piperidine-4-carboxylic acid phenylamide.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Preferred are the compounds of formula (I) and pharmaceutically acceptable salts or esters thereof.

Further preferred are the compounds of formula (I) and pharmaceutically acceptable salts thereof, particularly the compounds of formula (I).

Also further preferred are compounds of formula (I), wherein $R^1$ is alkyl, cycloalkyalkyl, haloalkyl, thiophenyl, phenyl, substituted phenyl, benzyloxy or substituted pyridinyl, wherein substituted phenyl and substituted pyridinyl are substituted with one to three, preferably one or two substituents, independently selected from the group consisting of: alkyl, halogen, alkoxy, haloalkyl, haloalkoxy and alkylsulfonyl.

Also further preferred are compounds of formula (I), wherein in case $R^1$ is benzyloxy then $A^1$ is carbonyl.

Particularly preferred are compounds of formula (I), wherein $R^1$ is substituted phenyl, wherein said phenyl is substituted with one to three substituents, preferably one substituent, independently selected from the group consisting of: alkyl, halogen and haloalkoxy.

Moreover preferred are compounds of formula (I), wherein $R^1$ is selected from the group consisting of: 2-methylphenyl, 2-chlorophenyl, 2-fluorophenyl and 2-trifluoromethoxyphenyl.

Preferred are compounds of formula (I), wherein $R^2$ is hydrogen or alkyl.

Another preferred embodiment of the present invention are the compounds according to formula (I), wherein $R^3$ is selected from the group consisting of: indanyl, substituted pyridinyl and substituted phenyl, wherein substituted pyridinyl is pyridinyl substituted with one to three alkyl substituents, preferably one alkyl substituent, and wherein substituted phenyl is phenyl substituted with one substituent selected from the group consisting of: alkyl, halogen, alkoxy, haloalkoxy and alkenyl.

Further preferred are compounds of formula (I), wherein $R^3$ is substituted phenyl, wherein said phenyl is substituted with one substituent selected from the group consisting of: alkyl, halogen, alkoxy, haloalkoxy and alkenyl.

More preferred are compounds of formula (I), wherein $R^3$ is substituted phenyl, wherein said phenyl is substituted in the 4-position with a substituent selected from the group consisting of: alkyl, alkoxy and haloalkoxy.

Moreover preferred are compounds of formula (I), wherein $R^3$ is selected from the group consisting of: 4-ethylphenyl, 4-isopropylphenyl, 4-tert-butylphenyl, 4-isopropoxyphenyl and 4-trifluoromethoxyphenyl.

Another preferred embodiment of the present invention are the compounds according to formula (I), wherein $A^1$ is —S(O)$_2$— or —CR$^5$R$^6$—.

Also preferred are the compounds according to formula (I), wherein $A^1$ is —NHC(O)— and is linked to $R^1$ such as to form (I-a)

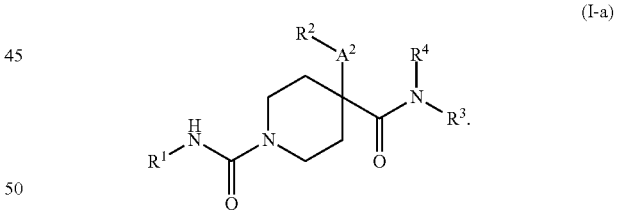

(I-a)

Moreover preferred are the compounds according to formula (I), wherein $A^1$ is —S(O)$_2$—.

Also preferred are compounds of formula (I), wherein one of $R^5$ and $R^6$ is hydrogen and the other one is hydrogen or phenyl.

Particularly preferred are compounds of formula (I), wherein both $R^5$ and $R^6$ are hydrogen.

Preferred are compounds of formula (I), wherein $A^2$ is —NR$^7$—.

Also preferred are compounds of formula (I), wherein $A^2$ is —O—.

Examples of preferred compounds of formula (I) are selected from the group consisting of:

1-Benzyl-4-hydroxy-piperidine-4-carboxylic acid (4-isopropyl-phenyl)-amide;

1-(4-Fluoro-benzyl)-4-hydroxy-piperidine-4-carboxylic acid (4-isopropyl-phenyl)-amide;
1-Benzyl-4-hydroxy-piperidine-4-carboxylic acid (4-tert-butyl-phenyl)-amide;
1-(3,3-Dimethyl-butyryl)-4-hydroxy-piperidine-4-carboxylic acid (4-isopropyl-phenyl)-amide;
4-Hydroxy-1-(toluene-4-sulfonyl)-piperidine-4-carboxylic acid (4-isopropyl-phenyl)-amide;
4-Hydroxy-piperidine-1,4-dicarboxylic acid 4-[(4-isopropyl-phenyl)-amide]1-[(4-trifluoromethyl-phenyl)-amide];
1-(2-Chloro-benzenesulfonyl)-4-hydroxy-piperidine-4-carboxylic acid (4-isopropyl-phenyl)-amide;
4-Hydroxy-1-(4-methoxy-benzenesulfonyl)-piperidine-4-carboxylic acid (4-isopropyl-phenyl)-amide;
4-Hydroxy-1-(4-trifluoromethyl-benzyl)-piperidine-4-carboxylic acid (4-isopropyl-phenyl)-amide;
1-(2-Chloro-benzenesulfonyl)-4-hydroxy-piperidine-4-carboxylic acid (4-trifluoromethoxy-phenyl)-amide;
1-(4-Fluoro-benzoyl)-4-hydroxy-piperidine-4-carboxylic acid (4-trifluoromethoxy-phenyl)-amide;
4-Hydroxy-1-(toluene-4-sulfonyl)-piperidine-4-carboxylic acid (4-isopropoxy-phenyl)-amide;
1-(2-Chloro-benzenesulfonyl)-4-hydroxy-piperidine-4-carboxylic acid (4-isopropoxy-phenyl)-amide;
4-Hydroxy-1-(4-trifluoromethoxy-benzyl)-piperidine-4-carboxylic acid (4-isopropoxy-phenyl)-amide;
4-Hydroxy-piperidine-1,4-dicarboxylic acid 4-[(4-tert-butyl-phenyl)-amide]1-[(4-trifluoromethyl-phenyl)-amide];
4-Hydroxy-1-(toluene-4-sulfonyl)-piperidine-4-carboxylic acid (4-tert-butyl-phenyl)-amide;
1-(2-Chloro-benzenesulfonyl)-4-hydroxy-piperidine-4-carboxylic acid (4-tert-butyl-phenyl)-amide;
1-(4-Fluoro-benzoyl)-4-hydroxy-piperidine-4-carboxylic acid (4-tert-butyl-phenyl)-amide;
4-Hydroxy-1-(4-methoxy-benzenesulfonyl)-piperidine-4-carboxylic acid (4-tert-butyl-phenyl)-amide;
4-Hydroxy-1-(4-trifluoromethyl-benzyl)-piperidine-4-carboxylic acid (4-tert-butyl-phenyl)-amide;
4-Hydroxy-1-(4-trifluoromethoxy-benzyl)-piperidine-4-carboxylic acid (4-tert-butyl-phenyl)-amide;
4-Hydroxy-1-(toluene-2-sulfonyl)-piperidine-4-carboxylic acid (4-tert-butyl-phenyl)-amide;
1-(2-Fluoro-benzenesulfonyl)-4-hydroxy-piperidine-4-carboxylic acid (4-tert-butyl-phenyl)-amide;
4-Hydroxy-1-(2-methoxy-benzenesulfonyl)-piperidine-4-carboxylic acid (4-tert-butyl-phenyl)-amide;
4-Hydroxy-1-(2-methanesulfonyl-benzenesulfonyl)-piperidine-4-carboxylic acid (4-tert-butyl-phenyl)-amide;
1-(4-Chloro-2-fluoro-benzenesulfonyl)-4-hydroxy-piperidine-4-carboxylic acid (4-tert-butyl-phenyl)-amide;
1-(2,4-Difluoro-benzenesulfonyl)-4-hydroxy-piperidine-4-carboxylic acid (4-tert-butyl-phenyl)-amide;
1-(2,4-Dimethoxy-benzenesulfonyl)-4-hydroxy-piperidine-4-carboxylic acid (4-tert-butyl-phenyl)-amide;
1-(4-Fluoro-2-methyl-benzenesulfonyl)-4-hydroxy-piperidine-4-carboxylic acid (4-tert-butyl-phenyl)-amide;
4-Hydroxy-1-(2-methoxy-5-methyl-benzenesulfonyl)-piperidine-4-carboxylic acid (4-tert-butyl-phenyl)-amide;
1-(2,5-Dimethoxy-benzenesulfonyl)-4-hydroxy-piperidine-4-carboxylic acid (4-tert-butyl-phenyl)-amide;
1-(2,5-Difluoro-benzenesulfonyl)-4-hydroxy-piperidine-4-carboxylic acid (4-tert-butyl-phenyl)-amide;
1-(2,5-Dimethyl-benzenesulfonyl)-4-hydroxy-piperidine-4-carboxylic acid (4-tert-butyl-phenyl)-amide;
1-(5-Fluoro-2-methyl-benzenesulfonyl)-4-hydroxy-piperidine-4-carboxylic acid (4-tert-butyl-phenyl)-amide;
1-(5-Fluoro-2-methoxy-benzenesulfonyl)-4-hydroxy-piperidine-4-carboxylic acid (4-tert-butyl-phenyl)-amide;
4-Hydroxy-1-(2-methyl-benzoyl)-piperidine-4-carboxylic acid (4-tert-butyl-phenyl)-amide;
1-(2-Fluoro-benzoyl)-4-hydroxy-piperidine-4-carboxylic acid (4-tert-butyl-phenyl)-amide;
1-(2-Chloro-benzoyl)-4-hydroxy-piperidine-4-carboxylic acid (4-tert-butyl-phenyl)-amide;
4-Hydroxy-1-(2-trifluoromethyl-benzoyl)-piperidine-4-carboxylic acid (4-tert-butyl-phenyl)-amide;
4-Hydroxy-1-(2-trifluoromethoxy-benzoyl)-piperidine-4-carboxylic acid (4-tert-butyl-phenyl)-amide;
1-(2,4-Difluoro-benzoyl)-4-hydroxy-piperidine-4-carboxylic acid (4-tert-butyl-phenyl)-amide;
1-(4-Fluoro-2-trifluoromethyl-benzoyl)-4-hydroxy-piperidine-4-carboxylic acid (4-tert-butyl-phenyl)-amide;
1-(2,5-Difluoro-benzoyl)-4-hydroxy-piperidine-4-carboxylic acid (4-tert-butyl-phenyl)-amide;
1-(2-Chloro-benzyl)-4-hydroxy-piperidine-4-carboxylic acid (4-tert-butyl-phenyl)-amide;
1-(2-Fluoro-benzyl)-4-hydroxy-piperidine-4-carboxylic acid (4-tert-butyl-phenyl)-amide;
4-Hydroxy-1-(2-methyl-benzyl)-piperidine-4-carboxylic acid (4-tert-butyl-phenyl)-amide;
4-Hydroxy-1-(2-trifluoromethyl-benzyl)-piperidine-4-carboxylic acid (4-tert-butyl-phenyl)-amide;
4-Hydroxy-1-(2-trifluoromethoxy-benzyl)-piperidine-4-carboxylic acid (4-tert-butyl-phenyl)-amide;
4-Hydroxy-piperidine-1,4-dicarboxylic acid 4-[(4-tert-butyl-phenyl)-amide]1-[(2,5-dimethoxy-phenyl)-amide];
4-Hydroxy-piperidine-1,4-dicarboxylic acid 4-[(4-tert-butyl-phenyl)-amide]1-[(5-chloro-2-methoxy-phenyl)-amide];
1-(3,3-Dimethyl-butyryl)-4-hydroxy-piperidine-4-carboxylic acid (4-trifluoromethoxy-phenyl)-amide;
4-Hydroxy-piperidine-1,4-dicarboxylic acid 1-[(4-fluoro-phenyl)-amide]-4-[(4-trifluoromethoxy-phenyl)-amide];
1-(2-Cyclopentyl-acetyl)-4-hydroxy-piperidine-4-carboxylic acid (4-trifluoromethoxy-phenyl)-amide;
4-Hydroxy-1-(2-methyl-propane-1-sulfonyl)-piperidine-4-carboxylic acid (4-trifluoromethoxy-phenyl)-amide;
1-(2,2-Dimethyl-propane-1-sulfonyl)-4-hydroxy-piperidine-4-carboxylic acid (4-trifluoromethoxy-phenyl)-amide;
1-(2-Chloro-benzoyl)-4-hydroxy-piperidine-4-carboxylic acid (4-trifluoromethoxy-phenyl)-amide;
4-Hydroxy-1-(thiophene-2-sulfonyl)-piperidine-4-carboxylic acid (4-trifluoromethoxy-phenyl)-amide;
1-(2-Fluoro-benzyl)-4-hydroxy-piperidine-4-carboxylic acid (4-trifluoromethoxy-phenyl)-amide;
4-Hydroxy-1-(toluene-2-sulfonyl)-piperidine-4-carboxylic acid (4-trifluoromethoxy-phenyl)-amide;
4-Hydroxy-1-(toluene-4-sulfonyl)-piperidine-4-carboxylic acid (4-trifluoromethoxy-phenyl)-amide;
1-(2-Fluoro-benzenesulfonyl)-4-hydroxy-piperidine-4-carboxylic acid (4-trifluoromethoxy-phenyl)-amide;
4-Hydroxy-1-(3,3,3-trifluoro-propane-1-sulfonyl)-piperidine-4-carboxylic acid (4-trifluoromethoxy-phenyl)-amide;
1-(2-Chloro-benzyl)-4-hydroxy-piperidine-4-carboxylic acid (4-trifluoromethoxy-phenyl)-amide;
4-Hydroxy-1-(2-trifluoromethyl-benzenesulfonyl)-piperidine-4-carboxylic acid (4-trifluoromethoxy-phenyl)-amide;
1-(2,2-Dimethyl-propane-1-sulfonyl)-4-hydroxy-piperidine-4-carboxylic acid methyl-(4-trifluoromethoxy-phenyl)-amide;

4-Hydroxy-1-(thiophene-2-sulfonyl)-piperidine-4-carboxylic acid methyl-(4-trifluoromethoxy-phenyl)-amide;
1-(2-Fluoro-benzyl)-4-hydroxy-piperidine-4-carboxylic acid methyl-(4-trifluoromethoxy-phenyl)-amide;
4-Hydroxy-1-(toluene-2-sulfonyl)-piperidine-4-carboxylic acid methyl-(4-trifluoromethoxy-phenyl)-amide;
4-Hydroxy-1-(toluene-4-sulfonyl)-piperidine-4-carboxylic acid methyl-(4-trifluoromethoxy-phenyl)-amide;
1-(2-Fluoro-benzenesulfonyl)-4-hydroxy-piperidine-4-carboxylic acid methyl-(4-trifluoromethoxy-phenyl)-amide;
1-(2-Chloro-benzyl)-4-hydroxy-piperidine-4-carboxylic acid methyl-(4-trifluoromethoxy-phenyl)-amide;
1-(2-Chloro-benzenesulfonyl)-4-hydroxy-piperidine-4-carboxylic acid methyl-(4-trifluoromethoxy-phenyl)-amide;
4-Hydroxy-1-(2-trifluoromethyl-benzenesulfonyl)-piperidine-4-carboxylic acid methyl-(4-trifluoromethoxy-phenyl)-amide;
4-Hydroxy-1-(toluene-2-sulfonyl)-piperidine-4-carboxylic acid ethyl-(4-trifluoromethoxy-phenyl)-amide;
1-(2-Fluoro-benzenesulfonyl)-4-hydroxy-piperidine-4-carboxylic acid ethyl-(4-trifluoromethoxy-phenyl)-amide;
1-(2-Chloro-benzenesulfonyl)-4-methoxy-piperidine-4-carboxylic acid (4-tert-butyl-phenyl)-amide;
4-Amino-1-(toluene-4-sulfonyl)-piperidine-4-carboxylic acid (4-tert-butyl-phenyl)-amide;
4-Amino-1-(toluene-4-sulfonyl)-piperidine-4-carboxylic acid (4-tert-butyl-phenyl)-amide hydrochloride;
4-Amino-1-(toluene-4-sulfonyl)-piperidine-4-carboxylic acid (4-isopropyl-phenyl)-amide;
4-Amino-1-(toluene-4-sulfonyl)-piperidine-4-carboxylic acid (4-isopropyl-phenyl)-amide hydrochloride;
4-Amino-1-(toluene-4-sulfonyl)-piperidine-4-carboxylic acid (4-isopropoxy-phenyl)-amide;
4-Amino-1-(toluene-4-sulfonyl)-piperidine-4-carboxylic acid (4-isopropoxy-phenyl)-amide hydrochloride;
4-Amino-1-(toluene-4-sulfonyl)-piperidine-4-carboxylic acid (4-trifluoromethoxy-phenyl)-amide;
4-Amino-1-(toluene-4-sulfonyl)-piperidine-4-carboxylic acid (4-trifluoromethoxy-phenyl)-amide hydrochloride;
4-Amino-1-(toluene-4-sulfonyl)-piperidine-4-carboxylic acid (4-ethyl-phenyl)-amide;
4-Amino-4-(4-isopropyl-phenylcarbamoyl)-piperidine-1-carboxylic acid benzyl ester;
4-Amino-4-(4-isopropyl-phenylcarbamoyl)-piperidine-1-carboxylic acid benzyl ester hydrochloride;
4-Amino-1-(4-isopropyl-benzenesulfonyl)-piperidine-4-carboxylic acid (4-isopropyl-phenyl)-amide;
4-Amino-1-(4-isopropyl-benzenesulfonyl)-piperidine-4-carboxylic acid (4-isopropyl-phenyl)-amide hydrochloride;
4-Amino-piperidine-1,4-dicarboxylic acid 4-p-tolylamide 1-[(4-trifluoromethoxy-phenyl)-amide];
4-Amino-piperidine-1,4-dicarboxylic acid 4-p-tolylamide 1-[(4-trifluoromethoxy-phenyl)-amide]hydrochloride;
4-Amino-piperidine-1,4-dicarboxylic acid 4-[(4-isopropyl-phenyl)-amide]1-[(4-trifluoromethoxy-phenyl)-amide];
4-Amino-piperidine-1,4-dicarboxylic acid 4-[(4-isopropyl-phenyl)-amide]1-[(4-trifluoromethoxy-phenyl)-amide]hydrochloride;
4-Amino-piperidine-1,4-dicarboxylic acid 4-[(4-tert-butyl-phenyl)-amide]1-[(4-trifluoromethoxy-phenyl)-amide];
4-Amino-piperidine-1,4-dicarboxylic acid 4-[(4-tert-butyl-phenyl)-amide]1-[(4-trifluoromethoxy-phenyl)-amide] hydrochloride;
4-Amino-piperidine-1,4-dicarboxylic acid 1-[(4-tert-butyl-phenyl)-amide]-4-[(4-fluoro-phenyl)-amide];
4-Amino-piperidine-1,4-dicarboxylic acid 1-[(4-tert-butyl-phenyl)-amide]-4-[(4-fluoro-phenyl)-amide]hydrochloride;
4-Amino-piperidine-1,4-dicarboxylic acid 1-[(4-tert-butyl-phenyl)-amide]-4-p-tolylamide;
4-Amino-piperidine-1,4-dicarboxylic acid 1-[(4-tert-butyl-phenyl)-amide]-4-p-tolylamide hydrochloride;
4-Amino-piperidine-1,4-dicarboxylic acid 1-[(4-tert-butyl-phenyl)-amide]-4-[(4-isopropyl-phenyl)-amide];
4-Amino-piperidine-1,4-dicarboxylic acid 1-[(4-tert-butyl-phenyl)-amide]-4-[(4-isopropyl-phenyl)-amide]hydrochloride;
4-Amino-piperidine-1,4-dicarboxylic acid bis-[(4-tert-butyl-phenyl)-amide];
4-Amino-piperidine-1,4-dicarboxylic acid bis-[(4-tert-butyl-phenyl)-amide]hydrochloride;
4-Amino-1-(2-chloro-benzenesulfonyl)-piperidine-4-carboxylic acid (3-trifluoromethyl-phenyl)-amide;
4-Amino-1-(2-chloro-benzenesulfonyl)-piperidine-4-carboxylic acid (3-ethyl-phenyl)-amide;
4-Amino-1-(2-chloro-benzenesulfonyl)-piperidine-4-carboxylic acid (4-ethyl-phenyl)-amide;
4-Amino-1-(2-chloro-benzenesulfonyl)-piperidine-4-carboxylic acid (4-fluoro-phenyl)-amide;
4-Amino-1-(2-chloro-benzenesulfonyl)-piperidine-4-carboxylic acid (4-chloro-phenyl)-amide;
4-Amino-1-(2-chloro-benzenesulfonyl)-piperidine-4-carboxylic acid (4-isopropoxy-phenyl)-amide;
4-Amino-1-(2-chloro-benzenesulfonyl)-piperidine-4-carboxylic acid (4-difluoromethoxy-phenyl)-amide;
4-Amino-1-(2-chloro-benzenesulfonyl)-piperidine-4-carboxylic acid (4-propyl-phenyl)-amide;
4-Amino-1-(2-chloro-benzenesulfonyl)-piperidine-4-carboxylic acid indan-5-ylamide;
4-Amino-1-(2-chloro-benzenesulfonyl)-piperidine-4-carboxylic acid (4-vinyl-phenyl)-amide;
4-Amino-1-(2-chloro-benzenesulfonyl)-piperidine-4-carboxylic acid (6-isopropyl-pyridin-3-yl)-amide;
4-Amino-1-(2-chloro-benzenesulfonyl)-piperidine-4-carboxylic acid [4-(2,2,2-trifluoro-1,1-dimethyl-ethoxy)-phenyl]-amide;
4-Amino-1-(2-chloro-benzenesulfonyl)-piperidine-4-carboxylic acid (4-trifluoromethoxy-phenyl)-amide;
4-Amino-1-(2-chloro-benzenesulfonyl)-piperidine-4-carboxylic acid (4-butyl-phenyl)-amide;
4-Amino-1-(2-chloro-benzenesulfonyl)-piperidine-4-carboxylic acid [4-(2,2,2-trifluoro-ethoxy)-phenyl]-amide;
4-Amino-piperidine-1,4-dicarboxylic acid 1-[(4-fluoro-phenyl)-amide]-4-[(4-isopropyl-phenyl)-amide];
4-Amino-piperidine-1,4-dicarboxylic acid 1-[(4-fluoro-phenyl)-amide]-4-[(4-isopropyl-phenyl)-amide]hydrochloride;
4-Amino-piperidine-1,4-dicarboxylic acid bis-[(4-isopropyl-phenyl)-amide];
4-Amino-piperidine-1,4-dicarboxylic acid bis-[(4-isopropyl-phenyl)-amide]hydrochloride;
4-Amino-piperidine-1,4-dicarboxylic acid 1-[(4-chloro-phenyl)-amide]-4-[(4-isopropyl-phenyl)-amide];
4-Amino-piperidine-1,4-dicarboxylic acid 1-[(4-chloro-phenyl)-amide]-4-[(4-isopropyl-phenyl)-amide]hydrochloride;
4-Amino-1-(2-fluoro-benzyl)-piperidine-4-carboxylic acid (4-isopropyl-phenyl)-amide;
4-Amino-1-(2-fluoro-benzyl)-piperidine-4-carboxylic acid (4-isopropyl-phenyl)-amide hydrochloride;
4-Amino-1-(2-chloro-benzyl)-piperidine-4-carboxylic acid (4-isopropyl-phenyl)-amide;

4-Amino-1-(2-chloro-benzyl)-piperidine-4-carboxylic acid (4-isopropyl-phenyl)-amide hydrochloride;
4-Amino-1-(3-fluoro-benzyl)-piperidine-4-carboxylic acid (4-isopropyl-phenyl)-amide;
4-Amino-1-(3-fluoro-benzyl)-piperidine-4-carboxylic acid (4-isopropyl-phenyl)-amide hydrochloride;
4-Amino-1-(4-trifluoromethyl-benzyl)-piperidine-4-carboxylic acid (4-isopropyl-phenyl)-amide;
4-Amino-1-(4-trifluoromethyl-benzyl)-piperidine-4-carboxylic acid (4-isopropyl-phenyl)-amide hydrochloride;
4-Amino-1-(2-trifluoromethoxy-benzyl)-piperidine-4-carboxylic acid (4-isopropyl-phenyl)-amide;
4-Amino-1-(2-trifluoromethoxy-benzyl)-piperidine-4-carboxylic acid (4-isopropyl-phenyl)-amide hydrochloride;
4-Amino-1-(2-trifluoromethyl-benzyl)-piperidine-4-carboxylic acid (4-isopropyl-phenyl)-amide;
4-Amino-1-(2-trifluoromethyl-benzyl)-piperidine-4-carboxylic acid (4-isopropyl-phenyl)-amide hydrochloride;
4-Amino-1-(4-isopropyl-benzyl)-piperidine-4-carboxylic acid (4-isopropyl-phenyl)-amide;
4-Amino-1-(4-isopropyl-benzyl)-piperidine-4-carboxylic acid (4-isopropyl-phenyl)-amide hydrochloride;
4-Amino-1-(2-chloro-benzenesulfonyl)-piperidine-4-carboxylic acid (4-isopropyl-phenyl)-amide;
4-Amino-1-(2-chloro-benzenesulfonyl)-piperidine-4-carboxylic acid (4-isopropyl-phenyl)-amide hydrochloride;
4-Amino-1-(3-chloro-benzenesulfonyl)-piperidine-4-carboxylic acid (4-isopropyl-phenyl)-amide;
4-Amino-1-(2-fluoro-benzenesulfonyl)-piperidine-4-carboxylic acid (4-isopropyl-phenyl)-amide;
4-Amino-1-(toluene-2-sulfonyl)-piperidine-4-carboxylic acid (4-isopropyl-phenyl)-amide;
4-Amino-1-(2-methyl-propane-1-sulfonyl)-piperidine-4-carboxylic acid (4-isopropyl-phenyl)-amide;
4-Amino-1-(2-methyl-propane-1-sulfonyl)-piperidine-4-carboxylic acid (4-isopropyl-phenyl)-amide hydrochloride;
4-Amino-1-(4-fluoro-benzyl)-piperidine-4-carboxylic acid (4-isopropyl-phenyl)-amide
4-Amino-1-(4-fluoro-benzyl)-piperidine-4-carboxylic acid (4-isopropyl-phenyl)-amide hydrochloride;
4-Amino-1-benzyl-piperidine-4-carboxylic acid (4-isopropyl-phenyl)-amide;
4-Amino-1-(2-trifluoromethoxy-benzoyl)-piperidine-4-carboxylic acid (4-isopropyl-phenyl)-amide;
4-Amino-1-(2-chloro-benzoyl)-piperidine-4-carboxylic acid (4-isopropyl-phenyl)-amide;
4-Amino-1-(4-chloro-benzoyl)-piperidine-4-carboxylic acid (4-isopropyl-phenyl)-amide;
4-Amino-1-(4-trifluoromethyl-benzoyl)-piperidine-4-carboxylic acid (4-isopropyl-phenyl)-amide;
4-Amino-1-(4-fluoro-benzoyl)-piperidine-4-carboxylic acid (4-isopropyl-phenyl)-amide;
4-Amino-1-(3-methyl-butyryl)-piperidine-4-carboxylic acid (4-isopropyl-phenyl)-amide;
4-Amino-1-(4-methyl-pentanoyl)-piperidine-4-carboxylic acid (4-isopropyl-phenyl)-amide;
4-Amino-1-(6-trifluoromethyl-pyridine-3-carbonyl)-piperidine-4-carboxylic acid (4-isopropyl-phenyl)-amide;
4-Amino-1-(2-chloro-4-trifluoromethyl-benzenesulfonyl)-piperidine-4-carboxylic acid (4-isopropyl-phenyl)-amide;
4-Amino-4-(4-ethyl-phenylcarbamoyl)-piperidine-1-carboxylic acid benzyl ester;
4-Amino-1-benzenesulfonyl-piperidine-4-carboxylic acid (4-ethyl-phenyl)-amide;
4-Amino-1-(2-fluoro-benzenesulfonyl)-piperidine-4-carboxylic acid (4-ethyl-phenyl)-amide;
4-Amino-1-(toluene-2-sulfonyl)-piperidine-4-carboxylic acid (4-ethyl-phenyl)-amide;
4-Amino-1-(2-methanesulfonyl-benzenesulfonyl)-piperidine-4-carboxylic acid (4-ethyl-phenyl)-amide;
4-Amino-1-(2-methoxy-benzenesulfonyl)-piperidine-4-carboxylic acid (4-ethyl-phenyl)-amide;
4-Amino-1-(4-trifluoromethoxy-benzenesulfonyl)-piperidine-4-carboxylic acid (4-ethyl-phenyl)-amide;
4-Amino-1-(4-methoxy-benzenesulfonyl)-piperidine-4-carboxylic acid (4-ethyl-phenyl)-amide;
4-Amino-1-(4-ethyl-benzenesulfonyl)-piperidine-4-carboxylic acid (4-ethyl-phenyl)-amide;
4-Amino-1-(4-butyl-benzenesulfonyl)-piperidine-4-carboxylic acid (4-ethyl-phenyl)-amide;
4-Amino-1-(2,6-difluoro-benzenesulfonyl)-piperidine-4-carboxylic acid (4-ethyl-phenyl)-amide;
4-Amino-1-(butane-1-sulfonyl)-piperidine-4-carboxylic acid (4-ethyl-phenyl)-amide;
4-Amino-1-cyclohexylmethanesulfonyl-piperidine-4-carboxylic acid (4-ethyl-phenyl)-amide;
4-Amino-1-(2-trifluoromethyl-benzenesulfonyl)-piperidine-4-carboxylic acid (4-ethyl-phenyl)-amide;
4-Amino-1-(2-chloro-4-fluoro-benzenesulfonyl)-piperidine-4-carboxylic acid (4-ethyl-phenyl)-amide;
4-Amino-1-(2-chloro-4-trifluoromethyl-benzenesulfonyl)-piperidine-4-carboxylic acid (4-ethyl-phenyl)-amide;
4-Amino-1-(6-chloro-pyridine-3-sulfonyl)-piperidine-4-carboxylic acid (4-ethyl-phenyl)-amide;
4-Amino-1-(2-trifluoromethoxy-benzenesulfonyl)-piperidine-4-carboxylic acid (4-ethyl-phenyl)-amide;
4-Amino-1-(2,6-dichloro-benzenesulfonyl)-piperidine-4-carboxylic acid (4-ethyl-phenyl)-amide;
4-Amino-1-benzyl-piperidine-4-carboxylic acid (4-ethyl-phenyl)-amide;
4-Amino-1-(2-methyl-benzyl)-piperidine-4-carboxylic acid (4-ethyl-phenyl)-amide;
4-Amino-1-(2-fluoro-benzyl)-piperidine-4-carboxylic acid (4-ethyl-phenyl)-amide;
4-Amino-1-(2-chloro-benzyl)-piperidine-4-carboxylic acid (4-ethyl-phenyl)-amide;
4-Amino-1-(2-difluoromethoxy-benzyl)-piperidine-4-carboxylic acid (4-ethyl-phenyl)-amide;
4-Amino-1-(2-trifluoromethoxy-benzyl)-piperidine-4-carboxylic acid (4-ethyl-phenyl)-amide;
4-Amino-1-(2-trifluoromethyl-benzyl)-piperidine-4-carboxylic acid (4-ethyl-phenyl)-amide;
4-Amino-1-(4-isopropyl-benzyl)-piperidine-4-carboxylic acid (4-ethyl-phenyl)-amide;
4-Amino-1-benzhydryl-piperidine-4-carboxylic acid (4-ethyl-phenyl)-amide; and
4-Methylamino-1-(toluene-4-sulfonyl)-piperidine-4-carboxylic acid (4-trifluoromethoxy-phenyl)-amide.

Examples of especially preferred compounds of formula (I) are selected from the group consisting of:
1-(2-Chloro-benzenesulfonyl)-4-hydroxy-piperidine-4-carboxylic acid (4-tert-butyl-phenyl)-amide;
4-Hydroxy-1-(toluene-2-sulfonyl)-piperidine-4-carboxylic acid (4-tert-butyl-phenyl)-amide;
1-(2-Chloro-benzyl)-4-hydroxy-piperidine-4-carboxylic acid methyl-(4-trifluoromethoxy-phenyl)-amide;
4-Amino-1-(toluene-4-sulfonyl)-piperidine-4-carboxylic acid (4-tert-butyl-phenyl)-amide;
4-Amino-1-(toluene-4-sulfonyl)-piperidine-4-carboxylic acid (4-tert-butyl-phenyl)-amide hydrochloride;
4-Amino-1-(toluene-4-sulfonyl)-piperidine-4-carboxylic acid (4-trifluoromethoxy-phenyl)-amide;

4-Amino-1-(toluene-4-sulfonyl)-piperidine-4-carboxylic acid (4-trifluoromethoxy-phenyl)-amide hydrochloride;

4-Amino-1-(2-chloro-benzenesulfonyl)-piperidine-4-carboxylic acid (4-ethyl-phenyl)-amide;

4-Amino-1-(2-chloro-benzenesulfonyl)-piperidine-4-carboxylic acid (4-isopropoxy-phenyl)-amide;

4-Amino-1-(2-chloro-benzenesulfonyl)-piperidine-4-carboxylic acid (4-trifluoromethoxy-phenyl)-amide;

4-Amino-1-(2-chloro-benzenesulfonyl)-piperidine-4-carboxylic acid (4-isopropyl-phenyl)-amide;

4-Amino-1-(2-chloro-benzenesulfonyl)-piperidine-4-carboxylic acid (4-isopropyl-phenyl)-amide hydrochloride;

4-Amino-1-(2-fluoro-benzenesulfonyl)-piperidine-4-carboxylic acid (4-isopropyl-phenyl)-amide; and 4-Amino-1-(2-trifluoromethoxy-benzenesulfonyl)-piperidine-4-carboxylic acid (4-ethyl-phenyl)-amide.

The process for the manufacture of compounds of formula (I) is an object of the invention.

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein.

Compounds of formula (I-b)

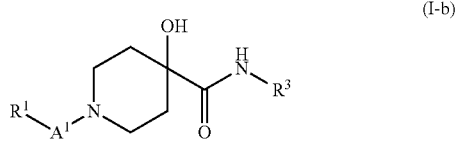

are readily accessible in a stepwise process as outlined in scheme 1.

i. Compounds of formula (II-a) are reacted with CDI or the like and an amine of general formula (III-a) in the presence of a base such as NEt$_3$, DIPEA and the like and followed by treatment with an acid such as HCl and the like to access spirocyclic compounds of formula (IV).

ii. Spirocyclic compounds of formula (IV) are subsequently reacted with a base such as NaOMe and the like to give compounds of formula (V-a).

iii. The protecting group (PG) of compounds of formula (V-a) can be cleaved according to standard procedures depending on the nature of the protecting group, such as by hydrogenation or in the presence of an acid or a base, to give compounds of formula (VI-a).

iv. Subsequent coupling reaction of compounds of formula (VI-a) with compounds of formula (VII) in the presence of a base give access to compounds of general formula (I-b). Alternatively, compounds of general formula (I-b), wherein A$^1$ is —NHC(O)— can be prepared by coupling compounds of formula (VI-a) with an appropriate isocyanate of formula (VIII) in the presence of a base. Another method to prepare compounds of general formula (I-b), wherein A$^1$ is carbonyl, consists in reacting compounds of formula (VI-a) with the appropriate acid derivatives of formula (IX) in the presence of coupling reagents such as HATU, TBTU, EDCI and the like and a base such as NEt$_3$, DIPEA and the like.

Scheme 1

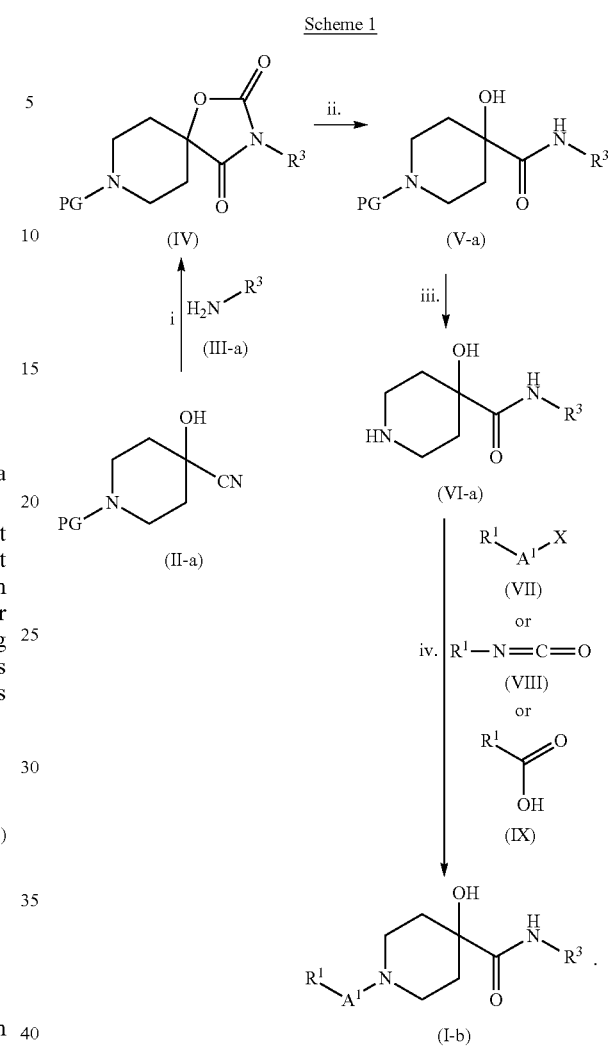

PG is e.g. benzyl, Boc or Cbz
X is halogen, preferably Cl

Compounds of formula (I-c), wherein R$^2$ is alkyl or cycloalkyl,

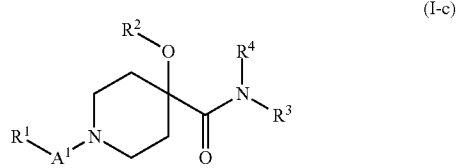

are readily accessible in a stepwise process as outlined in scheme 2.

v. Compounds of formula (II-b) are reacted with an appropriate compound of formula (X) in the presence of a base such as K$_2$CO$_3$ and the like to access compounds of formula (XI).

vi. Subsequent hydrolysis of compounds of formula (XI) under basic-aqueous conditions such as LiOH, NaOH, KOH and the like in water gives access to the corresponding acid of formula (XII-a).

vii. The acid of formula (XII-a) can conveniently be coupled with amines of general formula (III-b) in the presence of coupling reagents such as HATU, TBTU, EDCI and the like and of a base such as NEt₃, DIPEA and the like to access compounds of formula (V-b).

viii. The protecting group (PG) of compounds of formula (V-b) can be cleaved according to standard procedures depending on the nature of the protecting group, such as by hydrogenation or in the presence of an acid or a base, to give compounds of formula (VI-b).

ix. Subsequent coupling reaction of compounds of formula (VI-b) with appropriate compounds of formula (VII) in the presence of a base give access to compounds of general formula (I-c). Alternatively, compounds of general formula (I-c), wherein A¹ is —NHC(O)— can be prepared by coupling compounds of formula (VI-b) with an appropriate isocyanate of formula (VIII) in the presence of a base. Another method to prepare compounds of general formula (I-c), wherein A¹ is carbonyl, consists in reacting compounds of formula (VI-b) with the appropriate acid derivatives of formula (IX) in the presence of coupling reagents such as HATU, TBTU, EDCI and the like and a base such as NEt₃, DIPEA and the like.

Scheme 2

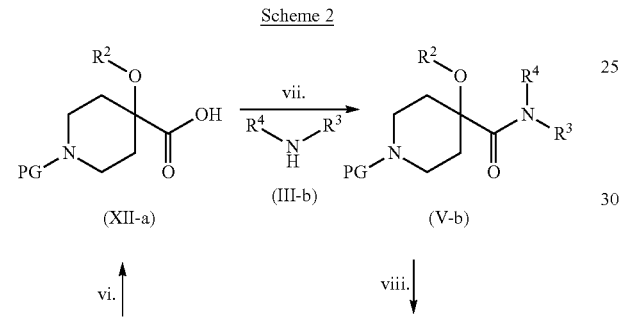

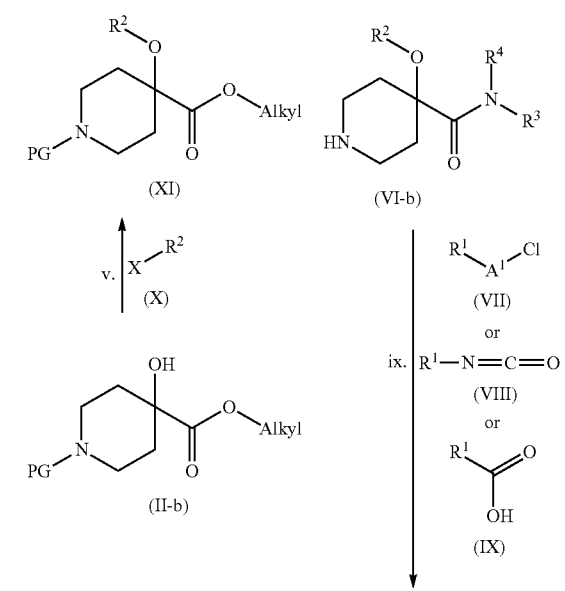

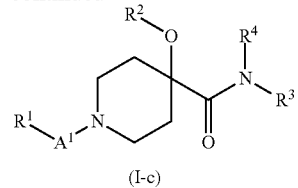

(I-c)

Alkyl is e.g. methyl or ethyl
PG is e.g. benzyl, Boc or Cbz
X is halogen, preferably Cl Compounds of formula (I-d)

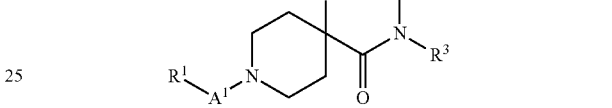

(I-d)

are readily accessible in a stepwise process as outlined in scheme 3.

x. Compounds of formula (II-c) are hydrolyzed under basic-aqueous conditions such as LiOH, NaOH, KOH and the like in water to give access to the corresponding acid of formula (XII-b).

xi. The acid of formula (XII-b) can conveniently be coupled with amines of general formula (III-b) in the presence of coupling reagents such as HATU, TBTU, EDCI and the like and of a base such as NEt₃, DIPEA and the like to access compounds of formula (V-c).

xii. The protecting group PG¹ of compounds of formula (V-c) can be cleaved according to standard procedures depending on the nature of the protecting group, such as by hydrogenation or in the presence of an acid or a base, to give compounds of formula (VI-c).

xiii. Subsequent coupling reaction of compounds of formula (VI-c) with appropriate compounds of formula (VII) in the presence of a base give access to compounds of general formula (I-e). Alternatively, compounds of general formula (I-e), wherein A¹ is —NHC(O)— can be prepared by coupling compounds of formula (VI-c) with an appropriate isocyanate of formula (VIII) in the presence of a base. Another method to prepare compounds of general formula (I-e), wherein A¹ is carbonyl, consists in reacting compounds of formula (VI-c) with the appropriate acid derivatives of formula (IX) in the presence of coupling reagents such as HATU, TBTU, EDCI and the like and a base such as NEt₃, DIPEA and the like.

xiv. The protecting group PG² of compounds of formula (I-e) can be cleaved according to standard procedures depending on the nature of the protecting group, such as by hydrogenation or in the presence of an acid or a base, to give compounds of formula (I-d).

Scheme 3

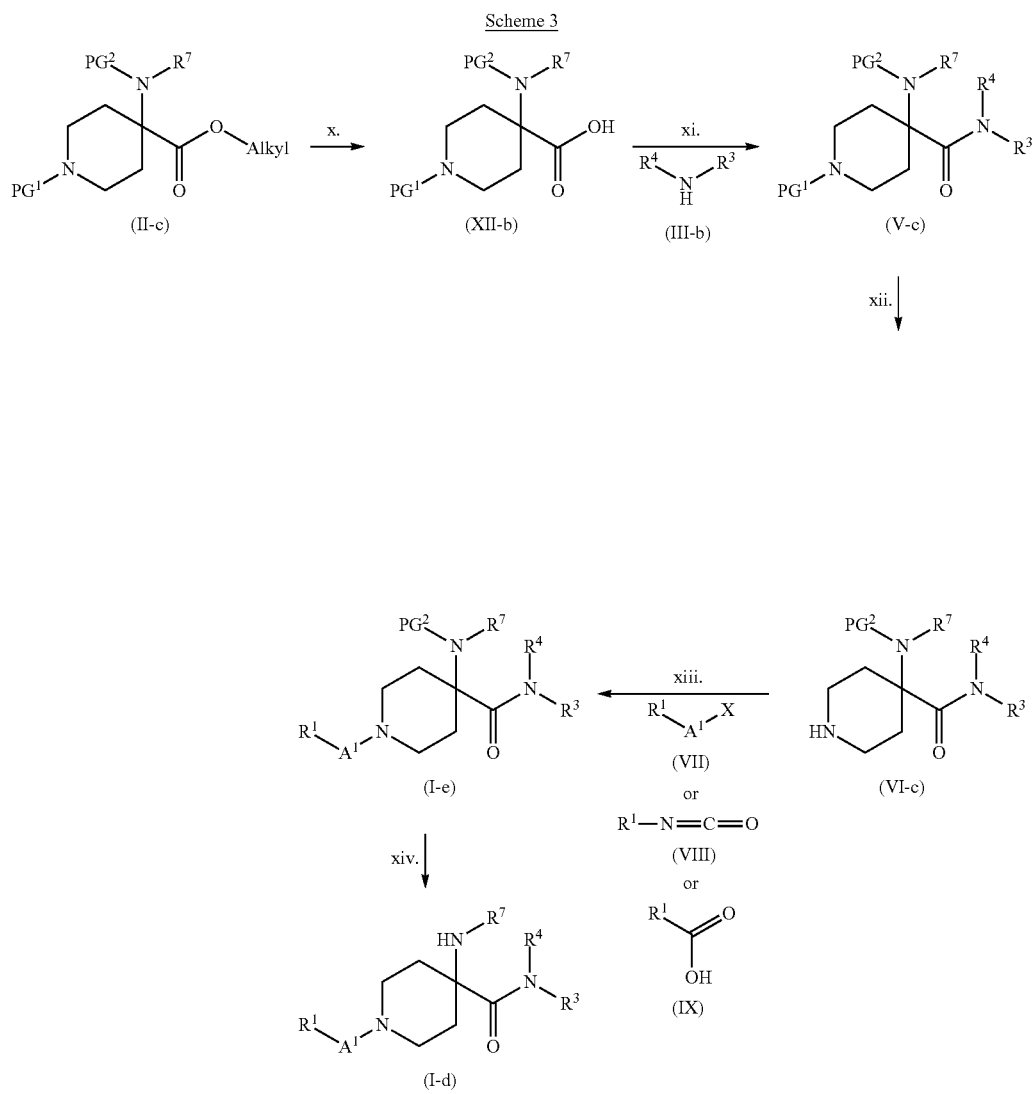

Alkyl is e.g. methyl or ethyl
PG is e.g. benzyl, Boc or Cbz
X is halogen, preferably Cl An alternative route to compounds of formula (I-d)

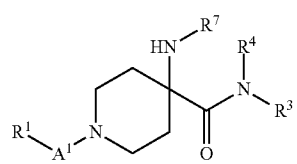

is outlined in scheme 4.

xv. Compounds of formula (VI-d) are coupled with appropriate compounds of formula (VII) in the presence of a base give access to compounds of general formula (XIII). Alternatively, compounds of general formula (XIII), wherein $A^1$ is —NHC(O)— can be prepared by coupling compounds of formula (VI-d) with an appropriate isocyanate of formula (VIII) in the presence of a base. Another method to prepare compounds of general formula (XIII), wherein $A^1$ is carbonyl, consists in reacting compounds of formula (VI-d) with the appropriate acid derivatives of formula (IX) in the presence of coupling reagents such as HATU, TBTU, EDCI and the like and a base such as $NEt_3$, DIPEA and the like.

xvi. Compounds of formula (XIII) are hydrolyzed under basic-aqueous conditions such as LiOH, NaOH, KOH and the like in water to give access to the corresponding acid of formula (XIV).

xvii. The acid of formula (XIV) can conveniently be coupled with amines of general formula (III-b) in the presence of coupling reagents such as HATU, TBTU, EDCI and the like and of a base such as $NEt_3$, DIPEA and the like to access compounds of formula (I-f).

xviii. The protecting group (PG) of compounds of formula (I-g) can be cleaved according to standard procedures depending on the nature of the protecting group, such as by hydrogenation or in the presence of an acid or a base, to give compounds of formula (I-d).

Scheme 4

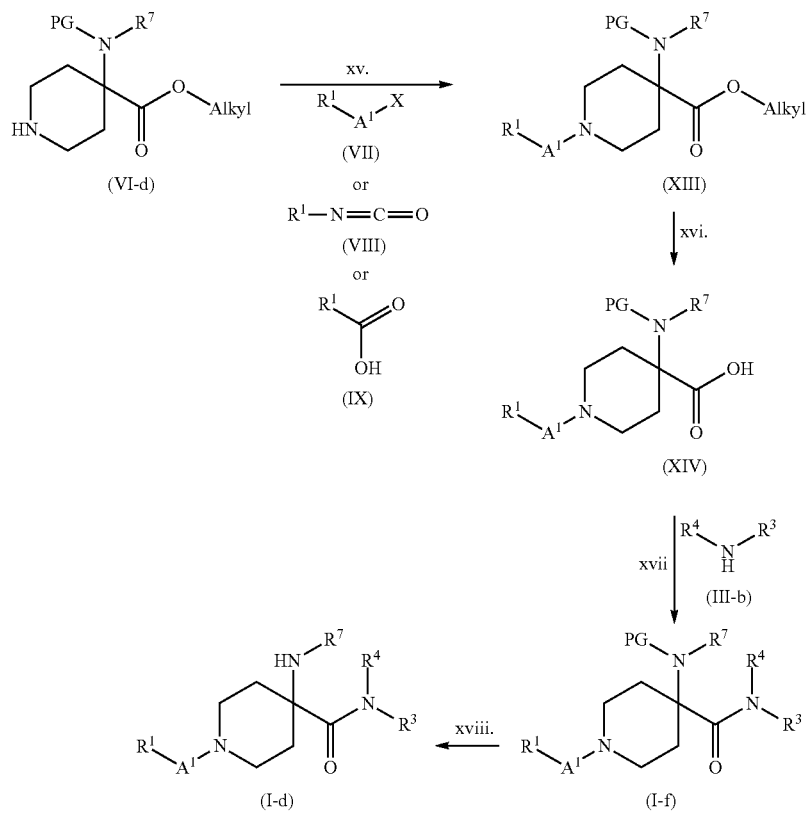

Alkyl is e.g. methyl or ethyl
PG is e.g. benzyl, Boc or Cbz
X is halogen, preferably Cl Compounds of formula (I-g), wherein $R^2$ is alkyl or cycloalkyl

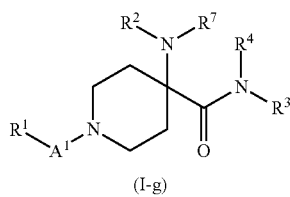

are readily accessible as outlined in scheme 5.

xix. Compounds of formula (I-d) are reacted with compounds of formula (X) in the presence of a base such as $K_2CO_3$ and the like to access compounds of formula (I-g).

X is halogen, preferably I or Cl

Preferred is a process to prepare a compound of formula (I) comprising a) reaction of a compound of formula (VI) in the presence of a compound of formula (VII), wherein $A^1$, $A^2$, $R^1$, $R^2$, $R^3$, $R^4$ and $R^7$ are defined as before and X is halogen;

Scheme 5

-continued

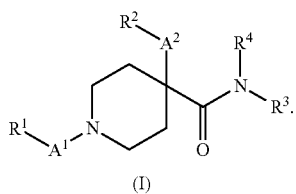

(I)

Preferably in the presence of a base, particularly triethylamine, in a solvent, particularly dichloromethane, and at a temperature comprised between −10° C. and reflux of the solvent, particularly RT, a preferred halogen is chlorine;

b) reaction of a compound of formula (VI) in the presence of a compound of formula (VIII), wherein $A^2$, $R^1$, $R^2$, $R^3$, $R^4$ and $R^7$ are defined as before and $A^1$ is —NHC(O)—;

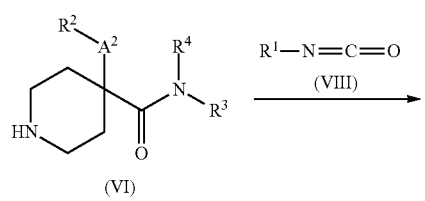

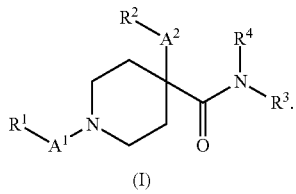

(I)

Preferably in the presence of a base, particularly triethylamine, in a solvent, particularly dichloromethane, and at a temperature comprised between −10° C. and reflux of the solvent, particularly RT;

c) reaction of a compound of formula (VI) in the presence of a compound of formula (IX), wherein $A^2$, $R^1$, $R^2$, $R^3$, $R^4$ and $R^7$ are defined as before and $A^1$ is carbonyl;

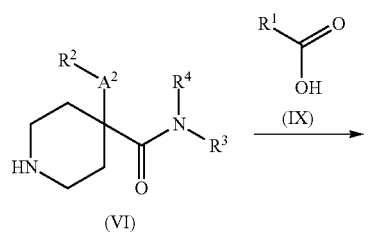

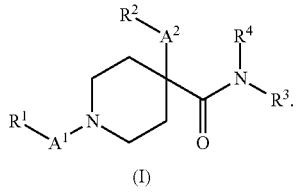

(I)

Preferably in the presence of a coupling agent, particularly HATU or EDCI, a base, particularly DIEPA or DMAP, in a solvent, particularly DMF, and at a temperature between −10° C. and reflux of solvent, particularly at RT;

d) reaction of a compound of formula (I-h) in the presence of a compound of formula (X), wherein $A^1$, $A^2$, $R^1$, $R^3$, $R^4$ and $R^7$ are defined as before, $R^2$ is alkyl or cycloalkyl and X is halogen;

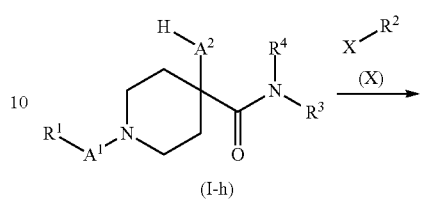

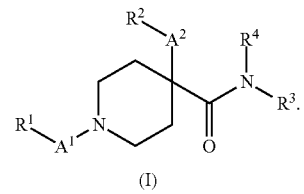

(I)

Preferably in the presence of a base, particularly $K_2CO_3$ or NaH, in a solvent, particularly DMF, and at a temperature comprised between −10° C. and reflux, particularly comprised between RT and 40° C., a preferred halogen is chlorine; or e) reaction of a compound of formula (I-g) in order to cleave the protecting group (PG), wherein $A^1$, $R^1$, $R^3$, $R^4$ and $R^7$ are defined as before, $R^2$ is hydrogen, $A^2$ is —$NR^7$— and PG is a protecting group;

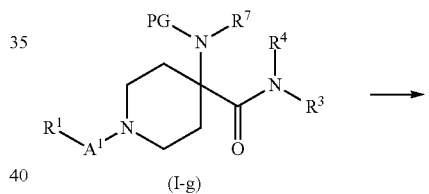

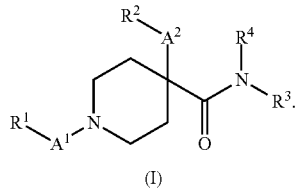

(I)

Preferably in presence of an acid, particularly HCl, in a solvent, particularly dioxane, at a temperature comprised between −10° C. and reflux of solvent, particularly between 40° C. and 110° C., a preferred protecting group is an acid-labile protecting group, particularly the Boc group;

Preferred intermediates are selected from:

8-Benzyl-3-(4-isopropyl-phenyl)-1-oxa-3,8-diaza-spiro[4.5]decane-2,4-dione;

4-Hydroxy-piperidine-4-carboxylic acid (4-isopropyl-phenyl)-amide;

4-Hydroxy-piperidine-4-carboxylic acid (4-trifluoromethoxy-phenyl)-amide;

4-Hydroxy-piperidine-4-carboxylic acid (4-isopropoxy-phenyl)-amide;

4-Hydroxy-piperidine-4-carboxylic acid (4-tert-butyl-phenyl)-amide;

4-Hydroxy-piperidine-4-carboxylic acid methyl-(4-trifluoromethoxy-phenyl)-amide;

4-Acetoxy-1-benzyl-piperidine-4-carboxylic acid;
Acetic acid 1-benzyl-4-[methyl-(4-trifluoromethoxy-phenyl)-carbamoyl]-piperidine-4-yl ester;
1-Benzyl-4-hydroxy-piperidine-4-carboxylic acid methyl-(4-trifluoromethoxy-phenyl)-amide;
4-Hydroxy-piperidine-4-carboxylic acid ethyl-(4-trifluoromethoxy-phenyl)-amide;
4-Methoxy-piperidine-4-carboxylic acid (4-tert-butyl-phenyl)-amide, hydrochloride;
4-tert-Butoxycarbonylamino-1-(toluene-4-sulfonyl)-piperidine-4-carboxylic acid methyl ester;
[4-(4-tert-Butyl-phenylcarbamoyl)-1-(toluene-4-sulfonyl)-piperidin-4-yl]-carbamic acid tert-butyl ester;
4-tert-Butoxycarbonylamino-4-(4-isopropyl-phenylcarbamoyl)-piperidine-1-carboxylic acid benzyl ester;
4-tert-Butoxycarbonylamino-1-(4-isopropyl-benzenesulfonyl)-piperidine-4-carboxylic acid methyl ester;
4-tert-Butoxycarbonylamino-1-(4-isopropyl-benzenesulfonyl)-piperidine-4-carboxylic acid methyl ester;
[1-(4-Isopropyl-benzenesulfonyl)-4-(4-isopropyl-phenylcarbamoyl)-piperidin-4-yl]-carbamic acid tert-butyl ester-
4-tert-Butoxycarbonylamino-1-(4-trifluoromethoxy-phenylcarbamoyl)-piperidine-4-carboxylic acid methyl ester;
[4-p-Tolylcarbamoyl-1-(4-trifluoromethoxy-phenylcarbamoyl)-piperidin-4-yl]-carbamic acid tert-butyl ester;
4-tert-Butoxycarbonylamino-1-(4-tert-butyl-phenylcarbamoyl)-piperidine-4-carboxylic acid methyl ester;
[1-(4-tert-Butyl-phenylcarbamoyl)-4-(4-fluoro-phenylcarbamoyl)-piperidin-4-yl]-carbamic acid tert-butyl ester;
4-tert-Butoxycarbonylamino-1-(2-chloro-benzenesulfonyl)-piperidine-4-carboxylic acid;
[4-(4-Isopropyl-phenylcarbamoyl)-piperidin-4-yl]-carbamic acid tert-butyl ester;
[1-(4-Fluoro-phenylcarbamoyl)-4-(4-isopropyl-phenylcarbamoyl)-piperidin-4-yl]-carbamic acid tert-butyl ester;
4-tert-Butoxycarbonylamino-4-(4-ethyl-phenylcarbamoyl)-piperidine-1-carboxylic acid benzyl ester; and
[4-(4-Ethyl-phenylcarbamoyl)-piperidin-4-yl]-carbamic acid tert-butyl ester.

Compounds of formula (I) as described before for use as therapeutically active substance are a further object of the invention.

Also an object of the present invention are the compounds of formula (I) as described before for the preparation of a medicament for the treatment or prophylaxis of illnesses which are caused by disorders associated e.g. with the enzyme hormone-sensitive lipase.

Likewise an object of the present invention are pharmaceutical compositions comprising a compound of formula (I) as described before and a therapeutically inert carrier.

A further preferred embodiment of the present invention is the use of a compound of the formula (I) as described before for the preparation of a medicament for the treatment or prophylaxis of diabetes, dyslipidemia, atherosclerosis or obesity.

Particularly preferred is the use of a compound according to formula (I) as described before for the preparation of medicaments for the treatment or prophylaxis of diabetes, dyslipidemia or obesity.

More preferred is the use of a compound according to formula (I) as described before for the preparation of medicaments for the treatment or prophylaxis of diabetes.

Moreover preferred is the use of a compound according to formula (I) as described before for the preparation of medicaments for the treatment or prophylaxis of diabetes Type II.

A further preferred object of the present invention are compounds of the formula (I) as described before for the preparation of a medicament for the treatment or prophylaxis of diabetes, dyslipidemia, atherosclerosis or obesity.

Particularly preferred are compounds of the formula (I) as described before for the preparation of a medicament for the treatment or prophylaxis of diabetes, dyslipidemia or obesity.

More preferred are compounds according to formula (I) as described before for the preparation of medicaments for the treatment or prophylaxis of diabetes.

Moreover preferred are compounds according to formula (I) as described before for the preparation of medicaments for the treatment or prophylaxis of diabetes Type II.

A further object of the present invention comprises a compound according to formula (I) as described before, when manufactured according to any one of the described processes.

Also an object of the invention is a method for the treatment or prophylaxis of diabetes, dyslipidemia, atherosclerosis or obesity, which method comprises administering an effective amount of a compound of formula (I) as described before.

Particularly preferred is a method for the treatment or prophylaxis of diabetes, dyslipidemia or obesity, which method comprises administering an effective amount of a compound according to formula (I) as described before.

More preferred is a method for the treatment or prophylaxis of diabetes, which method comprises administering an effective amount of a compound according to formula (I) as described before.

Moreover preferred is a method for the treatment or prophylaxis of diabetes Type II, which method comprises administering an effective amount of a compound according to formula (I) as described before.

Also an object of the present invention is the use of a compound according to formula (I) as described before for the preparation of a medicament for the treatment or prophylaxis of metabolic syndrome, cardiovascular diseases, myocardial dysfunction, inflammation, nonalkoholic fatty liver disease or nonalkoholic steatohepatitis.

A further preferred object of the present invention are compounds according to formula (I) as described before for the preparation of a medicament for the treatment or prophylaxis of metabolic syndrome, cardiovascular diseases, myocardial dysfunction, inflammation, nonalkoholic fatty liver disease or nonalkoholic steatohepatitis.

Also an object of the invention is a method for the treatment or prophylaxis of metabolic syndrome, cardiovascular diseases, myocardial dysfunction, inflammation, nonalkoholic fatty liver disease or nonalkoholic steatohepatitis, which method comprises administering an effective amount of a compound according to formula (I) as described before.

Assay Procedures

Production of Human Full Length Hormone Sensitive Lipase-His$^6$

1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His$^6$, 48 hr., containing 25 μM E-64. Cell count: 1.78×10$^{10}$ cells/ml, 90% viable.

Cells were thawed. On ice, cells were suspended in Base Buffer containing 10% glycerol, 25 mM Tris-Cl, 300 mM NaCl, 10 mM imidazole, 10 mM 2-mercaptoethanol, 2 μg pepstatin/ml, 2 μg leupeptin/ml, 2 μg antipain/ml, pH 8.0 at 4° C. in a final volume of 475 ml with 3.75×107 cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 μm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluted with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 μm membrane disposable filter unit (Millipore SCGP U02 RE) and the elute collected in the reservoir. The elute was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 μm disposable filter unit (Millipore SCGP00525). The protein concentration was calculated from absorbance at 280 nm, using 280=0.67 cm-1 mg-1. Yield was 235 mg, total. The protein was stored at −80° C. Human Hormone-Sensitive Lipase (HSL) enzyme inhibition assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay

The following assay was used to measure the effect of the compounds to inhibit lipolysis in intact cells (adipocytes):

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 μM). Each compound was then diluted 200-fold into KRBH/3% BSA (0.5% DMSO final). The resulting solutions range from 25 uM to 1.6 μM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Example | HSL hum IC$_{50}$ (uM) |
| --- | --- |
| 1 | 0.46 |
| 2 | 0.27 |
| 3 | 0.39 |
| 4 | 0.72 |
| 5 | 0.21 |
| 6 | 0.21 |
| 7 | 0.09 |
| 8 | 0.2 |
| 9 | 0.45 |
| 10 | 0.12 |
| 11 | 0.55 |
| 12 | 0.86 |
| 13 | 0.19 |
| 14 | 0.6 |
| 15 | 0.41 |
| 16 | 0.2 |
| 17 | 0.06 |
| 18 | 0.21 |
| 19 | 0.17 |
| 20 | 0.32 |
| 41 | 0.49 |
| 42 | 0.6 |
| 43 | 0.64 |
| 44 | 0.08 |
| 45 | 0.08 |
| 46 | 0.22 |
| 47 | 0.23 |
| 48 | 0.11 |
| 49 | 0.66 |
| 50 | 0.84 |
| 51 | 0.81 |
| 52 | 0.95 |
| 53 | 0.79 |
| 54 | 0.66 |
| 55 | 0.33 |
| 56 | 0.46 |
| 57 | 0.33 |
| 58 | 0.19 |
| 59 | 0.29 |
| 60 | 0.22 |
| 61 | 0.1 |
| 62 | 0.87 |
| 63 | 0.18 |
| 64 | 0.15 |
| 65 | 0.49 |

| Example | HSL hum IC$_{50}$ (uM) |
|---|---|
| 66 | 0.2 |
| 67 | 0.19 |
| 68 | 0.1 |
| 69 | 0.14 |
| 70 | 0.09 |
| 71 | 0.04 |
| 72 | 0.06 |
| 73 | 0.1 |
| 74 | 0.88 |
| 75 | 0.75 |
| 76 | 0.53 |
| 77 | 0.05 |
| 78 | 0.07 |
| 79 | 0.13 |
| 80 | 0.05 |
| 81 | 0.12 |
| 82 | 0.32 |
| 83 | 0.23 |
| 84 | 0.36 |
| 85 | 0.12 |
| 86 | 0.14 |
| 87 | 0.78 |
| 88 | 0.37 |
| 89 | 0.12 |
| 90 | 0.13 |
| 91 | 0.71 |
| 92 | 0.86 |
| 93 | 0.04 |
| 94 | 0.78 |
| 95 | 0.19 |
| 96 | 0.05 |
| 97 | 0.09 |
| 98 | 0.07 |
| 99 | 0.06 |
| 100 | 0.14 |
| 101 | 0.19 |
| 102 | 0.18 |
| 103 | 0.03 |
| 104 | 0.06 |
| 105 | 0.11 |
| 106 | 0.21 |
| 107 | 0.08 |
| 108 | 0.1 |
| 109 | 0.08 |
| 110 | 0.08 |
| 111 | 0.24 |
| 112 | 0.3 |
| 113 | 0.08 |
| 114 | 0.21 |
| 115 | 0.23 |
| 116 | 0.04 |
| 117 | 0.11 |
| 118 | 0.04 |
| 119 | 0.06 |
| 120 | 0.23 |
| 121 | 0.16 |
| 122 | 0.13 |
| 123 | 0.2 |
| 124 | 0.23 |
| 125 | 0.36 |
| 126 | 0.25 |
| 127 | 0.49 |
| 128 | 0.66 |
| 129 | 0.48 |
| 130 | 0.52 |
| 131 | 0.5 |
| 132 | 0.46 |
| 133 | 0.09 |
| 134 | 0.06 |
| 135 | 0.08 |
| 136 | 0.61 |
| 137 | 0.14 |
| 138 | 0.31 |
| 139 | 0.08 |
| 140 | 0.11 |
| 141 | 0.09 |
| 142 | 0.1 |
| 143 | 0.53 |
| 144 | 0.14 |
| 145 | 0.13 |
| 146 | 0.12 |
| 147 | 0.43 |
| 148 | 0.61 |
| 149 | 0.05 |
| 150 | 0.24 |
| 151 | 0.54 |
| 152 | 0.12 |
| 153 | 0.17 |
| 154 | 0.11 |
| 155 | 0.11 |
| 156 | 0.08 |
| 157 | 0.18 |
| 158 | 0.46 |
| 159 | 0.15 |
| 160 | 0.1 |

Compounds of formula (I) as described above have IC$_{50}$ values between 50 uM and 0.005 uM, preferred compounds have IC$_{50}$ values between 5 uM and 0.01 uM, particularly preferred compounds have IC$_{50}$ values between 0.5 uM and 0.01 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula (I) and their pharmaceutically acceptable salts can be used for the prophylaxis or treatment of diabetes, dyslipidemia, atherosclerosis and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

1-Benzyl-4-hydroxy-piperidine-4-carboxylic acid (4-isopropyl-phenyl)-amide

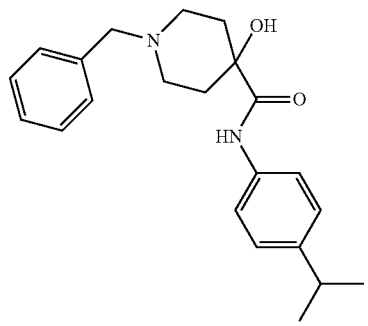 [SMILES: CC(C)c1ccc(NC(=O)C2(O)CCN(Cc3ccccc3)CC2)cc1]

Step 1

8-Benzyl-3-(4-isopropyl-phenyl)-1-oxa-3,8-diaza-spiro[4.5]decane-2,4-dione

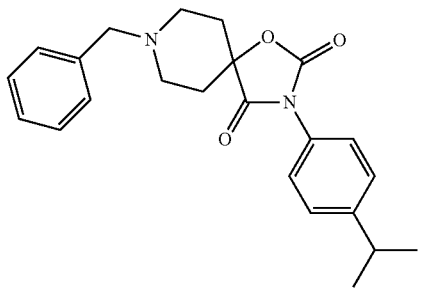 [SMILES: CC(C)c1ccc(N2C(=O)OC3(CCN(Cc4ccccc4)CC3)C2=O)cc1]

A mixture of 1.5 g (6.9 mmol) 1-benzyl-4-hydroxy-piperidine-4-carbonitrile (commercially available), 1.18 g (7.28 mmol) 1,1'-carbonyl-diimidazole, 4.15 mL (29.8 mmol) triethylamine and 0.937 g (6.93 mmol) 4-isopropyl-phenylamine (commercially available) in 10 mL DCM was stirred at room temperature over night. The solvent was removed under reduced pressure and the residue dissolved in 15 mL THF. 8.7 mL HCl conc. was added and the mixture was stirred at room temperature for 5 h. The mixture was evaporated and taken up in methanol and the product precipitated upon addition of water. The precipitate was filtered off, dried and used without further purification in the consecutive step. MS (m/e): 379.2 [(M+H)$^+$].

Step 2

The product from the previous step was dissolved in 10 mL methanol and treated with NaOMe in MeOH at 115° C. in a sealed tubes under MW irradiation for 3×10 min. After cooling, water was added to the mixtures and the precipitate was filtered off, washed with water and dried. The residue was dissolved in DCM and purified over a 5 g silica flash chromatography column eluting with a gradient formed from DCM and methanol to yield after evaporation of the product containing fractions 33 mg (1.4%) of the title compound. MS (m/e): 353.2 [(M+H)$^+$].

Example 2

1-(4-Fluoro-benzyl)-4-hydroxy-piperidine-4-carboxylic acid (4-isopropyl-phenyl)-amide

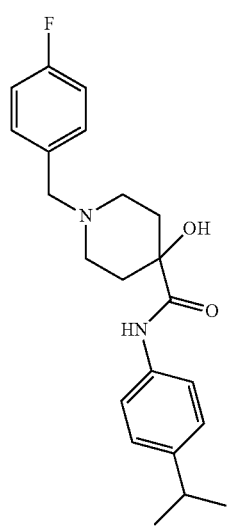 [SMILES: CC(C)c1ccc(NC(=O)C2(O)CCN(Cc3ccc(F)cc3)CC2)cc1]

Step 1

4-Hydroxy-piperidine-4-carboxylic acid (4-isopropyl-phenyl)-amide

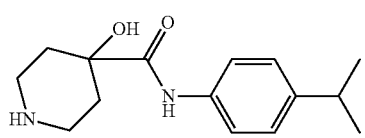 [SMILES: CC(C)c1ccc(NC(=O)C2(O)CCNCC2)cc1]

A mixture of 33 mg (0.09 mmol) 1-benzyl-4-hydroxy-piperidine-4-carboxylic acid (4-isopropyl-phenyl)-amide in 15 mL ethanol and 10 uL acetic acid was hydrogenated over Pd/C with 1 bar H2 for 2 h at room temperature. The mixture was filtered, the catalyst washed with ethanol and the filtrate evaporated to dryness yielding 33 mg (70% purity) of the title compound. MS (m/e): 263.1 [(M+H)$^+$].

Step 2

A mixture of 25.6 mg (0.09 mmol) 4-Hydroxy-piperidine-4-carboxylic acid (4-isopropyl-phenyl)-amide, 19.9 mg (0.1 mmol) 4-fluorobenzyl bromide and 27 mg (0.27 mmol) NEt$_3$ in 2 ml DCM was stirred for 3 h at room temperature. The mixture was concentrated and subjected to purification by preparative HPLC on reversed phase eluting with a gradient formed from acetonitrile, water and NEt$_3$ to yield after evaporation of the product containing fractions 5.4 mg (17%) of the title compound as off-white solid. MS (m/e): 371.3 [(M+H)$^+$].

Example 3

1-Benzyl-4-hydroxy-piperidine-4-carboxylic acid (4-tert-butyl-phenyl)-amide

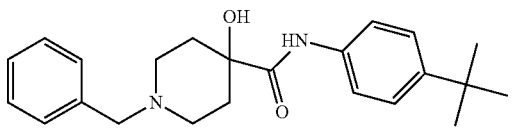 [SMILES: CC(C)(C)c1ccc(NC(=O)C2(O)CCN(Cc3ccccc3)CC2)cc1]

In analogy to the procedure described for the synthesis of 1-benzyl-4-hydroxy-piperidine-4-carboxylic acid (4-isopropyl-phenyl)-amide (example 1) the title compound was prepared from 1-benzyl-4-hydroxy-piperidine-4-carbonitrile (commercially available) and 4-tert.-butyl-phenylamine. MS (m/e): 367.2 [(M+H)$^+$].

Intermediate 1

4-Hydroxy-piperidine-4-carboxylic acid (4-trifluoromethoxy-phenyl)-amide

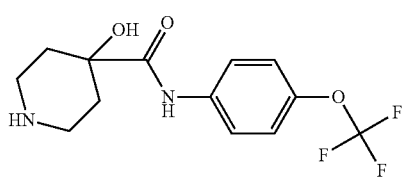 [SMILES: O=C(Nc1ccc(OC(F)(F)F)cc1)C1(O)CCNCC1]

In analogy to the procedure described for the synthesis of 4-hydroxy-piperidine-4-carboxylic acid (4-isopropyl-phenyl)-amide (example 2, step 1) the title compound was prepared from 1-benzyl-4-hydroxy-piperidine-4-carboxylic acid (4-trifluoromethoxy-phenyl)-amide (preparation in analogy to 1-benzyl-4-hydroxy-piperidine-4-carboxylic acid (4-isopropyl-phenyl)-amide (example 1) from 1-benzyl-4-hydroxy-piperidine-4-carbonitrile (commercially available) and 4-trifluoromethoxy-phenylamine). MS (m/e): 305.1[(M+H)$^+$].

Intermediate 2

4-Hydroxy-piperidine-4-carboxylic acid (4-isopropoxy-phenyl)-amide

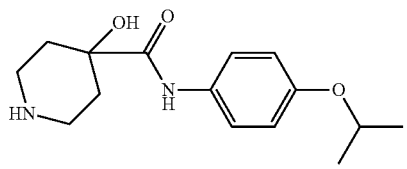 [SMILES: CC(C)Oc1ccc(NC(=O)C2(O)CCNCC2)cc1]

In analogy to the procedure described for the synthesis of 4-hydroxy-piperidine-4-carboxylic acid (4-isopropyl-phenyl)-amide (example 2, step 1) the title compound was prepared from 1-Benzyl-4-hydroxy-piperidine-4-carboxylic acid (4-isopropoxy-phenyl)-amide (preparation in analogy to 1-benzyl-4-hydroxy-piperidine-4-carboxylic acid (4-isopropyl-phenyl)-amide (example 1) from 1-benzyl-4-hydroxy-piperidine-4-carbonitrile (commercially available) and 4-isopropoxy-phenylamine). MS (m/e): 279.1[(M+H)$^+$].

Intermediate 3

4-Hydroxy-piperidine-4-carboxylic acid (4-tert-butyl-phenyl)-amide

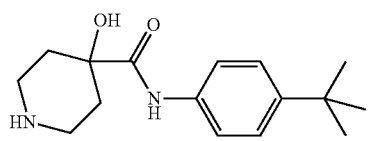

In analogy to the procedure described for the synthesis of 4-hydroxy-piperidine-4-carboxylic acid (4-isopropyl-phenyl)-amide (example 2, step 1) the title compound was prepared from 1-benzyl-4-hydroxy-piperidine-4-carboxylic acid (4-tert-butyl-phenyl)-amide (example 3). MS (m/e): 277.2[(M+H)$^+$].

Intermediate 4

4-Hydroxy-piperidine-4-carboxylic acid methyl-(4-trifluoromethoxy-phenyl)-amide

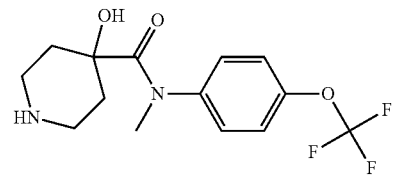 [SMILES: CN(C(=O)C1(O)CCNCC1)c1ccc(OC(F)(F)F)cc1]

Step 1

1-Benzyl-4-hydroxy-piperidine-4-carboxylic acid, hydrochloride

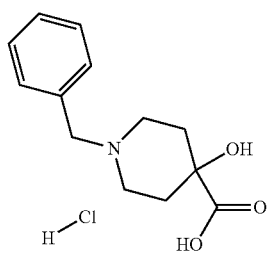

A mixture of 8 g (32 mmol) 1-benzyl-4-cyano-4-hydroxypiperidine hydrochloride and 15.8 mL HCl (37%) was heated to reflux for 16 h. The solution was cooled to room temperature and the white precipitate was filtered off and washed with iso-propanol. The filtrate was evaporated to yield 9.71 g (96%) of the title compound as white waxy solid which was used without further purification. MS (m/e): 234.4 [(MH)-].

Step 2

4-Acetoxy-1-benzyl-piperidine-4-carboxylic acid

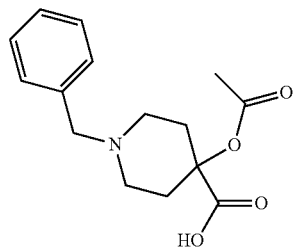 [SMILES: CC(=O)OC1(C(=O)O)CCN(Cc2ccccc2)CC1]

A mixture of 9.4 g 1-benzyl-4-hydroxy-piperidine-4-carboxylic acid, hydrochloride, 3.62 g (35 mmol) acetic anhydride, 11.89 mL pyridine in 40 mL DCM was stirred for 1 h at room temperature. KHSO$_4$ (10%) and ethanol were added and filtered. The filtrate was evaporated and the residue was purified by preparative HPLC on reversed phase eluting with a gradient formed from acetonitrile, water and HCOOH. The product containing fractions were evaporated to yield 4.2 g (52%) of the title compound as light yellow solid. MS (m/e): 278.1 [(M+H)$^+$].

Step 3

Acetic acid 1-benzyl-4-[methyl-(4-trifluoromethoxy-phenyl)-carbamoyl]-piperidin-4-yl ester

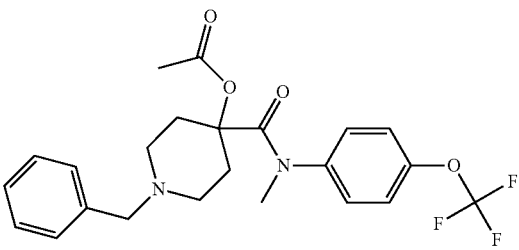 [SMILES: CC(=O)OC1(C(=O)N(C)c2ccc(OC(F)(F)F)cc2)CCN(Cc2ccccc2)CC1]

A mixture of 1.4 g (5 mmol) 4-acetoxy-1-benzyl-piperidine-4-carboxylic acid 0.49 mL (5.8 mmol) oxalylchloride, cat. amount DMF and 2.1 mL (15 mmol) NEt$_3$ in DCM at 0° C. was stirred for 1 h. The mixture was concentrated and to 0.79 g (2.42 mmol) of the acid chloride and 2.1 mL (12.1 mmol) DIPEA in 25 mL DCM was added 0.554 g (2.9 mmol) methyl-(4-trifluoromethoxy-phenyl)-amine. The mixture was stirred for 15 h at room temperature. KHSO$_4$ (1N) was added and the mixture was extracted with DCM. The combined organic extracts were dried with MgSO$_4$ and evaporated. 0.782 g (72%) of the title compounds as obtained. MS (m/e): 451.3 [(M+H)$^+$].

Step 4

1-Benzyl-4-hydroxy-piperidine-4-carboxylic acid methyl-(4-trifluoromethoxy-phenyl)-amide

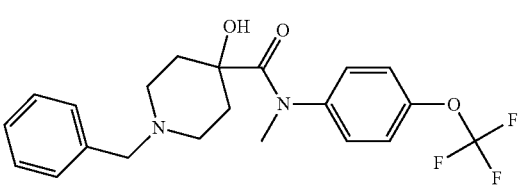 [SMILES: CN(C(=O)C1(O)CCN(Cc2ccccc2)CC1)c1ccc(OC(F)(F)F)cc1]

A mixture of 0.782 g (1.7 mmol) acetic acid 1-benzyl-4-[methyl-(4-trifluoromethoxy-phenyl)-carbamoyl]-piperidin-4-yl ester and excess KOH 5M was heated to 70° C. The mixture was diluted with KHSO$_4$ 1N aq. and extracted with ethyl acetate. the combined organic fractions were dried with MgSO$_4$ and evaporated. The residue was purified by preparative HPLC on reversed phase eluting with a gradient formed from acetonitrile, water and HCOOH. The product containing fractions were evaporated to yield 0.41 g (58%) of the title compound. MS (m/e): 409.1 [(M+H)$^+$].

Step 5

4-Hydroxy-piperidine-4-carboxylic acid methyl-(4-trifluoromethoxy-phenyl)-amide In analogy to the procedure described for the synthesis of 4-hydroxy-piperidine-4-carboxylic acid (4-isopropyl-phenyl)-amide (example 2, step 1) the title compound was prepared from 1-benzyl-4-hydroxy-piperidine-4-carboxylic acid methyl-(4-trifluoromethoxy-phenyl)-amide (example 3). MS (m/e): 319.2[(M+H)$^+$].

Intermediate 5

4-Hydroxy-piperidine-4-carboxylic acid ethyl-(4-trifluoromethoxy-phenyl)-amide

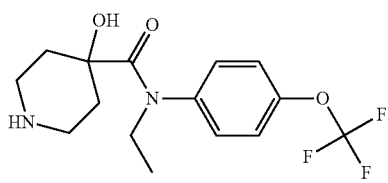 [SMILES: CCN(C(=O)C1(O)CCNCC1)c1ccc(OC(F)(F)F)cc1]

In analogy to the procedure described for the synthesis of 4-hydroxy-piperidine-4-carboxylic acid methyl-(4-trifluoromethoxy-phenyl)-amide (intermediate 4) the title compound was prepared from 4-acetoxy-1-benzyl-piperidine-4-carboxylic acid and ethyl-(4-trifluoromethoxy-phenyl)-amine. MS (m/e): 333.1 [(M+H)$^+$].

In analogy to the procedure described for the synthesis of 1-benzyl-4-hydroxy-piperidine-4-carboxylic acid (4-isopropyl-phenyl)-amide (example 1) examples 4 to 75 have been synthesized from their respective starting materials as mentioned in table 1.

TABLE 1

| Ex | Structure | Chemical name MS (m/e) [(M + H)+] | Starting material |
|---|---|---|---|
| 4 | 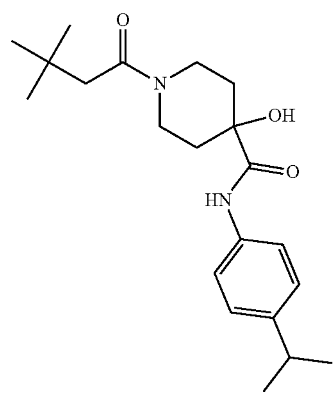 [SMILES: CC(C)c1ccc(NC(=O)C2(O)CCN(C(=O)CC(C)(C)C)CC2)cc1] | 1-(3,3-Dimethyl-butyryl)-4-hydroxy-piperidine-4-carboxylic acid (4-isopropyl-phenyl)-amide 361.3 | 4-Hydroxy-piperidine-4-carboxylic acid (4-isopropyl-phenyl)-amide and tert.-butyl-acetyl chloride (commercially available) |
| 5 | 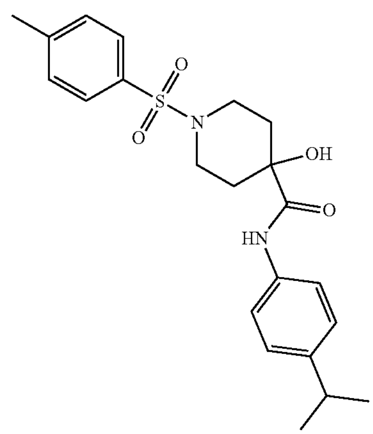 [SMILES: Cc1ccc(S(=O)(=O)N2CCC(O)(C(=O)Nc3ccc(C(C)C)cc3)CC2)cc1] | 4-Hydroxy-1-(toluene-4-sulfonyl)-piperidine-4-carboxylic acid (4-isopropyl-phenyl)-amide 417.3 | 4-Hydroxy-piperidine-4-carboxylic acid (4-isopropyl-phenyl)-amide and p-toluenesulfonic-acid chloride (commercially available) |
| 6 | 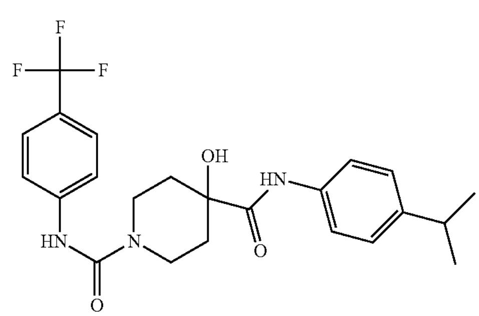 [SMILES: CC(C)c1ccc(NC(=O)C2(O)CCN(C(=O)Nc3ccc(C(F)(F)F)cc3)CC2)cc1] | 4-Hydroxy-piperidine-1,4-dicarboxylic acid 4-[(4-isopropyl-phenyl)-amide] 1-[(4-trifluoromethyl-phenyl)-amide] 450.2 | 4-Hydroxy-piperidine-4-carboxylic acid (4-isopropyl-phenyl)-amide and 1-Isocyanato-4-trifluoromethyl-benzene (commercially available) |

TABLE 1-continued

| Ex | Structure | Chemical name MS (m/e) [(M + H)+] | Starting material |
|---|---|---|---|
| 7 | 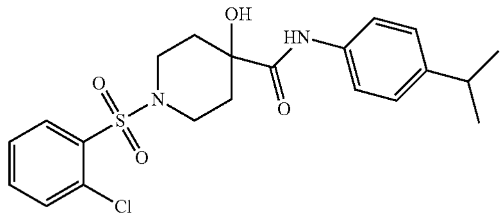 [SMILES: CC(C)c1ccc(NC(=O)C2(O)CCN(S(=O)(=O)c3ccccc3Cl)CC2)cc1] | 1-(2-Chloro-benzenesulfonyl)-4-hydroxy-piperidine-4-carboxylic acid (4-isopropyl-phenyl)-amide 437.2 | 4-Hydroxy-piperidine-4-carboxylic acid (4-isopropyl-phenyl)-amide and 2-Chloro-benzenesulfonyl chloride (commercially available) |
| 8 | 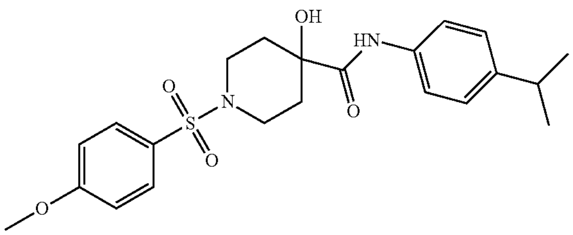 [SMILES: COc1ccc(S(=O)(=O)N2CCC(O)(C(=O)Nc3ccc(C(C)C)cc3)CC2)cc1] | 4-Hydroxy-1-(4-methoxy-benzenesulfonyl)-piperidine-4-carboxylic acid (4-isopropyl-phenyl)-amide 433.2 | 4-Hydroxy-piperidine-4-carboxylic acid (4-isopropyl-phenyl)-amide and 4-Methoxy-benzenesulfonyl chloride (commercially available) |
| 9 | 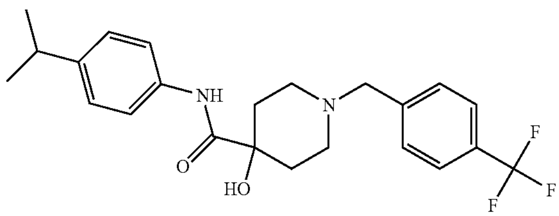 [SMILES: CC(C)c1ccc(NC(=O)C2(O)CCN(Cc3ccc(C(F)(F)F)cc3)CC2)cc1] | 4-Hydroxy-1-(4-trifluoromethyl-benzyl)-piperidine-4-carboxylic acid (4-isopropyl-phenyl)-amide 421.3 | 4-Hydroxy-piperidine-4-carboxylic acid (4-isopropyl-phenyl)-amide and 1-Bromomethyl-4-trifluoromethyl-benzene (commercially available) |
| 10 | 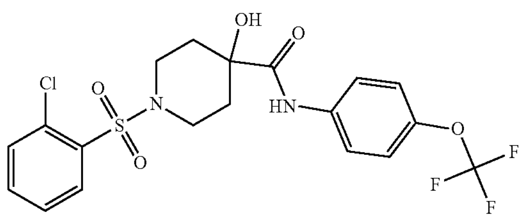 [SMILES: O=C(Nc1ccc(OC(F)(F)F)cc1)C1(O)CCN(S(=O)(=O)c2ccccc2Cl)CC1] | 1-(2-Chloro-benzenesulfonyl)-4-hydroxy-piperidine-4-carboxylic acid (4-trifluoromethoxy-phenyl)-amide 479.2 | 4-Hydroxy-piperidine-4-carboxylic acid (4-trifluoromethoxy-phenyl)-amide (intermediate 1) and 2-Chloro-benzenesulfonyl chloride (commercially available) |
| 11 | 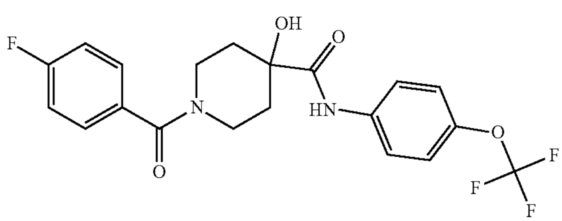 [SMILES: O=C(c1ccc(F)cc1)N1CCC(O)(C(=O)Nc2ccc(OC(F)(F)F)cc2)CC1] | 1-(4-Fluoro-benzoyl)-4-hydroxy-piperidine-4-carboxylic acid (4-trifluoromethoxy-phenyl)-amide 427.2 | 4-Hydroxy-piperidine-4-carboxylic acid (4-trifluoromethoxy-phenyl)-amide (intermediate 1) and 4-Fluoro-benzoyl chloride (commercially available) |
| 12 | 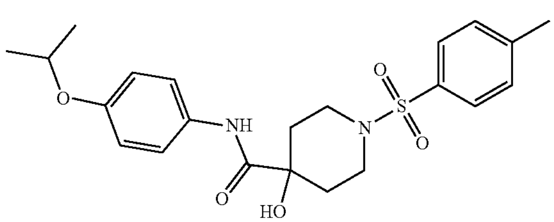 [SMILES: Cc1ccc(S(=O)(=O)N2CCC(O)(C(=O)Nc3ccc(OC(C)C)cc3)CC2)cc1] | 4-Hydroxy-1-(toluene-4-sulfonyl)-piperidine-4-carboxylic acid (4-isopropoxy-phenyl)-amide 433.2 | 4-Hydroxy-piperidine-4-carboxylic acid (4-isopropoxy-phenyl)-amide (intermediate 2) and 4-Methyl-benzenesulfonyl chloride (commercially available) |

TABLE 1-continued

| Ex | Structure | Chemical name MS (m/e) [(M + H)+] | Starting material |
|---|---|---|---|
| 13 | 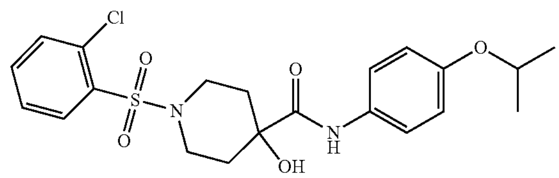 [SMILES: CC(C)Oc1ccc(NC(=O)C2(O)CCN(S(=O)(=O)c3ccccc3Cl)CC2)cc1] | 1-(2-Chloro-benzenesulfonyl)-4-hydroxy-piperidine-4-carboxylic acid (4-isopropoxy-phenyl)-amide 453.2 | 4-Hydroxy-piperidine-4-carboxylic acid (4-isopropoxy-phenyl)-amide (intermediate 2) and 2-Chloro-benzenesulfonyl chloride (commercially available) |
| 14 | 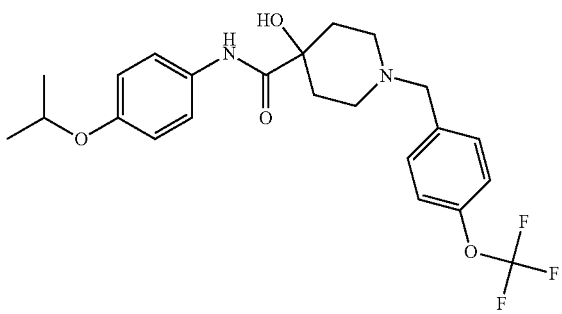 [SMILES: CC(C)Oc1ccc(NC(=O)C2(O)CCN(Cc3ccc(OC(F)(F)F)cc3)CC2)cc1] | 4-Hydroxy-1-(4-trifluoromethoxy-benzyl)-piperidine-4-carboxylic acid (4-isopropoxy-phenyl)-amide 453.3 | 4-Hydroxy-piperidine-4-carboxylic acid (4-isopropoxy-phenyl)-amide (intermediate 2) and 1-Bromomethyl-4-trifluoromethoxy-benzene (commercially available) |
| 15 | 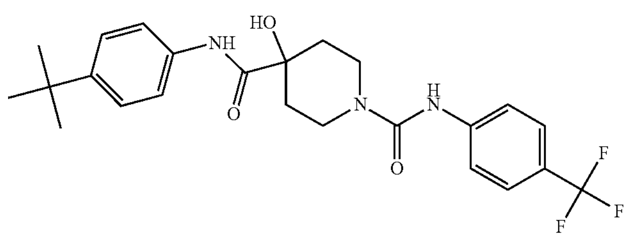 [SMILES: CC(C)(C)c1ccc(NC(=O)C2(O)CCN(C(=O)Nc3ccc(C(F)(F)F)cc3)CC2)cc1] | 4-Hydroxy-piperidine-1,4-dicarboxylic acid 4-[(4-tert-butyl-phenyl)-amide] 1-[(4-trifluoromethyl-phenyl)-amide] 464.3 | 4-Hydroxy-piperidine-4-carboxylic acid (4-tert-butyl-phenyl)-amide (intermediate 3) and 1-Isocyanato-4-trifluoromethyl-benzene (commercially available) |
| 16 | 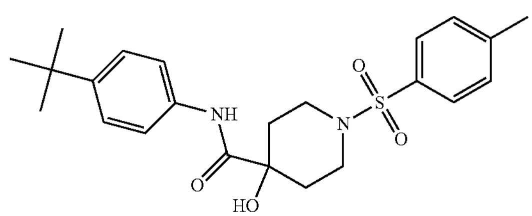 [SMILES: Cc1ccc(S(=O)(=O)N2CCC(O)(C(=O)Nc3ccc(C(C)(C)C)cc3)CC2)cc1] | 4-Hydroxy-1-(toluene-4-sulfonyl)-piperidine-4-carboxylic acid (4-tert-butyl-phenyl)-amide 431.3 | 4-Hydroxy-piperidine-4-carboxylic acid (4-tert-butyl-phenyl)-amide (intermediate 3) and 4-Methyl-benzenesulfonyl chloride (commercially available) |
| 17 | 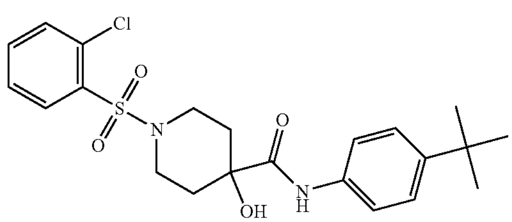 [SMILES: CC(C)(C)c1ccc(NC(=O)C2(O)CCN(S(=O)(=O)c3ccccc3Cl)CC2)cc1] | 1-(2-Chloro-benzenesulfonyl)-4-hydroxy-piperidine-4-carboxylic acid (4-tert-butyl-phenyl)-amide 451.2 | 4-Hydroxy-piperidine-4-carboxylic acid (4-tert-butyl-phenyl)-amide (intermediate 3) and 2-Chloro-benzenesulfonyl chloride (commercially available) |
| 18 | 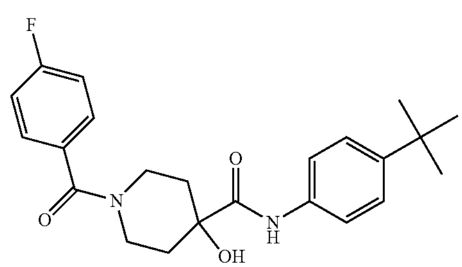 [SMILES: CC(C)(C)c1ccc(NC(=O)C2(O)CCN(C(=O)c3ccc(F)cc3)CC2)cc1] | 1-(4-Fluoro-benzoyl)-4-hydroxy-piperidine-4-carboxylic acid (4-tert-butyl-phenyl)-amide 399.3 | 4-Hydroxy-piperidine-4-carboxylic acid (4-tert-butyl-phenyl)-amide (intermediate 3) and 4-Fluoro-benzoyl chloride (commercially available) |

TABLE 1-continued

| Ex | Structure | Chemical name MS (m/e) [(M + H)+] | Starting material |
|---|---|---|---|
| 19 | 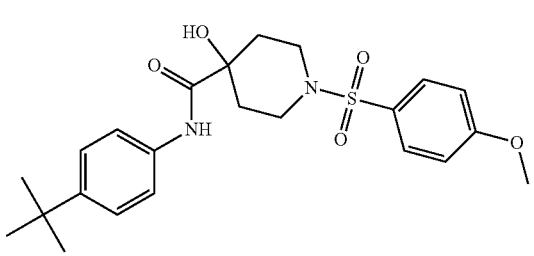 [SMILES: COc1ccc(S(=O)(=O)N2CCC(O)(C(=O)Nc3ccc(C(C)(C)C)cc3)CC2)cc1] | 4-Hydroxy-1-(4-methoxy-benzenesulfonyl)-piperidine-4-carboxylic acid (4-tert-butyl-phenyl)-amide 447.2 | 4-Hydroxy-piperidine-4-carboxylic acid (4-tert-butyl-phenyl)-amide (intermediate 3) and 4-Methoxy-benzenesulfonyl chloride (commercially available) |
| 20 | 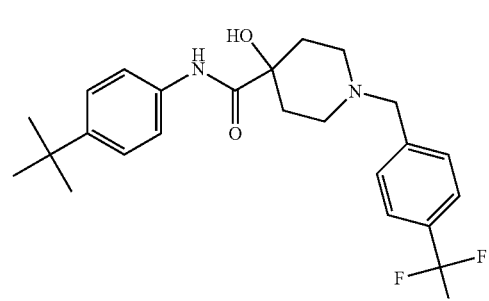 | 4-Hydroxy-1-(4-trifluoromethyl-benzyl)-piperidine-4-carboxylic acid (4-tert-butyl-phenyl)-amide 435.3 | 4-Hydroxy-piperidine-4-carboxylic acid (4-tert-butyl-phenyl)-amide (intermediate 3) and 1-Bromomethyl-4-trifluoromethyl-benzene (commercially available) |
| 21 | 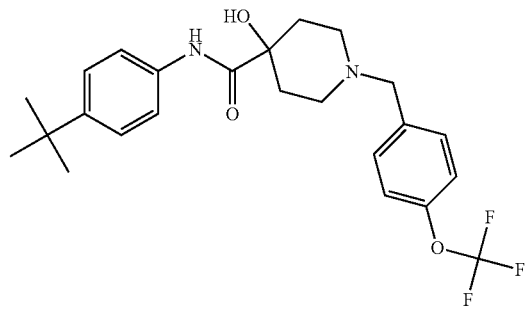 [SMILES: CC(C)(C)c1ccc(NC(=O)C2(O)CCN(Cc3ccc(OC(F)(F)F)cc3)CC2)cc1] | 4-Hydroxy-1-(4-trifluoromethoxy-benzyl)-piperidine-4-carboxylic acid (4-tert-butyl-phenyl)-amide 451.3 | 4-Hydroxy-piperidine-4-carboxylic acid (4-tert-butyl-phenyl)-amide (intermediate 3) and 1-Bromomethyl-4-trifluoromethoxy-benzene (commercially available) |
| 22 | 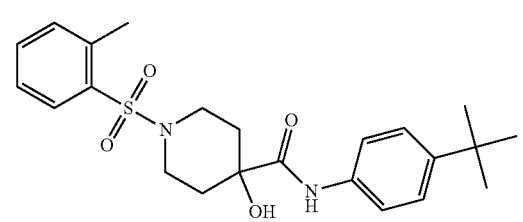 [SMILES: Cc1ccccc1S(=O)(=O)N1CCC(O)(C(=O)Nc2ccc(C(C)(C)C)cc2)CC1] | 4-Hydroxy-1-(toluene-2-sulfonyl)-piperidine-4-carboxylic acid (4-tert-butyl-phenyl)-amide 431.2 | 4-Hydroxy-piperidine-4-carboxylic acid (4-tert-butyl-phenyl)-amide (intermediate 3) and 2-Chloro-benzenesulfonyl chloride (commercially available) |
| 23 | 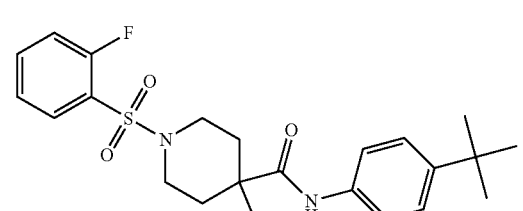 | 1-(2-Fluoro-benzenesulfonyl)-4-hydroxy-piperidine-4-carboxylic acid (4-tert-butyl-phenyl)-amide 435.2 | 4-Hydroxy-piperidine-4-carboxylic acid (4-tert-butyl-phenyl)-amide (intermediate 3) and 2-Fluoro-benzenesulfonyl chloride (commercially available) |

TABLE 1-continued

| Ex | Structure | Chemical name MS (m/e) [(M + H)+] | Starting material |
|---|---|---|---|
| 24 | 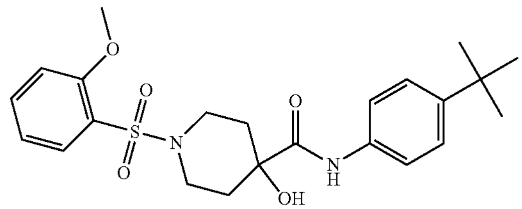 [SMILES: COc1ccccc1S(=O)(=O)N1CCC(O)(C(=O)Nc2ccc(C(C)(C)C)cc2)CC1] | 4-Hydroxy-1-(2-methoxy-benzenesulfonyl)-piperidine-4-carboxylic acid (4-tert-butyl-phenyl)-amide 447.2 | 4-Hydroxy-piperidine-4-carboxylic acid (4-tert-butyl-phenyl)-amide (intermediate 3) and 2-Methoxy-benzenesulfonyl chloride (commercially available) |
| 25 | 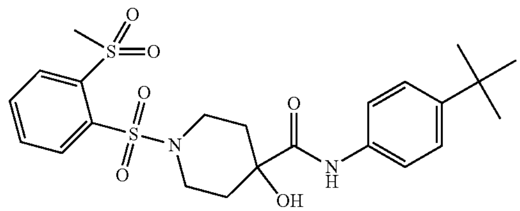 [SMILES: CC(C)(C)c1ccc(NC(=O)C2(O)CCN(S(=O)(=O)c3ccccc3S(C)(=O)=O)CC2)cc1] | 4-Hydroxy-1-(2-methanesulfonyl-benzenesulfonyl)-piperidine-4-carboxylic acid (4-tert-butyl-phenyl)-amide 495.2 | 4-Hydroxy-piperidine-4-carboxylic acid (4-tert-butyl-phenyl)-amide (intermediate 3) and 2-Methanesulfonyl-benzenesulfonyl chloride (commercially available) |
| 26 | 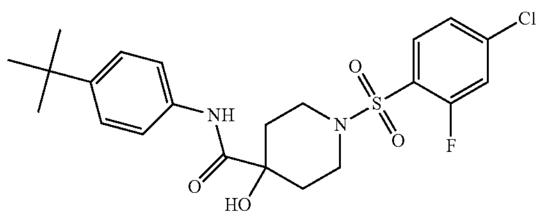 [SMILES: CC(C)(C)c1ccc(NC(=O)C2(O)CCN(S(=O)(=O)c3ccc(Cl)cc3F)CC2)cc1] | 1-(4-Chloro-2-fluoro-benzenesulfonyl)-4-hydroxy-piperidine-4-carboxylic acid (4-tert-butyl-phenyl)-amide 469.1 | 4-Hydroxy-piperidine-4-carboxylic acid (4-tert-butyl-phenyl)-amide (intermediate 3) and 4-Chloro-2-fluoro-benzenesulfonyl chloride (commercially available) |
| 27 | 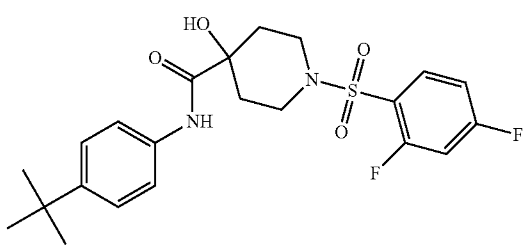 [SMILES: CC(C)(C)c1ccc(NC(=O)C2(O)CCN(S(=O)(=O)c3ccc(F)cc3F)CC2)cc1] | 1-(2,4-Difluoro-benzenesulfonyl)-4-hydroxy-piperidine-4-carboxylic acid (4-tert-butyl-phenyl)-amide 453.3 | 4-Hydroxy-piperidine-4-carboxylic acid (4-tert-butyl-phenyl)-amide (intermediate 3) and 2,4-Difluoro-benzenesulfonyl chloride (commercially available) |
| 28 | 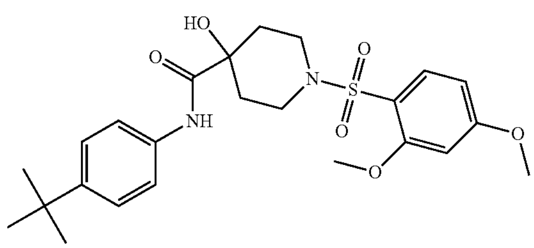 [SMILES: COc1ccc(S(=O)(=O)N2CCC(O)(C(=O)Nc3ccc(C(C)(C)C)cc3)CC2)c(OC)c1] | 1-(2,4-Dimethoxy-benzenesulfonyl)-4-hydroxy-piperidine-4-carboxylic acid (4-tert-butyl-phenyl)-amide 477.2 | 4-Hydroxy-piperidine-4-carboxylic acid (4-tert-butyl-phenyl)-amide (intermediate 3) and 2,4-Dimethoxy-benzenesulfonyl chloride (commercially available) |
| 29 | 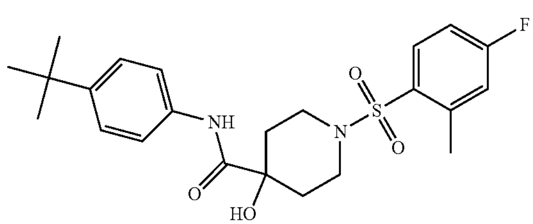 [SMILES: Cc1cc(F)ccc1S(=O)(=O)N1CCC(O)(C(=O)Nc2ccc(C(C)(C)C)cc2)CC1] | 1-(4-Fluoro-2-methyl-benzenesulfonyl)-4-hydroxy-piperidine-4-carboxylic acid (4-tert-butyl-phenyl)-amide 449.2 | 4-Hydroxy-piperidine-4-carboxylic acid (4-tert-butyl-phenyl)-amide (intermediate 3) and 4-Fluoro-2-methyl-benzenesulfonyl chloride (commercially available) |

TABLE 1-continued

| Ex | Structure | Chemical name MS (m/e) [(M + H)+] | Starting material |
|---|---|---|---|
| 30 | 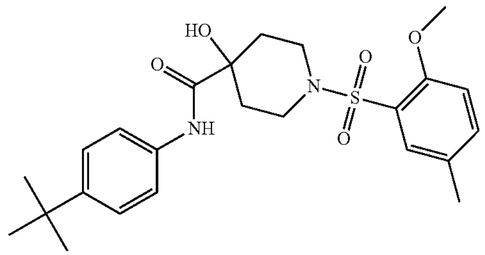 [SMILES: COc1ccc(C)cc1S(=O)(=O)N1CCC(O)(C(=O)Nc2ccc(C(C)(C)C)cc2)CC1] | 4-Hydroxy-1-(2-methoxy-5-methyl-benzenesulfonyl)-piperidine-4-carboxylic acid (4-tert-butyl-phenyl)-amide 461.2 | 4-Hydroxy-piperidine-4-carboxylic acid (4-tert-butyl-phenyl)-amide (intermediate 3) and 2-Methoxy-5-methyl-benzenesulfonyl chloride (commercially available) |
| 31 | 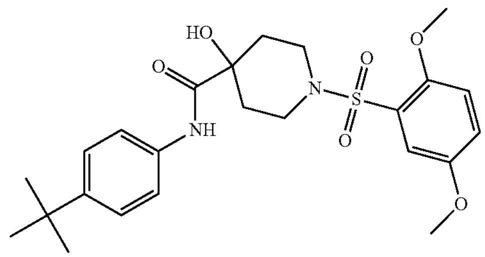 [SMILES: COc1ccc(OC)c(S(=O)(=O)N2CCC(O)(C(=O)Nc3ccc(C(C)(C)C)cc3)CC2)c1] | 1-(2,5-Dimethoxy-benzenesulfonyl)-4-hydroxy-piperidine-4-carboxylic acid (4-tert-butyl-phenyl)-amide 477.2 | 4-Hydroxy-piperidine-4-carboxylic acid (4-tert-butyl-phenyl)-amide (intermediate 3) and 2,5-Dimethoxy-benzenesulfonyl chloride (commercially available) |
| 32 | 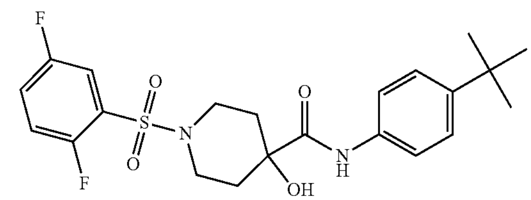 [SMILES: CC(C)(C)c1ccc(NC(=O)C2(O)CCN(S(=O)(=O)c3cc(F)ccc3F)CC2)cc1] | 1-(2,5-Difluoro-benzenesulfonyl)-4-hydroxy-piperidine-4-carboxylic acid (4-tert-butyl-phenyl)-amide 453.2 | 4-Hydroxy-piperidine-4-carboxylic acid (4-tert-butyl-phenyl)-amide (intermediate 3) and 2,5-Difluoro-benzenesulfonyl chloride (commercially available) |
| 33 | 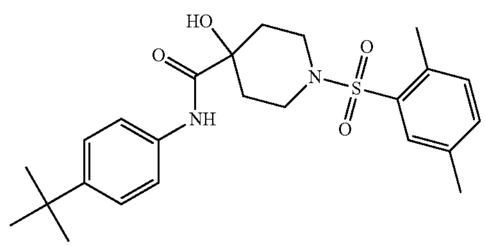 [SMILES: Cc1ccc(C)c(S(=O)(=O)N2CCC(O)(C(=O)Nc3ccc(C(C)(C)C)cc3)CC2)c1] | 1-(2,5-Dimethyl-benzenesulfonyl)-4-hydroxy-piperidine-4-carboxylic acid (4-tert-butyl-phenyl)-amide 445.2 | 4-Hydroxy-piperidine-4-carboxylic acid (4-tert-butyl-phenyl)-amide (intermediate 3) and 2,5-Dimethyl-benzenesulfonyl chloride (commercially available) |
| 34 | 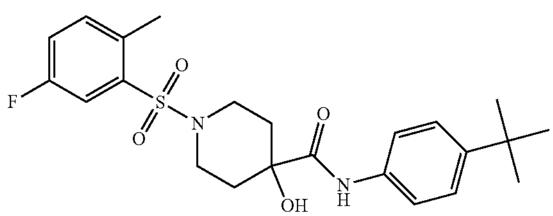 [SMILES: Cc1ccc(F)cc1S(=O)(=O)N1CCC(O)(C(=O)Nc2ccc(C(C)(C)C)cc2)CC1] | 1-(5-Fluoro-2-methyl-benzenesulfonyl)-4-hydroxy-piperidine-4-carboxylic acid (4-tert-butyl-phenyl)-amide 449.2 | 4-Hydroxy-piperidine-4-carboxylic acid (4-tert-butyl-phenyl)-amide (intermediate 3) and 5-Fluoro-2-methyl-benzenesulfonyl chloride (commercially available) |
| 35 | 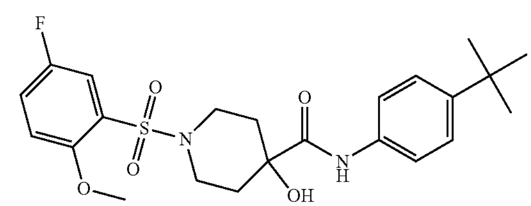 [SMILES: COc1ccc(F)cc1S(=O)(=O)N1CCC(O)(C(=O)Nc2ccc(C(C)(C)C)cc2)CC1] | 1-(5-Fluoro-2-methoxy-benzenesulfonyl)-4-hydroxy-piperidine-4-carboxylic acid (4-tert-butyl-phenyl)-amide 465.2 | 4-Hydroxy-piperidine-4-carboxylic acid (4-tert-butyl-phenyl)-amide (intermediate 3) and 5-Fluoro-2-methoxy-benzenesulfonyl chloride (commercialy available) |

TABLE 1-continued

| Ex | Structure | Chemical name MS (m/e) [(M + H)+] | Starting material |
|---|---|---|---|
| 36 | 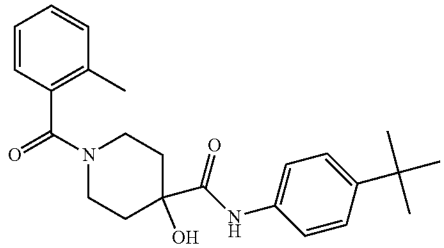 | 4-Hydroxy-1-(2-methyl-benzoyl)-piperidine-4-carboxylic acid (4-tert-butyl-phenyl)-amide 395.2 | 4-Hydroxy-piperidine-4-carboxylic acid (4-tert-butyl-phenyl)-amide (intermediate 3) and 2-Methyl-benzoyl chloride (commercially available) |
| 37 | 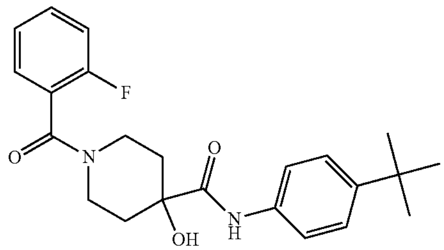 [SMILES: CC(C)(C)c1ccc(NC(=O)C2(O)CCN(C(=O)c3ccccc3F)CC2)cc1] | 1-(2-Fluoro-benzoyl)-4-hydroxy-piperidine-4-carboxylic acid (4-tert-butyl-phenyl)-amide 399.2 | 4-Hydroxy-piperidine-4-carboxylic acid (4-tert-butyl-phenyl)-amide (intermediate 3) and 2-Fluoro-benzoyl chloride (commercially available) |
| 38 | 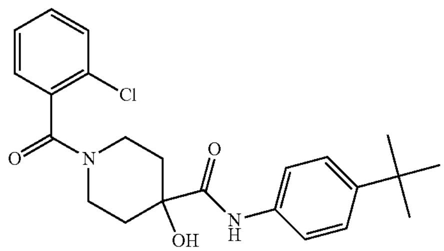 [SMILES: CC(C)(C)c1ccc(NC(=O)C2(O)CCN(C(=O)c3ccccc3Cl)CC2)cc1] | 1-(2-Chloro-benzoyl)-4-hydroxy-piperidine-4-carboxylic acid (4-tert-butyl-phenyl)-amide 415.1 | 4-Hydroxy-piperidine-4-carboxylic acid (4-tert-butyl-phenyl)-amide (intermediate 3) and 2-Chloro-benzoyl chloride (commercially available) |
| 39 | 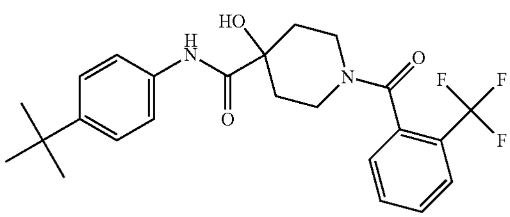 [SMILES: CC(C)(C)c1ccc(NC(=O)C2(O)CCN(C(=O)c3ccccc3C(F)(F)F)CC2)cc1] | 4-Hydroxy-1-(2-trifluoromethyl-benzoyl)-piperidine-4-carboxylic acid (4-tert-butyl-phenyl)-amide 449.2 | 4-Hydroxy-piperidine-4-carboxylic acid (4-tert-butyl-phenyl)-amide (intermediate 3) and 2-Trifluoromethyl-benzoyl chloride (commercially available) |
| 40 | 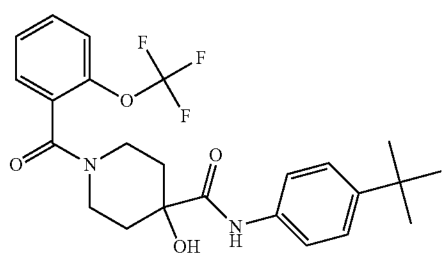 [SMILES: CC(C)(C)c1ccc(NC(=O)C2(O)CCN(C(=O)c3ccccc3OC(F)(F)F)CC2)cc1] | 4-Hydroxy-1-(2-trifluoromethoxy-benzoyl)-piperidine-4-carboxylic acid (4-tert-butyl-phenyl)-amide 465.2 | 4-Hydroxy-piperidine-4-carboxylic acid (4-tert-butyl-phenyl)-amide (intermediate 3) and 2-Trifluoromethoxy-benzoyl chloride (commerciallky available) |
| 41 | 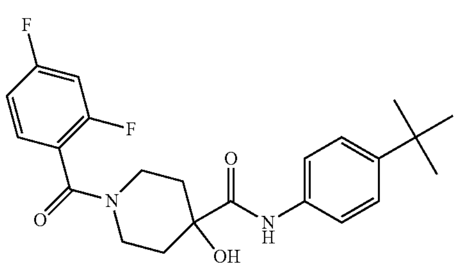 [SMILES: CC(C)(C)c1ccc(NC(=O)C2(O)CCN(C(=O)c3ccc(F)cc3F)CC2)cc1] | 1-(2,4-Difluoro-benzoyl)-4-hydroxy-piperidine-4-carboxylic acid (4-tert-butyl-phenyl)-amide 417.1 | 4-Hydroxy-piperidine-4-carboxylic acid (4-tert-butyl-phenyl)-amide (intermediate 3) and 2,4-Difluoro-benzoyl chloride (commercially available) |

TABLE 1-continued

| Ex | Structure | Chemical name MS (m/e) [(M + H)+] | Starting material |
|---|---|---|---|
| 42 | 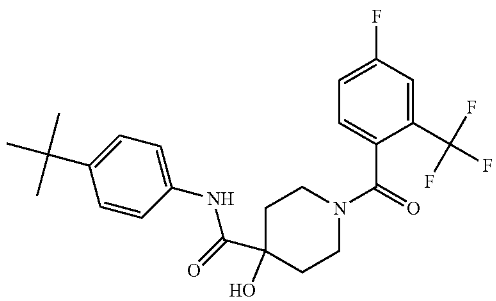 [SMILES: CC(C)(C)c1ccc(NC(=O)C2(O)CCN(C(=O)c3ccc(F)cc3C(F)(F)F)CC2)cc1] | 1-(4-Fluoro-2-trifluoromethyl-benzoyl)-4-hydroxy-piperidine-4-carboxylic acid (4-tert-butyl-phenyl)-amide 467.2 | 4-Hydroxy-piperidine-4-carboxylic acid (4-tert-butyl-phenyl)-amide (intermediate 3) and 4-Fluoro-2-trifluoromethyl-benzoyl chloride (commercially available) |
| 43 | 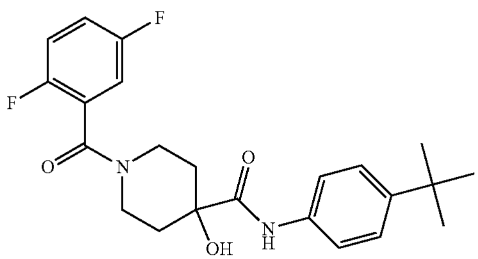 [SMILES: CC(C)(C)c1ccc(NC(=O)C2(O)CCN(C(=O)c3cc(F)ccc3F)CC2)cc1] | 1-(2,5-Difluoro-benzoyl)-4-hydroxy-piperidine-4-carboxylic acid (4-tert-butyl-phenyl)-amide 417.2 | 4-Hydroxy-piperidine-4-carboxylic acid (4-tert-butyl-phenyl)-amide (intermediate 3) and 2,5-Difluoro-benzoyl chloride (commercially available) |
| 44 | 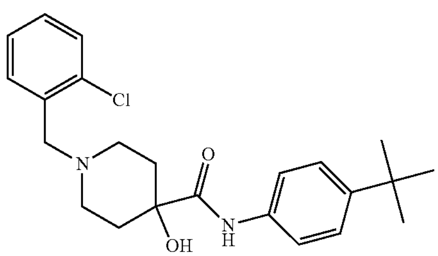 [SMILES: CC(C)(C)c1ccc(NC(=O)C2(O)CCN(Cc3ccccc3Cl)CC2)cc1] | 1-(2-Chloro-benzoyl)-4-hydroxy-piperidine-4-carboxylic acid (4-tert-butyl-phenyl)-amide 401.2 | 4-Hydroxy-piperidine-4-carboxylic acid (4-tert-butyl-phenyl)-amide (intermediate 3) and 1-Bromomethyl-2-chloro-benzene (commercially available) |
| 45 | 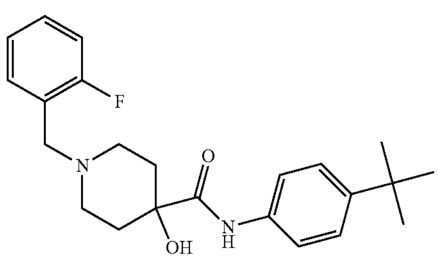 | 1-(2-Fluoro-benzyl)-4-hydroxy-piperidine-4-carboxylic acid (4-tert-butyl-phenyl)-amide 385.2 | 4-Hydroxy-piperidine-4-carboxylic acid (4-tert-butyl-phenyl)-amide (intermediate 3) and 1-Bromomethyl-2-fluoro-benzene (commercially available) |
| 46 | 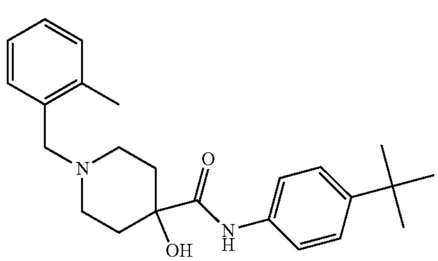 [SMILES: Cc1ccccc1CN1CCC(O)(C(=O)Nc2ccc(C(C)(C)C)cc2)CC1] | 4-Hydroxy-1-(2-methyl-benzyl)-piperidine-4-carboxylic acid (4-tert-butyl-phenyl)-amide 381.2 | 4-Hydroxy-piperidine-4-carboxylic acid (4-tert-butyl-phenyl)-amide (intermediate 3) and 1-Bromomethyl-2-methyl-benzene (commercially available) |

TABLE 1-continued

| Ex | Structure | Chemical name<br>MS (m/e)<br>[(M + H)+] | Starting material |
|---|---|---|---|
| 47 | 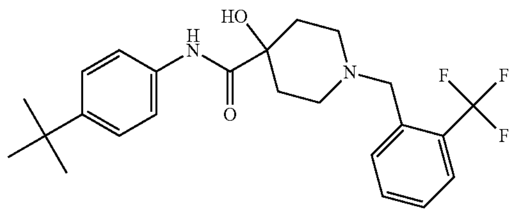 [SMILES: CC(C)(C)c1ccc(NC(=O)C2(O)CCN(Cc3ccccc3C(F)(F)F)CC2)cc1] | 4-Hydroxy-1-(2-trifluoromethyl-benzyl)-piperidine-4-carboxylic acid (4-tert-butyl-phenyl)-amide<br>435.2 | 4-Hydroxy-piperidine-4-carboxylic acid (4-tert-butyl-phenyl)-amide (intermediate 3) and 1-Bromomethyl-2-trifluoromethyl-benzene (commercially available) |
| 48 | 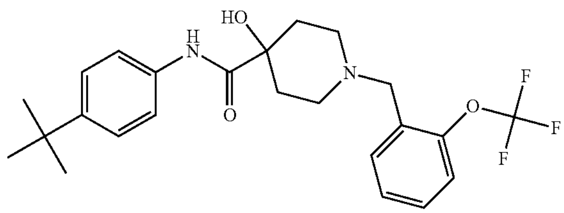 [SMILES: CC(C)(C)c1ccc(NC(=O)C2(O)CCN(Cc3ccccc3OC(F)(F)F)CC2)cc1] | 4-Hydroxy-1-(2-trifluoromethoxy-benzyl)-piperidine-4-carboxylic acid (4-tert-butyl-phenyl)-amide<br>451.2 | 4-Hydroxy-piperidine-4-carboxylic acid (4-tert-butyl-phenyl)-amide (intermediate 3) and 1-Bromomethyl-2-trifluoromethoxy-benzene (commercially available) |
| 49 | 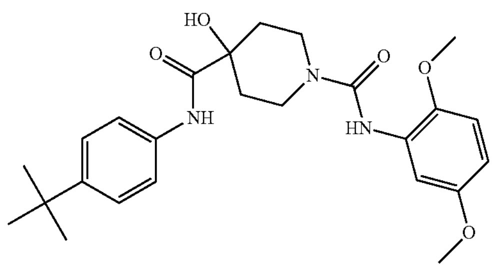 [SMILES: COc1ccc(OC)c(NC(=O)N2CCC(O)(C(=O)Nc3ccc(C(C)(C)C)cc3)CC2)c1] | 4-Hydroxy-piperidine-1,4-dicarboxylic acid 4-[(4-tert-butyl-phenyl)-amide] 1-[(2,5-dimethoxy-phenyl)-amide]<br>456.3 | 4-Hydroxy-piperidine-4-carboxylic acid (4-tert-butyl-phenyl)-amide (intermediate 3) and 2-Isocyanato-1,4-dimethoxy-benzene (commercially available) |
| 50 | 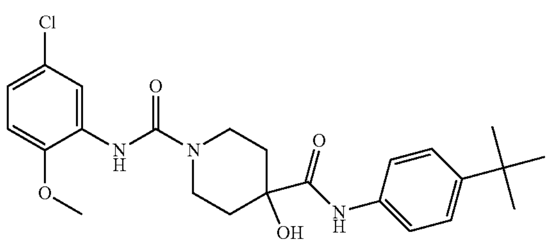 [SMILES: COc1ccc(Cl)cc1NC(=O)N1CCC(O)(C(=O)Nc2ccc(C(C)(C)C)cc2)CC1] | 4-Hydroxy-piperidine-1,4-dicarboxylic acid 4-[(4-tert-butyl-phenyl)-amide] 1-[(5-chloro-2-methoxy-phenyl)-amide]<br>460.2 | 4-Hydroxy-piperidine-4-carboxylic acid (4-tert-butyl-phenyl)-amide (intermediate 3) and 4-Chloro-2-isocyanato-1-methoxy-benzene (commercially available) |
| 51 | 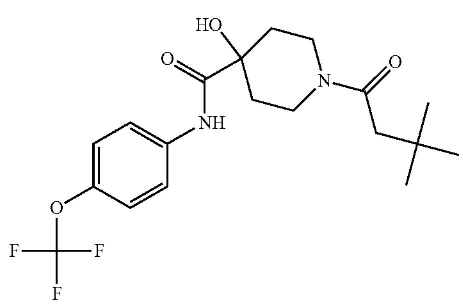 [SMILES: CC(C)(C)CC(=O)N1CCC(O)(C(=O)Nc2ccc(OC(F)(F)F)cc2)CC1] | 1-(3,3-Dimethyl-butyryl)-4-hydroxy-piperidine-4-carboxylic acid (4-trifluoromethoxy-phenyl)-amide<br>403.2 | 4-Hydroxy-piperidine-4-carboxylic acid (4-trifluoromethoxy-phenyl)-amide (intermediate 1) and 3,3-Dimethyl-butyryl chloride (commercially available) |

TABLE 1-continued

| Ex | Structure | Chemical name MS (m/e) [(M + H)+] | Starting material |
|---|---|---|---|
| 52 | 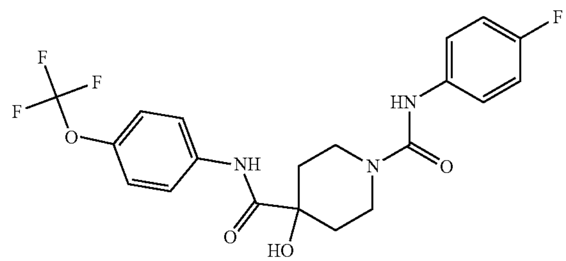 [SMILES: O=C(Nc1ccc(F)cc1)N1CCC(O)(C(=O)Nc2ccc(OC(F)(F)F)cc2)CC1] | 4-Hydroxy-piperidine-1,4-dicarboxylic acid 1-[(4-fluoro-phenyl)-amide] 4-[(4-trifluoromethoxy-phenyl)-amide] 442.2 | 4-Hydroxy-piperidine-4-carboxylic acid (4-trifluoromethoxy-phenyl)-amide (intermediate 1) and 1-Fluoro-4-isocyanato-benzene (commercially available) |
| 53 | 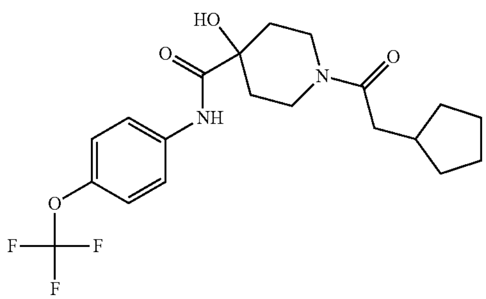 [SMILES: O=C(CC1CCCC1)N1CCC(O)(C(=O)Nc2ccc(OC(F)(F)F)cc2)CC1] | 1-(2-Cyclopentyl-acetyl)-4-hydroxy-piperidine-4-carboxylic acid (4-trifluoromethoxy-phenyl)-amide 415.2 | 4-Hydroxy-piperidine-4-carboxylic acid (4-trifluoromethoxy-phenyl)-amide (intermediate 1) and Cyclopentyl-acetyl chloride (commercially available) |
| 54 | 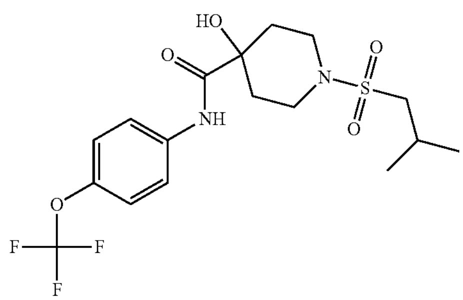 [SMILES: CC(C)CS(=O)(=O)N1CCC(O)(C(=O)Nc2ccc(OC(F)(F)F)cc2)CC1] | 4-Hydroxy-1-(2-methyl-propane-1-sulfonyl)-piperidine-4-carboxylic acid (4-trifluoromethoxy-phenyl)-amide 425.2 | 4-Hydroxy-piperidine-4-carboxylic acid (4-trifluoromethoxy-phenyl)-amide (intermediate 1) and 2-Methyl-propane-1-sulfonyl chloride (commercially available) |
| 55 | 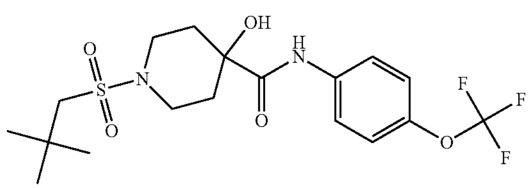 [SMILES: CC(C)(C)CS(=O)(=O)N1CCC(O)(C(=O)Nc2ccc(OC(F)(F)F)cc2)CC1] | 1-(2,2-Dimethyl-propane-1-sulfonyl)-4-hydroxy-piperidine-4-carboxylic acid (4-trifluoromethoxy-phenyl)-amide 439.1 | 4-Hydroxy-piperidine-4-carboxylic acid (4-trifluoromethoxy-phenyl)-amide (intermediate 1) and 2,2-Dimethyl-propane-1-sulfonyl chloride (commercially available) |
| 56 | 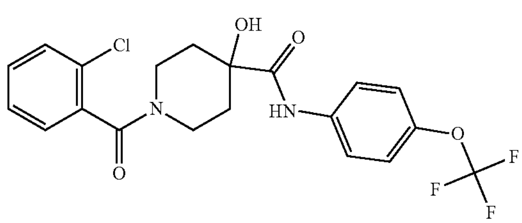 [SMILES: O=C(c1ccccc1Cl)N1CCC(O)(C(=O)Nc2ccc(OC(F)(F)F)cc2)CC1] | 1-(2-Chloro-benzoyl)-4-hydroxy-piperidine-4-carboxylic acid (4-trifluoromethoxy-phenyl)-amide 443.1 | 4-Hydroxy-piperidine-4-carboxylic acid (4-trifluoromethoxy-phenyl)-amide (intermediate 1) and 2-Chloro-benzoyl chloride (commercially available) |

TABLE 1-continued

| Ex | Structure | Chemical name<br>MS (m/e)<br>[(M + H)+] | Starting material |
|---|---|---|---|
| 57 | 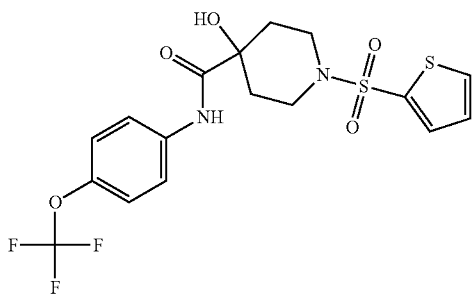 [SMILES: O=C(Nc1ccc(OC(F)(F)F)cc1)C1(O)CCN(S(=O)(=O)c2cccs2)CC1] | 4-Hydroxy-1-(thiophene-2-sulfonyl)-piperidine-4-carboxylic acid (4-trifluoromethoxy-phenyl)-amide<br>451 | 4-Hydroxy-piperidine-4-carboxylic acid (4-trifluoromethoxy-phenyl)-amide (intermediate 1) and Thiophene-2-sulfonyl chloride (commercially available) |
| 58 | 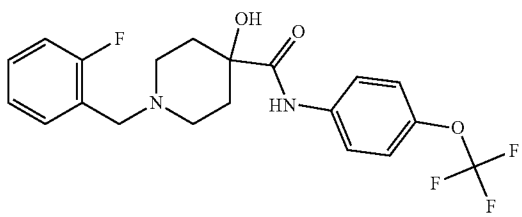 [SMILES: O=C(Nc1ccc(OC(F)(F)F)cc1)C1(O)CCN(Cc2ccccc2F)CC1] | 1-(2-Fluoro-benzyl)-4-hydroxy-piperidine-4-carboxylic acid (4-trifluoromethoxy-phenyl)-amide<br>413.2 | 4-Hydroxy-piperidine-4-carboxylic acid (4-trifluoromethoxy-phenyl)-amide (intermediate 1) and 1-Bromomethyl-2-fluoro-benzene (commercially available) |
| 59 | 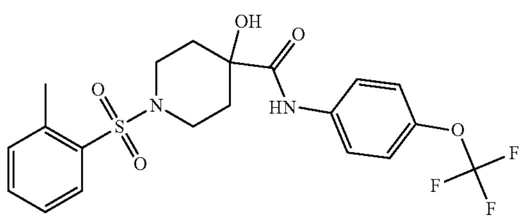 [SMILES: Cc1ccccc1S(=O)(=O)N1CCC(O)(C(=O)Nc2ccc(OC(F)(F)F)cc2)CC1] | 4-Hydroxy-1-(toluene-2-sulfonyl)-piperidine-4-carboxylic acid (4-trifluoromethoxy-phenyl)-amide<br>459.1 | 4-Hydroxy-piperidine-4-carboxylic acid (4-trifluoromethoxy-phenyl)-amide (intermediate 1) and 2-Methyl-benzenesulfonyl chloride (commercially available) |
| 60 | 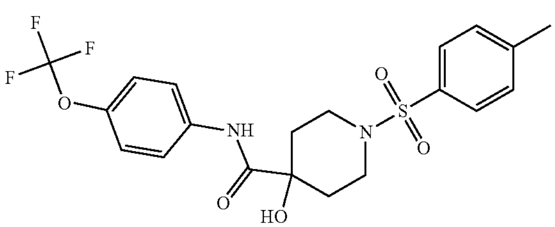 [SMILES: Cc1ccc(S(=O)(=O)N2CCC(O)(C(=O)Nc3ccc(OC(F)(F)F)cc3)CC2)cc1] | 4-Hydroxy-1-(toluene-4-sulfonyl)-piperidine-4-carboxylic acid (4-trifluoromethoxy-phenyl)-amide<br>459.1 | 4-Hydroxy-piperidine-4-carboxylic acid (4-trifluoromethoxy-phenyl)-amide (intermediate 1) and 4-Methyl-benzenesulfonyl chloride (commercially available) |
| 61 | 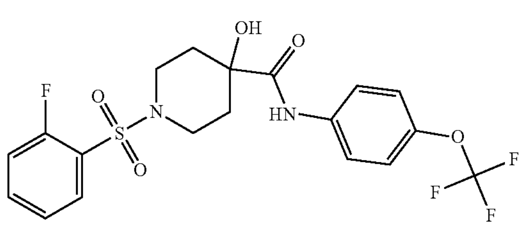 [SMILES: O=C(Nc1ccc(OC(F)(F)F)cc1)C1(O)CCN(S(=O)(=O)c2ccccc2F)CC1] | 1-(2-Fluoro-benzenesulfonyl)-4-hydroxy-piperidine-4-carboxylic acid (4-trifluoromethoxy-phenyl)-amide<br>463.1 | 4-Hydroxy-piperidine-4-carboxylic acid (4-trifluoromethoxy-phenyl)-amide (intermediate 1) and 2-Fluoro-benzenesulfonyl chloride (commercially available) |

TABLE 1-continued

| Ex | Structure | Chemical name MS (m/e) [(M + H)+] | Starting material |
|---|---|---|---|
| 62 | 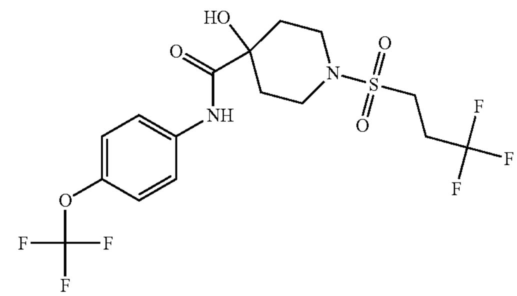 [SMILES: O=C(Nc1ccc(OC(F)(F)F)cc1)C1(O)CCN(S(=O)(=O)CCC(F)(F)F)CC1] | 4-Hydroxy-1-(3,3,3-trifluoro-propane-1-sulfonyl)-piperidine-4-carboxylic acid (4-trifluoromethoxy-phenyl)-amide 465.1 | 4-Hydroxy-piperidine-4-carboxylic acid (4-trifluoromethoxy-phenyl)-amide (intermediate 1) and 3,3,3-Trifluoro-propane-1-sulfonyl chloride (commercially available) |
| 63 | 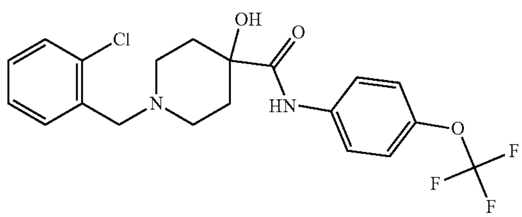 [SMILES: O=C(Nc1ccc(OC(F)(F)F)cc1)C1(O)CCN(Cc2ccccc2Cl)CC1] | 1-(2-Chloro-benzyl)-4-hydroxy-piperidine-4-carboxylic acid (4-trifluoromethoxy-phenyl)-amide 429.1 | 4-Hydroxy-piperidine-4-carboxylic acid (4-trifluoromethoxy-phenyl)-amide (intermediate 1) and 1-Bromomethyl-2-chloro-benzene (commercially available) |
| 64 | 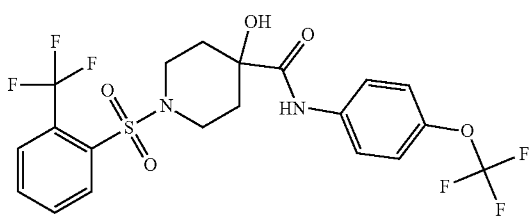 [SMILES: O=C(Nc1ccc(OC(F)(F)F)cc1)C1(O)CCN(S(=O)(=O)c2ccccc2C(F)(F)F)CC1] | 4-Hydroxy-1-(2-trifluoromethyl-benzenesulfonyl)-piperidine-4-carboxylic acid (4-trifluoromethoxy-phenyl)-amide 513.2 | 4-Hydroxy-piperidine-4-carboxylic acid (4-trifluoromethoxy-phenyl)-amide (intermediate 1) and 2-Trifluoromethyl-benzenesulfonyl chloride (commercially available) |
| 65 | 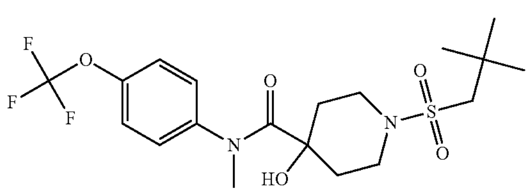 [SMILES: CN(C(=O)C1(O)CCN(S(=O)(=O)CC(C)(C)C)CC1)c1ccc(OC(F)(F)F)cc1] | 1-(2,2-Dimethyl-propane-1-sulfonyl)-4-hydroxy-piperidine-4-carboxylic acid methyl-(4-trifluoromethoxy-phenyl)-amide 453.3 | 4-Hydroxy-piperidine-4-carboxylic acid methyl-(4-trifluoromethoxy-phenyl)-amide (intermediate 4) and 2,2-Dimethyl-propane-1-sulfonyl chloride (commercially available) |
| 66 | 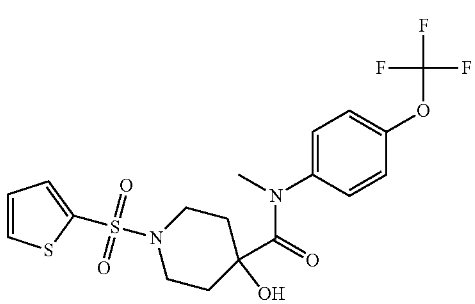 [SMILES: CN(C(=O)C1(O)CCN(S(=O)(=O)c2cccs2)CC1)c1ccc(OC(F)(F)F)cc1] | 4-Hydroxy-1-(thiophene-2-sulfonyl)-piperidine-4-carboxylic acid methyl-(4-trifluoromethoxy-phenyl)-amide 465.1 | 4-Hydroxy-piperidine-4-carboxylic acid methyl-(4-trifluoromethoxy-phenyl)-amide (intermediate 4) and Thiophene-2-sulfonyl chloride (commercially available) |

TABLE 1-continued

| Ex | Structure | Chemical name MS (m/e) [(M + H)+] | Starting material |
|---|---|---|---|
| 67 | 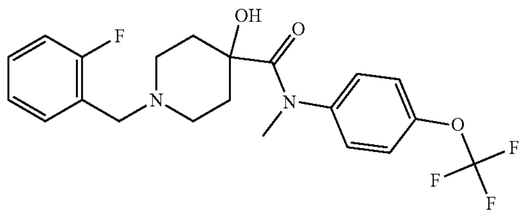 [SMILES: CN(C(=O)C1(O)CCN(Cc2ccccc2F)CC1)c1ccc(OC(F)(F)F)cc1] | 1-(2-Fluoro-benzyl)-4-hydroxy-piperidine-4-carboxylic acid methyl-(4-trifluoromethoxy-phenyl)-amide 427.1 | 4-Hydroxy-piperidine-4-carbopxylic acid methyl-(4-trifluoromethoxy-phenyl)-amide (intermediate 4) and 1-Bromomethyl-2-fluoro-benzene (commercially available) |
| 68 | 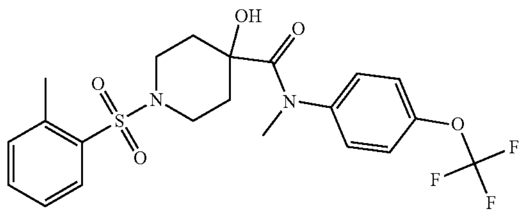 [SMILES: Cc1ccccc1S(=O)(=O)N1CCC(O)(C(=O)N(C)c2ccc(OC(F)(F)F)cc2)CC1] | 4-Hydroxy-1-(toluene-2-sulfonyl)-piperidine-4-carboxylic acid methyl-(4-trifluoromethoxy-phenyl)-amide 473.2 | 4-Hydroxy-piperidine-4-carboxylic acid methyl-(4-trifluoromethoxy-phenyl)-amide (intermediate 4) and 2-Methyl-benzenesulfonyl chloride (commercially available) |
| 69 | 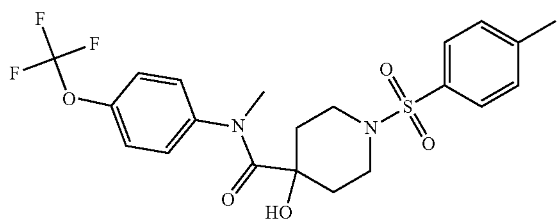 [SMILES: Cc1ccc(S(=O)(=O)N2CCC(O)(C(=O)N(C)c3ccc(OC(F)(F)F)cc3)CC2)cc1] | 4-Hydroxy-1-(toluene-4-sulfonyl)-piperidine-4-carboxylic acid methyl-(4-trifluoromethoxy-phenyl)-amide 473.2 | 4-Hydroxy-piperidine-4-carboxylic acid methyl-(4-trifluoromethoxy-phenyl)-amide (intermediate 4) and 4-Methyl-benzenesulfonyl chloride (commercially available) |
| 70 | 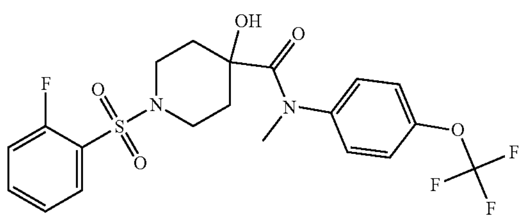 [SMILES: CN(C(=O)C1(O)CCN(S(=O)(=O)c2ccccc2F)CC1)c1ccc(OC(F)(F)F)cc1] | 1-(2-Fluoro-benzenesulfonyl)-4-hydroxy-piperidine-4-carboxylic acid methyl-(4-trifluoromethoxy-phenyl)-amide 477.2 | 4-Hydroxy-piperidine-4-carboxylic acid methyl-(4-trifluoromethoxy-phenyl)-amide (intermediate 4) and 2-Fluoro-benzenesulfonyl chloride (commercially available) |
| 71 | 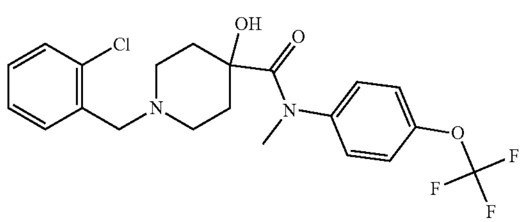 [SMILES: CN(C(=O)C1(O)CCN(Cc2ccccc2Cl)CC1)c1ccc(OC(F)(F)F)cc1] | 1-(2-Chloro-benzyl)-4-hydroxy-piperidine-4-carboxylic acid methyl-(4-trifluoromethoxy-phenyl)-amide 443.2 | 4-Hydroxy-piperidine-4-carboxylic acid methyl-(4-trifluoromethoxy-phenyl)-amide (intermediate 4) and 1-Bromomethyl-2-chloro-benzene (commercially available) |
| 72 | 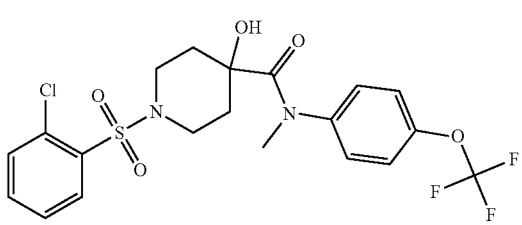 [SMILES: CN(C(=O)C1(O)CCN(S(=O)(=O)c2ccccc2Cl)CC1)c1ccc(OC(F)(F)F)cc1] | 1-(2-Chloro-benzenesulfonyl)-4-hydroxy-piperidine-4-carboxylic acid methyl-(4-trifluoromethoxy-phenyl)-amide 493.1 | 4-Hydroxy-piperidine-4-carboxylic acid methyl-(4-trifluoromethoxy-phenyl)-amide (intermediate 4) and 2-Chloro-benzenesulfonyl chloride (commercially available) |

TABLE 1-continued

| Ex | Structure | Chemical name MS (m/e) [(M + H)+] | Starting material |
|---|---|---|---|
| 73 | 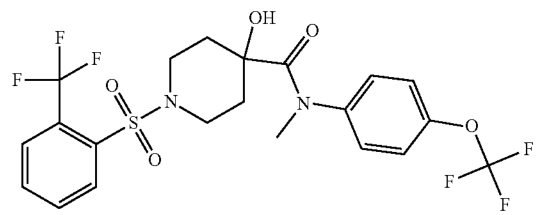 [SMILES: CN(C(=O)C1(O)CCN(S(=O)(=O)c2ccccc2C(F)(F)F)CC1)c1ccc(OC(F)(F)F)cc1] | 4-Hydroxy-1-(2-trifluoromethyl-benzenesulfonyl)-piperidine-4-carboxylic acid methyl-(4-trifluoromethoxy-phenyl)-amide 527.2 | 4-Hydroxy-piperidine-4-carboxylic acid methyl-(4-trifluoromethoxy-phenyl)-amide (intermediate 4) and 2-Trifluoromethyl-benzenesulfonyl chloride (commercially available) |
| 74 | 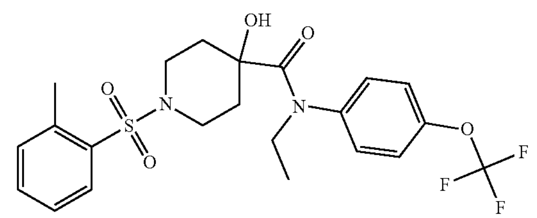 [SMILES: CCN(C(=O)C1(O)CCN(S(=O)(=O)c2ccccc2C)CC1)c1ccc(OC(F)(F)F)cc1] | 4-Hydroxy-1-(toluene-2-sulfonyl)-piperidine-4-carboxylic acid ethyl-(4-trifluoromethoxy-phenyl)-amide 487.2 | 4-Hydroxy-piperidine-4-carboxylic acid ethyl-(4-trifluoromethoxy-phenyl)-amide (intermediate 5) and 2-Methyl-benzenesulfonyl chloride (commercially available) |
| 75 | 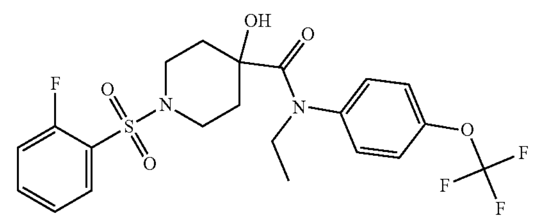 [SMILES: CCN(C(=O)C1(O)CCN(S(=O)(=O)c2ccccc2F)CC1)c1ccc(OC(F)(F)F)cc1] | 1-(2-Fluoro-benzenesulfonyl)-4-hydroxy-piperidine-4-carboxylic acid ethyl-(4-tri-fluoromethoxy-phenyl)-amide 491.2 | 4-Hydroxy-piperidine-4-carboxylic acid ethyl-(4-trifluoromethoxy-phenyl)-amide (intermediate 5) and 2-Fluoro-benzenesulfonyl chloride (commercially available) |

Example 76

1-(2-Chloro-benzenesulfonyl)-4-methoxy-piperidine-4-carboxylic acid (4-tert-butyl-phenyl)-amide

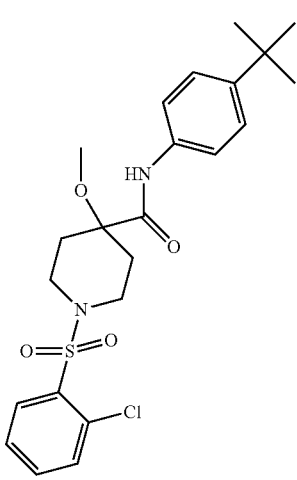 [SMILES: COC1(C(=O)Nc2ccc(C(C)(C)C)cc2)CCN(S(=O)(=O)c2ccccc2Cl)CC1]

Step 1

4-Hydroxy-piperidine-1,4-dicarboxylic acid 1-tert-butyl ester 4-ethyl ester

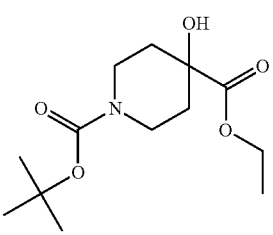 [SMILES: CCOC(=O)C1(O)CCN(C(=O)OC(C)(C)C)CC1]

Under an inert atmosphere a 500 mL four necked round bottom flask (flame dried) with a mechanic stirrer was charged with 3.56 ml diisopropyl amine in 75 mL THF. At −10° C. 15.8 mL 1.6 N BuLi/hexane solution was added drop wise. The light yellow solution was stirred for 40 minutes at −10° C. and cooled then down to −75° C. 5.4 g ethyl 1-tert-butoxycarbonylpiperidine-4-carboxylate in 25 ml THF were added over 50 minutes and stirred for 3 h at −75° C. 5.5 g (2R,8S)-(+)-(camphorsulfonyl)oxaziridine in 80 mL THF were added drop wise over 1 h. The reaction was stirred for 2 h at −75° C. and then slowly warmed up over night to ambient temperature. The amber reaction solution was cooled to 5° C. and 150 mL saturated NH₄Cl-solution, 50 mL water and 50 mL ethyl acetate was added and stirred for 10 minutes. The aqueous layer was separated and extracted once with 100 mL ethyl acetate. The organic layers were washed once with 200 mL brine, dried over Na₂SO₄, filtered off and concentrated under vacuum. The residue was purified over a silica cartridge eluting with a gradient formed from heptane and ethyl acetate to yield after evaporation of the product containing fractions 4.24 g (74%) of the title compound as light yellow viscous oil. MS (m/e): 174.2 [(M-Boc)⁺].

Step 2

4-Methoxy-piperidine-1,4-dicarboxylic acid mono-tert-butyl ester

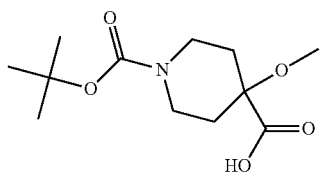 [SMILES: COC1(C(=O)O)CCN(C(=O)OC(C)(C)C)CC1]

A mixture of 0.415 g (1.52 mmol) 4-Hydroxy-piperidine-1,4-dicarboxylic acid 1-tert-butyl ester 4-ethyl ester, 68 mg (1.97 mmol) NaH (55% in oil) and 0.3 g (2.12 mmol) iodomethane in 10 mL DMF was stirred for 2 h at room temperature. Water was added and the mixture was concentrated to dryness. The residue was dissolved in THF and water and 0.254 g (6 mmol) LiOH.H₂O wad added and the mixture was stirred for 16 h at room temperature. After evaporation the residue was subjected to purification by preparative HPLC on reversed phase eluting with a gradient formed from acetonitrile, water and formic acid to yield after evaporation of the product containing fractions 49.7 mg (13%) of the title compound as white solid. MS (m/e): 258.1 [(M−H)].

Step 3

4-Methoxy-piperidine-4-carboxylic acid (4-tert-butyl-phenyl)-amide, hydrochloride

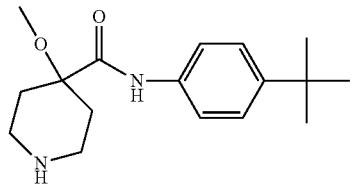 [SMILES: COC1(C(=O)Nc2ccc(C(C)(C)C)cc2)CCNCC1]

A mixture of 49.7 mg (0.192 mmol) 4-Methoxy-piperidine-1,4-dicarboxylic acid mono-tert-butyl ester, 87 mg (0.23 mmol) HATU, 74 mg (0.575 mmol) DIPEA and 32.8 mg (0.22 mmol) 4-tert.-butylaniline in 3 mL DMF was stirred for 3 h at room temperature and concentrated to dryness. The crude product (62 mg) was used without further purification in the subsequent step. MS (m/e): 391.3 [(M+H)⁺]. 1 mL DCM and 1.19 mL 4N HCl in dioxane was added and stirred for 2 h at room temperature. The precipitate was filtered off and the filtrate concentrated to dryness and used without further purification in the subsequent step. MS (m/e): 291.1 [(M+H)⁺].

Step 4

A mixture of 25.5 mg (0.078 mmol) 4-Methoxy-piperidine-4-carboxylic acid (4-tert-butyl-phenyl)-amide, hydrochloride, 21.4 mg (0.1 mmol) 2-chlorobenzenesulfonyl chloride and 39.4 mg (0.39 mmol) NEt₃ in 1.5 mL DCM was stirred for 16 h at room temperature. The mixture was concentrated and subjected to purification by preparative HPLC on reversed phase eluting with a gradient formed from acetonitrile, water and formic acid to yield after evaporation of the product containing fractions 20.2 mg (56%) of the title compound as light yellow oil. MS (m/e): 465.2 [(M+H)⁺].

Example 77

4-Amino-1-(toluene-4-sulfonyl)-piperidine-4-carboxylic acid (4-tert-butyl-phenyl)-amide; hydrochloride

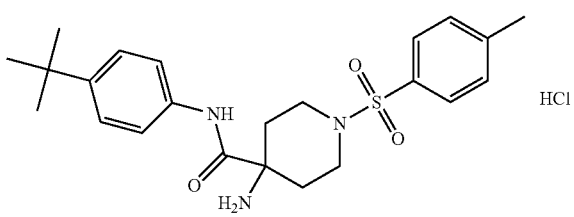 [SMILES: Cc1ccc(S(=O)(=O)N2CCC(N)(C(=O)Nc3ccc(C(C)(C)C)cc3)CC2)cc1 ; Cl]

Step 1

4-tert-Butoxycarbonylamino-1-(toluene-4-sulfonyl)-piperidine-4-carboxylic acid methyl ester

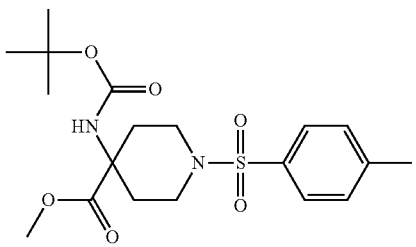 [SMILES: COC(=O)C1(NC(=O)OC(C)(C)C)CCN(S(=O)(=O)c2ccc(C)cc2)CC1]

A mixture of 0.5 g (1.936 mmol) 4-tert-Butoxycarbonylamino-piperidine-4-carboxylic acid methyl ester, 0.387 g (2.03 mmol) p-toluenesulfonyl chloride and 0.587 g (5.8 mmol) NEt₃ in 6 mL DCM was stirred at room temperature over night. DCM and NaHCO₃ aq. was added and the organic layer was separated and dried with MgSO₄. After evaporation the residue was dried under high vacuum and used without further purification. 0.796 g (95%) of the title compound was obtained as white foam. MS (m/e): 413.2 [(M+H)⁺].

Step 2

[4-(4-tert-Butyl-phenylcarbamoyl)-1-(toluene-4-sulfonyl)-piperidin-4-yl]-carbamic acid tert-butyl ester

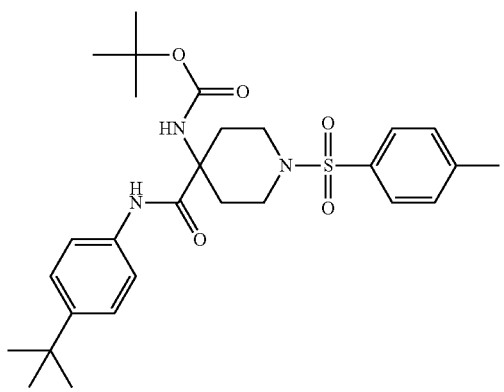 [SMILES: Cc1ccc(S(=O)(=O)N2CCC(NC(=O)OC(C)(C)C)(C(=O)Nc3ccc(C(C)(C)C)cc3)CC2)cc1]

A mixture of 0.493 g (1.195 mmol) 4-tert-Butoxycarbonylamino-1-(toluene-4-sulfonyl)-piperidine-4-carboxylic acid methyl ester and 0.478 mL KOH 5N aq. in a mixture of methanol, THF and water was stirred for 1.5 h at 45° C. The mixture was acidified with acetic acid and evaporated to dryness. The residue was taken up in 2 mL DMF, 28.7 mg (0.154 mmol) EDCI, 18.8 mg (0.309 mmol) DMAP and 23 mg (0.154 mmol) 4-tert.-butyl aniline was added and the mixture was shaken for 24 h at room temperature. The mixture was evaporated to dryness and subjected to purification by preparative HPLC on reversed phase eluting with a gradient formed from acetonitrile, water and formic acid to yield after evaporation of the product containing fractions 7.9 mg (10%) of the title compound. MS (m/e): 530.2 [(M+H)$^+$].

Step 3

A mixture of 7.9 mg (0.015 mmol) [4-(4-tert-Butyl-phenylcarbamoyl)-1-(toluene-4-sulfonyl)-piperidin-4-yl]-carbamic acid tert-butyl ester and 0.15 mL HCl in dioxane (4N) was stirred at 60° C. over night. Diethyl ether was added and the precipitate was filtered, washed with diethyl ether and dried to afford 4.5 mg (65%) of the title compound. MS (m/e): 430.3 [(M+H)$^+$].

Example 78

4-Amino-1-(toluene-4-sulfonyl)-piperidine-4-carboxylic acid (4-isopropyl-phenyl)-amide; hydrochloride

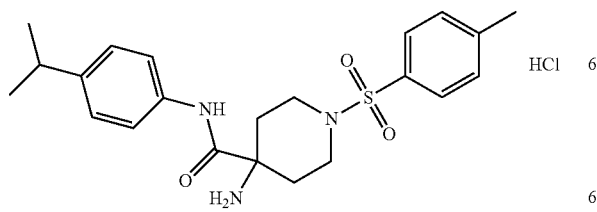

In analogy to the procedure described for the synthesis of 4-Amino-1-(toluene-4-sulfonyl)-piperidine-4-carboxylic acid (4-tert-butyl-phenyl)-amide; hydrochloride (example 77) the title compound was prepared from 4-tert-Butoxycarbonylamino-1-(toluene-4-sulfonyl)-piperidine-4-carboxylic acid (example 77, step 2) and 4-isopropyl-aniline with subsequent cleavage of the Boc group with HCl. MS (m/e): 416.3 [(M+H)$^+$].

Example 79

4-Amino-1-(toluene-4-sulfonyl)-piperidine-4-carboxylic acid (4-isopropoxy-phenyl)-amide; hydrochloride

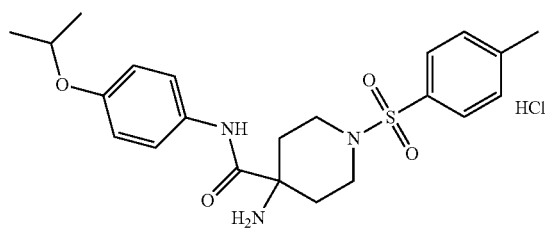 [SMILES: Cc1ccc(S(=O)(=O)N2CCC(N)(C(=O)Nc3ccc(OC(C)C)cc3)CC2)cc1 ; Cl]

In analogy to the procedure described for the synthesis of 4-Amino-1-(toluene-4-sulfonyl)-piperidine-4-carboxylic acid (4-tert-butyl-phenyl)-amide; hydrochloride (example 77) the title compound was prepared from 4-tert-Butoxycarbonylamino-1-(toluene-4-sulfonyl)-piperidine-4-carboxylic acid (example 77, step 2) and 4-isopropoxy-aniline with subsequent cleavage of the Boc group with HCl. MS (m/e): 432.3 [(M+H)$^+$].

Example 80

4-Amino-1-(toluene-4-sulfonyl)-piperidine-4-carboxylic acid (4-trifluoromethoxy-phenyl)-amide; hydrochloride

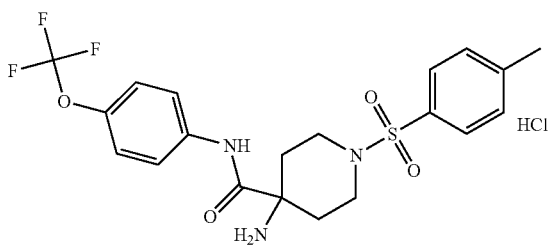 [SMILES: Cc1ccc(S(=O)(=O)N2CCC(N)(C(=O)Nc3ccc(OC(F)(F)F)cc3)CC2)cc1 ; Cl]

In analogy to the procedure described for the synthesis of 4-Amino-1-(toluene-4-sulfonyl)-piperidine-4-carboxylic acid (4-tert-butyl-phenyl)-amide; hydrochloride (example 77) the title compound was prepared from 4-tert-Butoxycarbonylamino-1-(toluene-4-sulfonyl)-piperidine-4-carboxylic acid (example 77, step 2) and 4-trifluoromethoxy-aniline with subsequent cleavage of the Boc group with HCl. MS (m/e): 458.3 [(M+H)$^+$].

Example 81

4-Amino-1-(toluene-4-sulfonyl)-piperidine-4-carboxylic acid (4-ethyl-phenyl)-amide

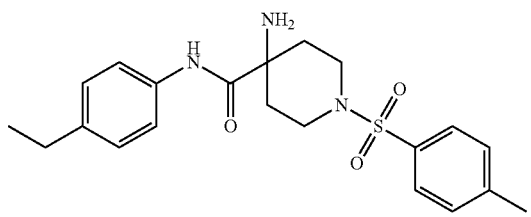 [SMILES: CCc1ccc(NC(=O)C2(N)CCN(S(=O)(=O)c3ccc(C)cc3)CC2)cc1]

In analogy to the procedure described for the synthesis of 4-Amino-1-(toluene-4-sulfonyl)-piperidine-4-carboxylic acid (4-tert-butyl-phenyl)-amide; hydrochloride (example 77) the title compound was prepared from 4-tert-Butoxycarbonylamino-1-(toluene-4-sulfonyl)-piperidine-4-carboxylic acid (example 77, step 2) and 4-ethyl-aniline with subsequent cleavage of the Boc group with HCl. The compound was purified with preparative HPLC on reversed phase. MS (m/e): 402.4 [(M+H)$^+$].

Example 82

4-Amino-4-(4-isopropyl-phenylcarbamoyl)-piperidine-1-carboxylic acid benzyl ester; hydrochloride

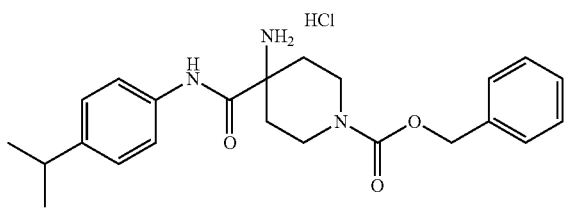 [SMILES: Cl ; CC(C)c1ccc(NC(=O)C2(N)CCN(C(=O)OCc3ccccc3)CC2)cc1]

Step 1

4-tert-Butoxycarbonylamino-4-(4-isopropyl-phenylcarbamoyl)-piperidine-1-carboxylic acid benzyl ester

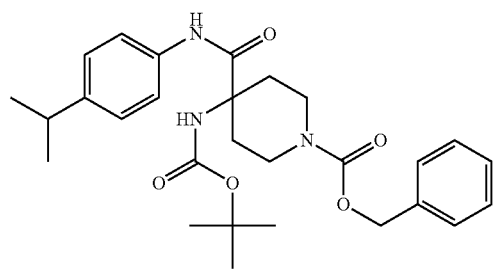 [SMILES: CC(C)c1ccc(NC(=O)C2(NC(=O)OC(C)(C)C)CCN(C(=O)OCc3ccccc3)CC2)cc1]

A mixture of 3.78 g (10 mmol) 4-tert-Butoxycarbonylamino-piperidine-1,4-dicarboxylic acid monobenzyl ester (commercially available), 1.76 g (13 mmol) 4-isopropyl-aniline (commercially available), 2.1 g (11 mmol) EDCI and 1.36 g (11 mmol) DMAP in 50 mL THF was stirred at room temperature over night. After concentration of the mixture ethyl acetate and water was added. The mixture was extracted with ethyl acetate and the combined organic fractions were dried with MgSO$_4$ and evaporated. The residue was purified over silica eluting with a gradient formed from ethyl acetate and hexane to afford after evaporation of the product containing fractions 2.85 g (57%) of the title compound as white solid. MS (m/e): 496.3 [(M+H)$^+$].

Step 2

In analogy to the procedure described for the removal of the Boc-group (example 77, step 3) the protecting group was removed with HCl in dioxane to afford the title compound as white crystals. MS (m/e): 396.2 [(M+H)$^+$].

Example 83

4-Amino-1-(4-isopropyl-benzenesulfonyl)-piperidine-4-carboxylic acid (4-isopropyl-phenyl)-amide; hydrochloride

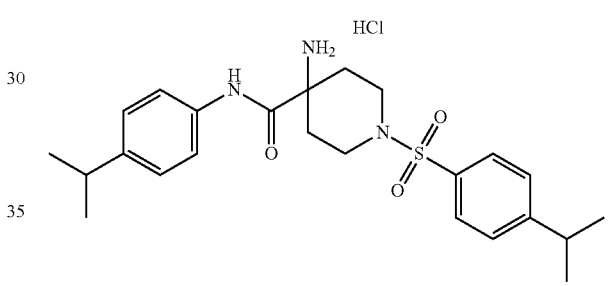

Step 1

4-tert-Butoxycarbonylamino-1-(4-isopropyl-benzenesulfonyl)-piperidine-4-carboxylic acid methyl ester

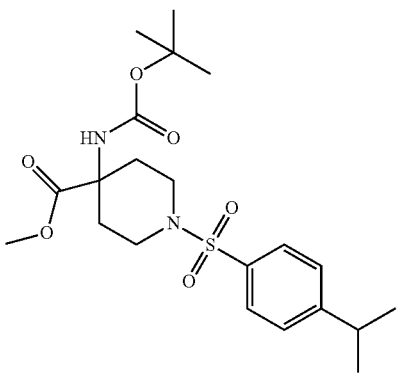 [SMILES: COC(=O)C1(NC(=O)OC(C)(C)C)CCN(S(=O)(=O)c2ccc(C(C)C)cc2)CC1]

In analogy to the procedure described for the synthesis of 4-tert-Butoxycarbonylamino-1-(toluene-4-sulfonyl)-piperidine-4-carboxylic acid methyl ester (example 77, step 1) the title compound was prepared from 4-tert-Butoxycarbonylamino-piperidine-4-carboxylic acid methyl ester (commercially available) and 4-Isopropyl-benzenesulfonyl chloride (commercially available). MS (m/e): 441.2 [(M+H)⁺].

Step 2

[1-(4-Isopropyl-benzenesulfonyl)-4-(4-isopropyl-phenylcarbamoyl)-piperidin-4-yl]-carbamic acid tert-butyl ester

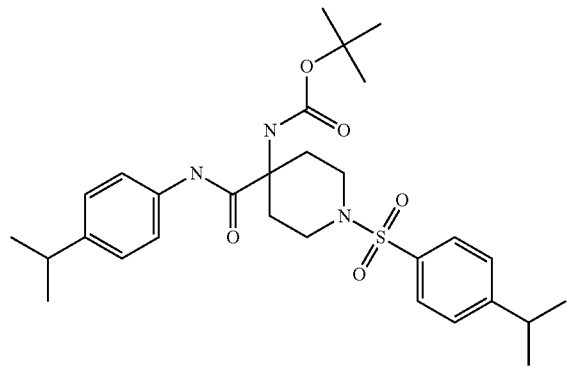 [SMILES: CC(C)c1ccc(NC(=O)C2(NC(=O)OC(C)(C)C)CCN(S(=O)(=O)c3ccc(C(C)C)cc3)CC2)cc1]

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-isopropyl-benzenesulfonyl)-piperidine-4-carboxylic acid methyl ester through cleavage of the ester functionality with KOH and subsequent amide coupling with 4-isopropyl-aniline (commercially available). MS (m/e): 544.3 [(M+H)⁺].

Step 3

In analogy to the procedure described for the removal of the Boc-group (example 77, step 3) the protecting group was removed with HCl in dioxane to afford the title compound as white solid. MS (m/e): 444.4 [(M+H)⁺].

Example 84

4-Amino-piperidine-1,4-dicarboxylic acid 4-p-tolylamide 1-[(4-trifluoromethoxy-phenyl)-amide]; hydrochloride

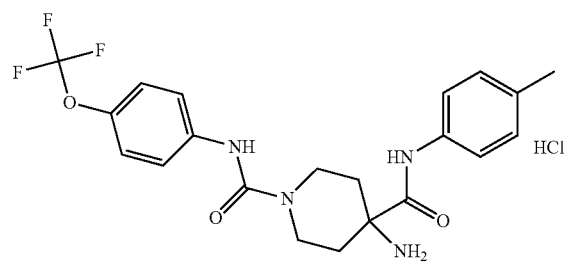 [SMILES: Cc1ccc(NC(=O)C2(N)CCN(C(=O)Nc3ccc(OC(F)(F)F)cc3)CC2)cc1 ; Cl]

Step 1

4-tert-Butoxycarbonylamino-1-(4-trifluoromethoxy-phenylcarbamoyl)-piperidine-4-carboxylic acid methyl ester

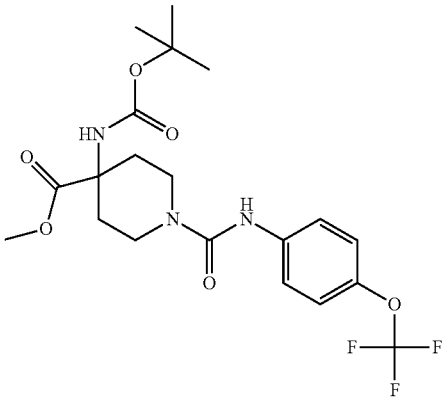 [SMILES: COC(=O)C1(NC(=O)OC(C)(C)C)CCN(C(=O)Nc2ccc(OC(F)(F)F)cc2)CC1]

In analogy to the procedure described for the synthesis of 4-tert-Butoxycarbonylamino-1-(toluene-4-sulfonyl)-piperidine-4-carboxylic acid methyl ester (example 77, step 1) the title compound was prepared from 4-tert-Butoxycarbonylamino-piperidine-4-carboxylic acid methyl ester (commercially available) and 4-(trifluoromethoxy)phenyl isocyanate (commercially available). MS (m/e): 462.2 [(M+H)⁺].

Step 2

[4-p-Tolylcarbamoyl-1-(4-trifluoromethoxy-phenylcarbamoyl)-piperidin-4-yl]-carbamic acid tert-butyl ester

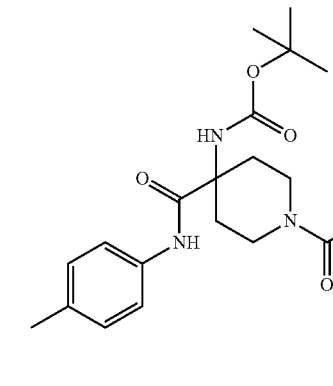

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-trifluoromethoxy-phenylcarbamoyl)-piperidine-4-carboxylic acid methyl ester through cleavage of the ester functionality with KOH and subsequent amide coupling with 4-methyl-aniline (commercially available). MS (m/e): 537.3 [(M+H)⁺].

Step 3

In analogy to the procedure described for the removal of the Boc-group (example 77, step 3) the protecting group was removed with HCl in dioxane to afford the title compound as white solid. MS (m/e): 437.2 [(M+H)+].

Example 85

4-Amino-piperidine-1,4-dicarboxylic acid 4-[(4-isopropyl-phenyl)-amide]1-[(4-trifluoromethoxy-phenyl)-amide]; hydrochloride

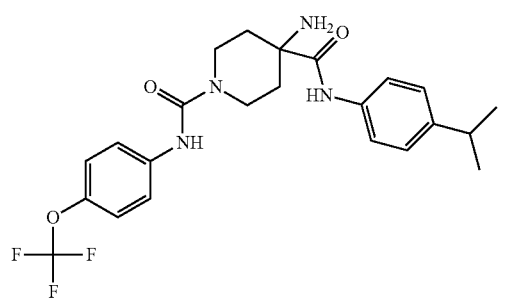

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-trifluoromethoxy-phenylcarbamoyl)-piperidine-4-carboxylic acid methyl ester through cleavage of the ester functionality with KOH and subsequent amide coupling with 4-isopropyl-aniline (commercially available) followed by the removal of the protecting group with HCl in dioxane to afford the title compound. MS (m/e): 465.2 [(M+H)+].

Example 86

4-Amino-piperidine-1,4-dicarboxylic acid 4-[(4-tert-butyl-phenyl)-amide]1-[(4-trifluoromethoxy-phenyl)-amide]; hydrochloride

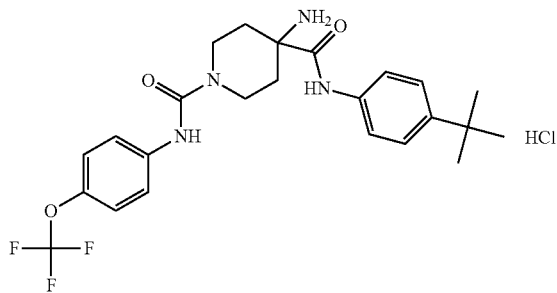 [SMILES: CC(C)(C)c1ccc(NC(=O)C2(N)CCN(C(=O)Nc3ccc(OC(F)(F)F)cc3)CC2)cc1 ; Cl]

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-trifluoromethoxy-phenylcarbamoyl)-piperidine-4-carboxylic acid methyl ester through cleavage of the ester functionality with KOH and subsequent amide coupling with 4-tert.-butyl-aniline (commercially available) followed by the removal of the protecting group with HCl in dioxane to afford the title compound. MS (m/e): 479.2 [(M+H)+].

Example 87

4-Amino-piperidine-1,4-dicarboxylic acid 1-[(4-tert-butyl-phenyl)-amide]-4-[(4-fluoro-phenyl)-amide]; hydrochloride

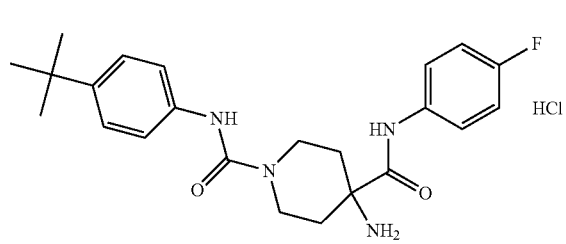 [SMILES: CC(C)(C)c1ccc(NC(=O)N2CCC(N)(C(=O)Nc3ccc(F)cc3)CC2)cc1 ; Cl]

Step 1

4-tert-Butoxycarbonylamino-1-(4-tert-butyl-phenyl-carbamoyl)-piperidine-4-carboxylic acid methyl ester

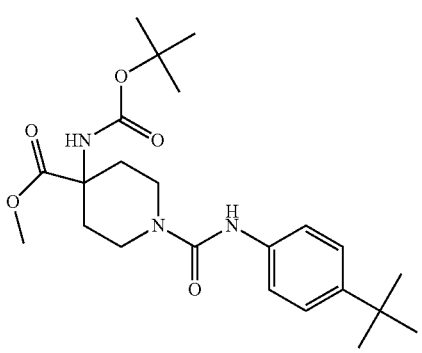 [SMILES: COC(=O)C1(NC(=O)OC(C)(C)C)CCN(C(=O)Nc2ccc(C(C)(C)C)cc2)CC1]

In analogy to the procedure described for the synthesis of 4-tert-Butoxycarbonylamino-1-(toluene-4-sulfonyl)-piperidine-4-carboxylic acid methyl ester (example 77, step 1) the title compound was prepared from 4-tert-Butoxycarbonylamino-piperidine-4-carboxylic acid methyl ester (commercially available) and 4-tert.-butyl phenyl isocyanate (commercially available). MS (m/e): 434.4 [(M+H)⁺].

Step 2

[1-(4-tert-Butyl-phenylcarbamoyl)-4-(4-fluoro-phenylcarbamoyl)-piperidin-4-yl]-carbamic acid tert-butyl ester

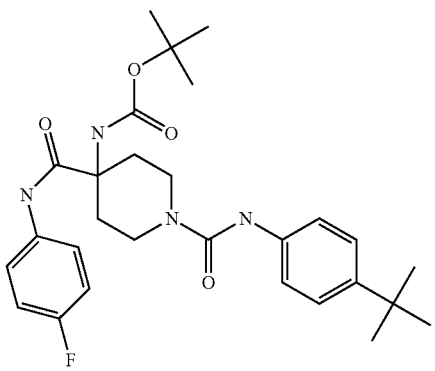 [SMILES: CC(C)(C)OC(=O)NC1(C(=O)Nc2ccc(F)cc2)CCN(C(=O)Nc2ccc(C(C)(C)C)cc2)CC1]

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-tert-butyl-phenylcarbamoyl)-piperidine-4-carboxylic acid methyl ester through cleavage of the ester functionality with KOH and subsequent amide coupling with 4-fluoro-aniline (commercially available). MS (m/e): 514.6 [(M+H)⁺].

Step 3

In analogy to the procedure described for the removal of the Boc-group (example 77, step 3) the protecting group was removed with HCl in dioxane to afford the title compound as white solid. MS (m/e): 413.3 [(M+H)⁺].

Example 88

4-Amino-piperidine-1,4-dicarboxylic acid 1-[(4-tert-butyl-phenyl)-amide]-4-p-tolylamide; hydrochloride

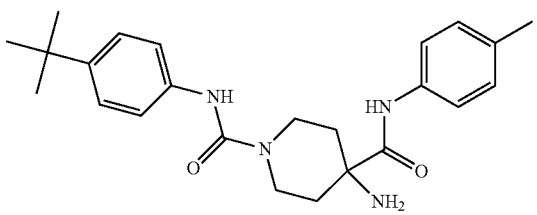

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-tert-butyl-phenylcarbamoyl)-piperidine-4-carboxylic acid methyl ester through cleavage of the ester functionality with KOH and subsequent amide coupling with 4-methyl-aniline (commercially available) followed by the removal of the protecting group with HCl in dioxane to afford the title compound. MS (m/e): 409.4 [(M+H)⁺].

Example 89

4-Amino-piperidine-1,4-dicarboxylic acid 1-[(4-tert-butyl-phenyl)-amide]-4-[(4-isopropyl-phenyl)-amide]; hydrochloride

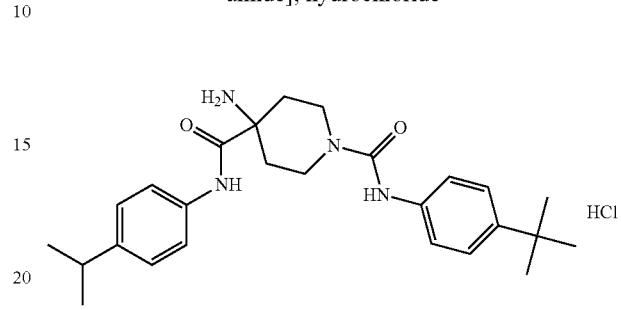

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-tert-butyl-phenylcarbamoyl)-piperidine-4-carboxylic acid methyl ester through cleavage of the ester functionality with KOH and subsequent amide coupling with 4-isopropyl-aniline (commercially available) followed by the removal of the protecting group with HCl in dioxane to afford the title compound. MS (m/e): 437.3 [(M+H)⁺].

Example 90

4-Amino-piperidine-1,4-dicarboxylic acid bis-[(4-tert-butyl-phenyl)-amide]; hydrochloride

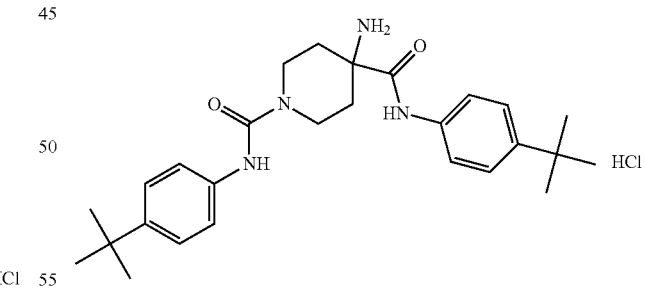

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(4-tert-butyl-phenylcarbamoyl)-piperidine-4-carboxylic acid methyl ester through cleavage of the ester functionality with KOH and subsequent amide coupling with 4-tert.-butyl-aniline (commercially available) followed by the removal of the protecting group with HCl in dioxane to afford the title compound. MS (m/e): 451.3 [(M+H)⁺].

Example 91

4-Amino-1-(2-chloro-benzenesulfonyl)-piperidine-4-carboxylic acid (3-trifluoromethyl-phenyl)-amide

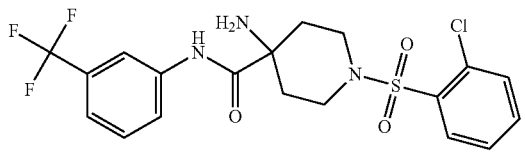 [SMILES: NC1(C(=O)Nc2cccc(C(F)(F)F)c2)CCN(S(=O)(=O)c2ccccc2Cl)CC1]

Step 1

4-tert-Butoxycarbonylamino-1-(2-chloro-benzene-sulfonyl)-piperidine-4-carboxylic acid

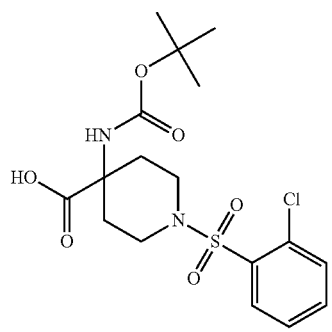 [SMILES: CC(C)(C)OC(=O)NC1(C(=O)O)CCN(S(=O)(=O)c2ccccc2Cl)CC1]

A mixture of 2 g (7.8 mmol) 4-tert-Butoxycarbonylamino-piperidine-4-carboxylic acid methyl ester, 1.72 g (8.1 mmol) 2-chlorobenzenesulfonyl chloride and 2.36 g (23 mmol) NEt₃ in 30 mL DCM was stirred at room temperature over night. DCM and NaHCO₃ aq. was added and the organic phase was dried with MgSO₄ and evaporated. The ester (MS (m/e): 433.3 [(M+H)⁺]) was used without further purification. 3 g of the crude product was dissolved in methanol and 2.7 mL KOH aq. (5M), 30 mL water and 10 mL THF was added and the mixture was stirred at 55° C. for 5 h. The organic solvents were removed under vacuum and acetic acid was added. The mixture was extracted with ethyl acetate and the combined organic phases were washed with water, dried with MgSO₄ and evaporated to yield 2.87 g of the title compound as white foam. MS (m/e): 419.1 [(M+H)⁺]

Step 2

In analogy to the procedure of the synthesis of [4-(4-tert-Butyl-phenylcarbamoyl)-1-(toluene-4-sulfonyl)-piperidin-4-yl]-carbamic acid tert-butyl ester (example 77, step 2) the title compound was prepared from 4-tert-Butoxycarbonylamino-1-(2-chloro-benzenesulfonyl)-piperidine-4-carboxylic acid through amide coupling with 3-trifluoromethyl-aniline (commercially available) followed by the removal of the protecting group with HCl in dioxane to afford the title compound after purification with preparative HPLC on reversed phase eluting with a gradient formed from acetonitrile, water and NEt₃. MS (m/e): 462.1 [(M+H)⁺].

In analogy to the procedure described for the synthesis of 4-Amino-1-(2-chloro-benzenesulfonyl)-piperidine-4-carboxylic acid (3-trifluoromethyl-phenyl)-amide (example 91) further piperidine derivatives have been synthesized through amide coupling with the respective starting materials as mentioned in table 2. The Boc group was cleaved as previously described. Table 2 comprises examples 92 to 105.

TABLE 2

| Ex | Structure | Chemical Name | Starting material |
|---|---|---|---|
| 92 | 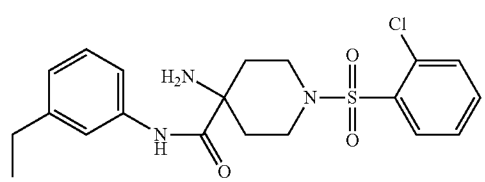 [SMILES: CCc1cccc(NC(=O)C2(N)CCN(S(=O)(=O)c3ccccc3Cl)CC2)c1] | 4-Amino-1-(2-chloro-benzenesulfonyl)-piperidine-4-carboxylic acid (3-ethyl-phenyl)-amide 422.1 | 4-tert-Butoxycarbonyl-amino-1-(2-chloro-benzene-sulfonyl)-piperidine-4-carboxylic acid and 3-Ethyl-phenylamine (commercially available) |
| 93 | 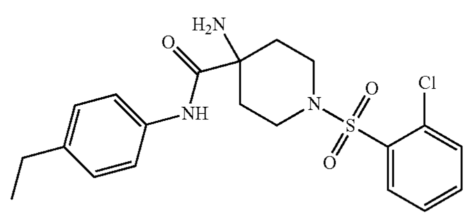 [SMILES: CCc1ccc(NC(=O)C2(N)CCN(S(=O)(=O)c3ccccc3Cl)CC2)cc1] | 4-Amino-1-(2-chloro-benzene-sulfonyl)-piperidine-4-carboxylic acid (4-ethyl-phenyl)-amide 422.1 | 4-tert-Butoxycarbonyl-amino-1-(2-chloro-benzene-sulfonyl)-piperidine-4-carboxylic acid and 4-Ethyl-phenylamine (commercially available) |

TABLE 2-continued

| Ex | Structure | Chemical Name | Starting material |
|---|---|---|---|
| 94 | 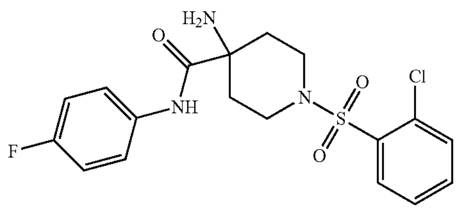 [SMILES: NC1(C(=O)Nc2ccc(F)cc2)CCN(S(=O)(=O)c2ccccc2Cl)CC1] | 4-Amino-1-(2-chloro-benzene-sulfonyl)-piperidine-4-carboxylic acid (4-fluoro-phenyl)-amide 412.1 | 4-tert-Butoxycarbonyl-amino-1-(2-chloro-benzene-sulfonyl)-piperidine-4-carboxylic acid and 4-Fluoro-phenylamine (commercially available) |
| 95 | 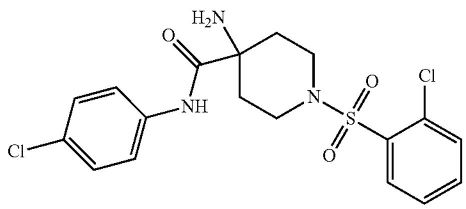 [SMILES: NC1(C(=O)Nc2ccc(Cl)cc2)CCN(S(=O)(=O)c2ccccc2Cl)CC1] | 4-Amino-1-(2-chloro-benzene-sulfonyl)-piperidine-4-carboxylic acid (4-chloro-phenyl)-amide 428.1 | 4-tert-Butoxycarbonyl-amino-1-(2-chloro-benzene-sulfonyl)-piperidine-4-carboxylic acid and 4-Chloro-phenylamine (commercially available) |
| 96 | 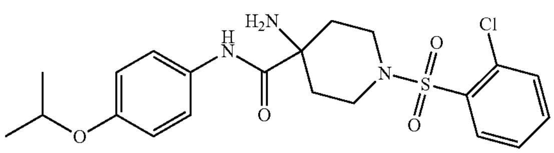 [SMILES: CC(C)Oc1ccc(NC(=O)C2(N)CCN(S(=O)(=O)c3ccccc3Cl)CC2)cc1] | 4-Amino-1-(2-chloro-benzenesulfonyl)-piperidine-4-carboxylic acid (4-isopropoxy-phenyl)-amide 452.2 | 4-tert-Butoxycarbonyl-amino-1-(2-chloro-benzenesulfonyl)-piperidine-4-carboxylic acid and 4-Isopropoxy-phenylamine (commercially available) |
| 97 | 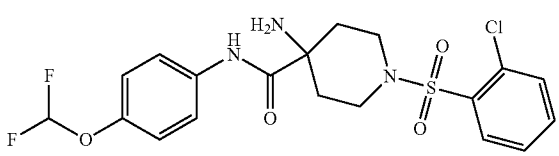 [SMILES: NC1(C(=O)Nc2ccc(OC(F)F)cc2)CCN(S(=O)(=O)c2ccccc2Cl)CC1] | 4-Amino-1-(2-chloro-benzenesulfonyl)-piperidine-4-carboxylic acid (4-difluoromethoxy-phenyl)-amide 460.1 | 4-tert-Butoxycarbonyl-amino-1-(2-chloro-benzenesulfonyl)-piperidine-4-carboxylic acid and 4-Difluoromethoxy-phenylamine (commercially available) |
| 98 | 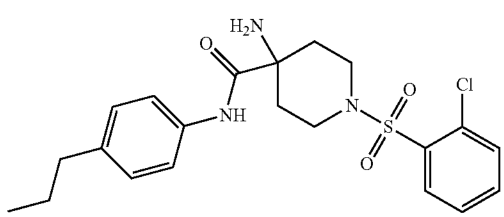 [SMILES: CCCc1ccc(NC(=O)C2(N)CCN(S(=O)(=O)c3ccccc3Cl)CC2)cc1] | 4-Amino-1-(2-chloro-benzenesulfonyl)-piperidine-4-carboxylic acid (4-propyl-phenyl)-amide 436.2 | 4-tert-Butoxycarbonyl-amino-1-(2-chloro-benzenesulfonyl)-piperidine-4-carboxylic acid and 4-Propyl-phenylamine (commercially available) |
| 99 | 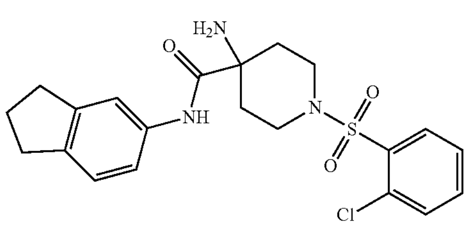 [SMILES: NC1(C(=O)Nc2ccc3c(c2)CCC3)CCN(S(=O)(=O)c2ccccc2Cl)CC1] | 4-Amino-1-(2-chloro-benzenesulfonyl)-piperidine-4-carboxylic acid indan-5-ylamide 434.1 | 4-tert-Butoxycarbonyl-amino-1-(2-chloro-benzenesulfonyl)-piperidine-4-carboxylic acid and Indan-5-ylamine (commercially available) |

TABLE 2-continued

| Ex | Structure | Chemical Name | Starting material |
|---|---|---|---|
| 100 | 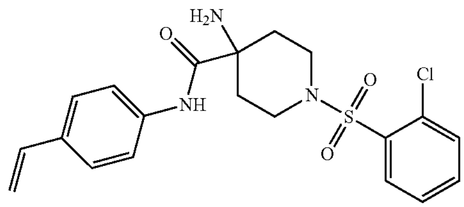 [SMILES: C=Cc1ccc(NC(=O)C2(N)CCN(S(=O)(=O)c3ccccc3Cl)CC2)cc1] | 4-Amino-1-(2-chloro-benzenesulfonyl)-piperidine-4-carboxylic acid (4-vinyl-phenyl)-amide 452.2 | 4-tert-Butoxycarbonyl-amino-1-(2-chloro-benzenesulfonyl)-piperidine-4-carboxylic acid and 4-Vinyl-phenylamine (commercially available) |
| 101 | 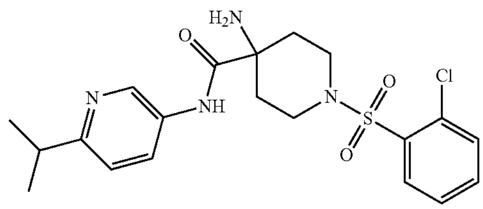 [SMILES: CC(C)c1ccc(NC(=O)C2(N)CCN(S(=O)(=O)c3ccccc3Cl)CC2)cn1] | 4-Amino-1-(2-chloro-benzenesulfonyl)-piperidine-4-carboxylic acid (6-isopropyl-pyridin-3-yl)-amide 437.1 | 4-tert-Butoxycarbonyl-amino-1-(2-chloro-benzenesulfonyl)-piperidine-4-carboxylic acid and 6-Isopropyl-pyridin-3-ylamine (commercially available) |
| 102 | 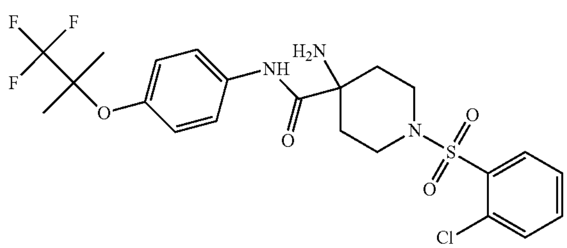 [SMILES: CC(C)(Oc1ccc(NC(=O)C2(N)CCN(S(=O)(=O)c3ccccc3Cl)CC2)cc1)C(F)(F)F] | 4-Amino-1-(2-chloro-benzenesulfonyl)-piperidine-4-carboxylic acid [4-(2,2,2-trifluoro-1,1-dimethyl-ethoxy)-phenyl]-amide 520.2 | 4-tert-Butoxycarbonyl-amino-1-(2-chloro-benzenesulfonyl)-piperidine-4-carboxylic acid and 4-(2,2,2-Trifluoro-1,1-dimethyl-ethyl)-phenylamine (commercially available) |
| 103 | 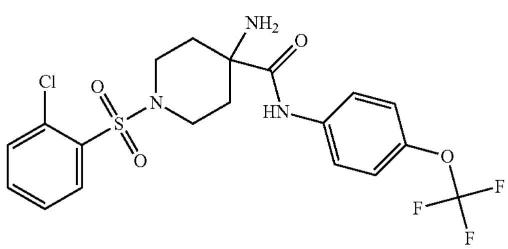 [SMILES: NC1(C(=O)Nc2ccc(OC(F)(F)F)cc2)CCN(S(=O)(=O)c2ccccc2Cl)CC1] | 4-Amino-1-(2-chloro-benzenesulfonyl)-piperidine-4-carboxylic acid (4-trifluoromethoxy-phenyl)-amide 478.1 | 4-tert-Butoxycarbonyl-amino-1-(2-chloro-benzenesulfonyl)-piperidine-4-carboxylic acid and 4-Trifluoromethoxy-phenylamine (commercially available) |
| 104 | 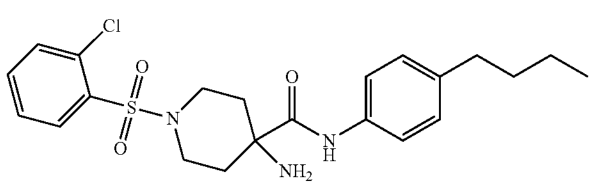 [SMILES: CCCCc1ccc(NC(=O)C2(N)CCN(S(=O)(=O)c3ccccc3Cl)CC2)cc1] | 4-Amino-1-(2-chloro-benzenesulfonyl)-piperidine-4-carboxylic acid (4-butyl-phenyl)-amide 450.2 | 4-tert-Butoxycarbonyl-amino-1-(2-chloro-benzenesulfonyl)-piperidine-4-carboxylic acid and 4-Butyl-phenylamine (commercially available) |
| 105 | 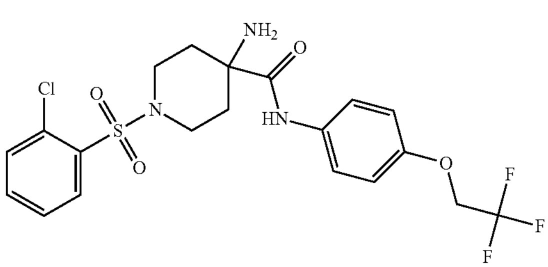 [SMILES: NC1(C(=O)Nc2ccc(OCC(F)(F)F)cc2)CCN(S(=O)(=O)c2ccccc2Cl)CC1] | 4-Amino-1-(2-chloro-benzenesulfonyl)-piperidine-4-carboxylic acid [4-(2,2,2-trifluoro-ethoxy)-phenyl]-amide 492.2 | 4-tert-Butoxycarbonyl-amino-1-(2-chloro-benzenesulfonyl)-piperidine-4-carboxylic acid and 4-(2,2,2-Trifluoro-ethyl)-phenylamine (commercially available) |

Example 106

4-Amino-piperidine-1,4-dicarboxylic acid 1-[(4-fluoro-phenyl)-amide]-4-[(4-isopropyl-phenyl)-amide]; hydrochloride

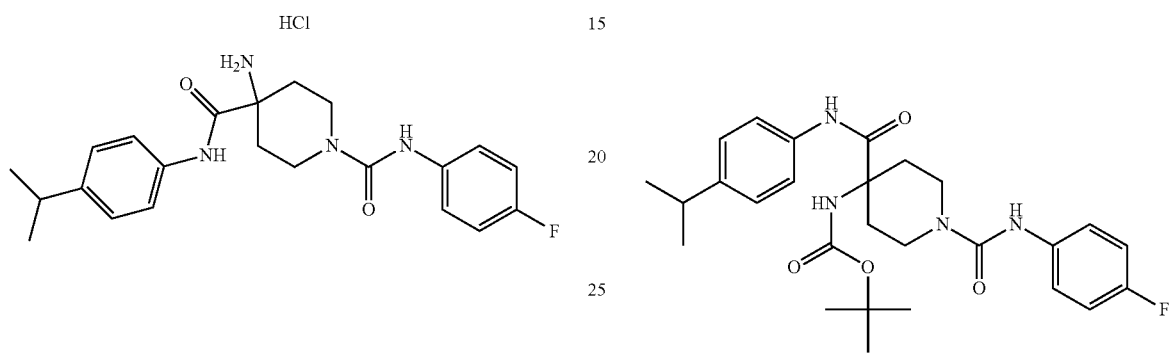

Step 1

[4-(4-Isopropyl-phenylcarbamoyl)-piperidin-4-yl]-carbamic acid tert-butyl ester

A mixture of 2.84 g (6 mmol) 4-tert-Butoxycarbonylamino-4-(4-isopropyl-phenylcarbamoyl)-piperidine-1-carboxylic acid benzyl ester (example 82, step 1) in 80 mL methanol was hydrogenated with H2 over Pd/C (10%) for 2 h at room temperature. The mixture was filtered off and evaporated to dryness to yield 1.94 g (94%) of the title compound as off-white crystals. MS (m/e): 362.4 [(M+H)$^+$].

Step 2

[1-(4-Fluoro-phenylcarbamoyl)-4-(4-isopropyl-phenylcarbamoyl)-piperidin-4-yl]-carbamic acid tert-butyl ester

A mixture of 36 mg (0.1 mmol) [4-(4-Isopropyl-phenylcarbamoyl)-piperidin-4-yl]-carbamic acid tert-butyl ester, 16.5 mg (0.12 mmol) 4-fluorophenyl isocyanate and 32 mg (0.31 mmol) NEt$_3$ in 1 mL DCM was shaken at room temperature over night. After evaporation to dryness the residue was subjected to purification by preparative HPLC on reversed phase eluting with a gradient formed from acetonitrile, water and HCOOH. The product containing fractions were evaporated to yield 38.5 mg (77%) of the title compound. MS (m/e): 499.3 [(M+H)$^+$].

Step 3

In analogy to the procedure described for the removal of the Boc-group (example 77, step 3) the protecting group was removed with HCl in dioxane to afford the title compound. MS (m/e): 399.2 [(M+H)$^+$].

In analogy to the procedure described for the synthesis of 4-Amino-piperidine-1,4-dicarboxylic acid 1-[(4-fluoro-phenyl)-amide]-4-[(4-isopropyl-phenyl)-amide]; hydrochloride (example 106) further piperidine derivatives have been synthesized from the respective starting materials as mentioned in table 3. The removal of the Boc group was done in analogy to the procedures as previously described. In the cases were the final compounds were obtained as crystals (hydrochloride salts) the compounds were filtered off, washed with diethyl ether and dried. In the other cases the mixtures were evaporated and the residues were purified by preparative HPLC on reversed phase eluting with a gradient formed from acetonitrile, water and either NEt$_3$ or HCOOH. The product containing fractions were evaporated. The final products are shown in table 3 and comprise examples 107 to 131.

TABLE 3

| Ex | Structure | Chemical Name | Starting material |
|---|---|---|---|
| 107 | 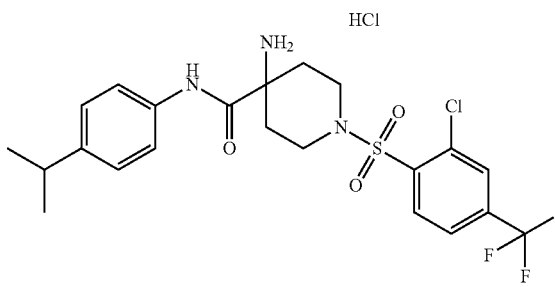 | 4-Amino-piperidine-1,4-dicarboxylic acid bis-[(4-isopropyl-phenyl)-amide]; hydrochloride 423.3 | [4-(4-Isopropyl-phenylcarbamoyl)-piperidin-4-yl]-carbamic acid tert-butyl ester and 1-Isocyanato-4-isopropyl-benzene (commercially available) |
| 108 | 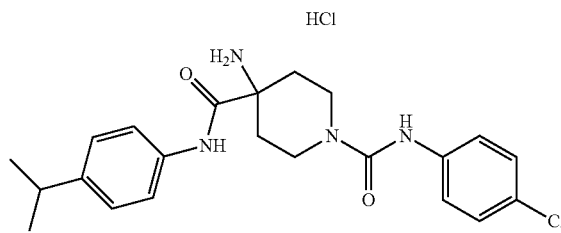 | 4-Amino-piperidine-1,4-dicarboxylic acid 1-[(4-chloro-phenyl)-amide] 4-[(4-isopropyl-phenyl)-amide]; hydrochloride 415.3 | [4-(4-Isopropyl-phenylcarbamoyl)-piperidin-4-yl]-carbamic acid tert-butyl ester and 1-Chloro-4-isocyanato-benzene (commercially available) |
| 109 | 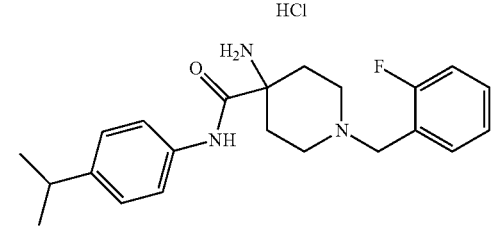 [SMILES: Cl ; CC(C)c1ccc(NC(=O)C2(N)CCN(Cc3ccccc3Cl)CC2)cc1] | 4-Amino-1-(2-fluoro-benzyl)-piperidine-4-carboxylic acid (4-isopropyl-phenyl)-amide; hydrochloride 370.2 | [4-(4-Isopropyl-phenylcarbamoyl)-piperidin-4-yl]-carbamic acid tert-butyl ester and 1-Bromomethyl-2-fluoro-benzene (commercially available) |
| 110 | 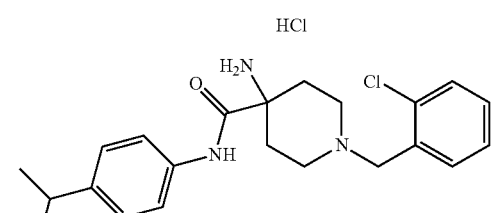 | 4-Amino-1-(2-chloro-benzyl)-piperidine-4-carboxylic acid (4-isopropyl-phenyl)-amide; hydrochloride 386.2 | [4-(4-Isopropyl-phenylcarbamoyl)-piperidin-4-yl]-carbamic acid tert-butyl ester and 1-Bromomethyl-2-chloro-benzene (commercially available) |
| 111 | 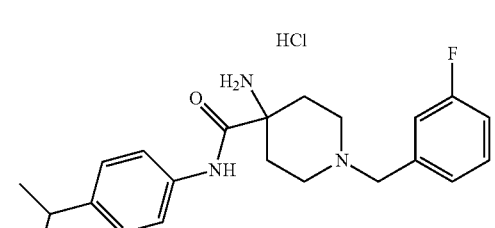 | 4-Amino-1-(3-fluoro-benzyl)-piperidine-4-carboxylic acid (4-isopropyl-phenyl)-amide; hydrochloride 370.3 | [4-(4-Isopropyl-phenylcarbamoyl)-piperidin-4-yl]-carbamic acid tert-butyl ester and 1-Bromomethyl-3-fluoro-benzene (commercially available) |
| 112 | 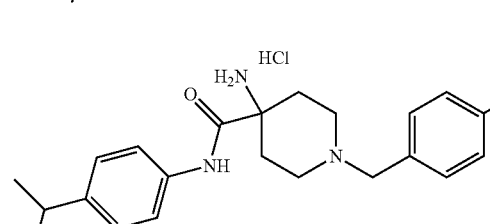 | 4-Amino-1-(4-trifluoromethyl-benzyl)-piperidine-4-carboxylic acid (4-isopropyl-phenyl)-amide; hydrochloride 420.2 | [4-(4-Isopropyl-phenylcarbamoyl)-piperidin-4-yl]-carbamic acid tert-butyl ester and 1-Bromomethyl-4-trifluoromethyl-benzene (commercially available) |

TABLE 3-continued

| Ex | Structure | Chemical Name | Starting material |
|---|---|---|---|
| 113 | 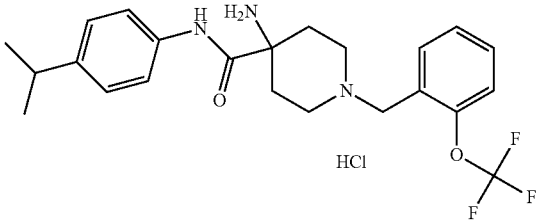 [SMILES: CC(C)c1ccc(NC(=O)C2(N)CCN(Cc3ccccc3OC(F)(F)F)CC2)cc1 ; Cl] | 4-Amino-1-(2-trifluoromethoxy-benzyl)-piperidine-4-carboxylic acid (4-isopropyl-phenyl)-amide; hydrochloride 436.3 | [4-(4-Isopropyl-phenylcarbamoyl)-piperidin-4-yl]-carbamic acid tert-butyl ester and 1-Bromomethyl-2-trifluoromethoxy-benzene (commercially available) |
| 114 | 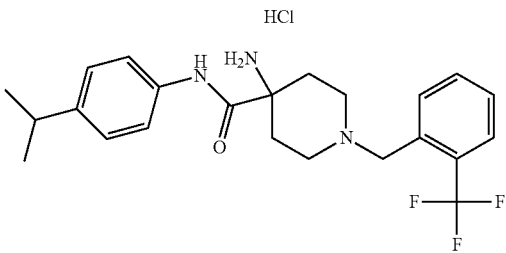 [SMILES: Cl ; CC(C)c1ccc(NC(=O)C2(N)CCN(Cc3ccccc3C(F)(F)F)CC2)cc1] | 4-Amino-1-(2-trifluoromethyl-benzyl)-piperidine-4-carboxylic acid (4-isopropyl-phenyl)-amide; hydrochloride 420.2 | [4-(4-Isopropyl-phenylcarbamoyl)-piperidin-4-yl]-carbamic acid tert-butyl ester and 1-Bromomethyl-2-trifluoromethyl-benzene (commercially available) |
| 115 | 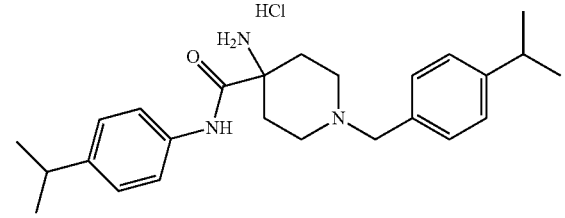 [SMILES: Cl ; CC(C)c1ccc(CN2CCC(N)(C(=O)Nc3ccc(C(C)C)cc3)CC2)cc1] | 4-Amino-1-(4-isopropyl-benzyl)-piperidine-4-carboxylic acid (4-isopropyl-phenyl)-amide; hydrochloride 394.3 | [4-(4-Isopropyl-phenylcarbamoyl)-piperidin-4-yl]-carbamic acid tert-butyl ester and 1-Bromomethyl-4-isopropyl-benzene (commercially available) |
| 116 | 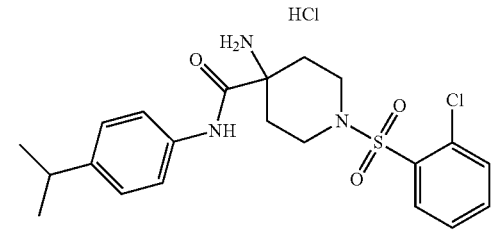 [SMILES: Cl ; CC(C)c1ccc(NC(=O)C2(N)CCN(S(=O)(=O)c3ccccc3Cl)CC2)cc1] | 4-Amino-1-(2-chloro-benzenesulfonyl)-piperidine-4-carboxylic acid (4-isopropyl-phenyl)-amide; hydrochloride 436.2 | [4-(4-Isopropyl-phenylcarbamoyl)-piperidin-4-yl]-carbamic acid tert-butyl ester and 2-Chloro-benzenesulfonyl chloride (commercially available) |
| 117 | 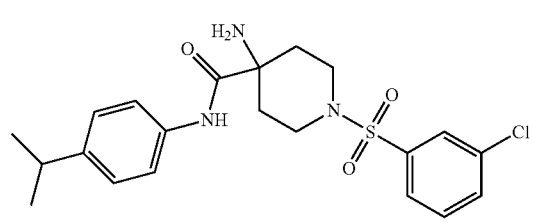 [SMILES: CC(C)c1ccc(NC(=O)C2(N)CCN(S(=O)(=O)c3cccc(Cl)c3)CC2)cc1] | 4-Amino-1-(3-chloro-benzenesulfonyl)-piperidine-4-carboxylic acid (4-isopropyl-phenyl)-amide 436.3 | [4-(4-Isopropyl-phenylcarbamoyl)-piperidin-4-yl]-carbamic acid tert-butyl ester and 3-Chloro-benzenesulfonyl chloride (commercially available) |
| 118 | 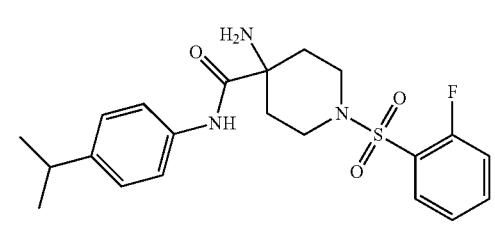 | 4-Amino-1-(2-fluoro-benzenesulfonyl)-piperidine-4-carboxylic acid (4-isopropyl-phenyl)-amide 420.2 | [4-(4-Isopropyl-phenylcarbamoyl)-piperidin-4-yl]-carbamic acid tert-butyl ester and 2-Fluoro-benzenesulfonyl chloride (commercially available) |

TABLE 3-continued

| Ex | Structure | Chemical Name | Starting material |
|---|---|---|---|
| 119 | 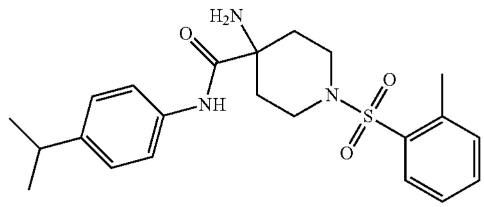 [SMILES: Cc1ccccc1S(=O)(=O)N1CCC(N)(C(=O)Nc2ccc(C(C)C)cc2)CC1] | 4-Amino-1-(toluene-2-sulfonyl)-piperidine-4-carboxylic acid (4-isopropyl-phenyl)-amide 416.3 | [4-(4-Isopropyl-phenylcarbamoyl)-piperidin-4-yl]-carbamic acid tert-butyl ester and 2-Methyl-benzenesulfonyl chloride (commercially available) |
| 120 | HCl | 4-Amino-1-(2-methyl-propane-1-sulfonyl)-piperidine-4-carboxylic acid (4-isopropyl-phenyl)-amide; hydrochloride 382.4 | [4-(4-Isopropyl-phenylcarbamoyl)-piperidin-4-yl]-carbamic acid tert-butyl ester and 2-Methyl-propane-1-sulfonyl chloride (commercially available) |
| 121 | HCl | 4-Amino-1-(4-fluoro-benzyl)-piperidine-4-carboxylic acid (4-isopropyl-phenyl)-amide; hydrochloride 370.2 | [4-(4-Isopropyl-phenylcarbamoyl)-piperidin-4-yl]-carbamic acid tert-butyl ester and 1-Bromomethyl-4-fluoro-benzene (commercially available) |
| 122 | 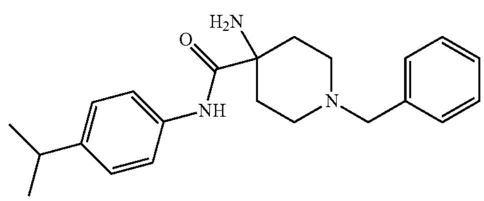 [SMILES: CC(C)c1ccc(NC(=O)C2(N)CCN(Cc3ccccc3)CC2)cc1] | 4-Amino-1-benzyl-piperidine-4-carboxylic acid (4-isopropyl-phenyl)-amide 352.4 | [4-(4-Isopropyl-phenylcarbamoyl)-piperidin-4-yl]-carbamic acid tert-butyl ester and Bromomethyl-benzene (commercially available) |
| 123 | 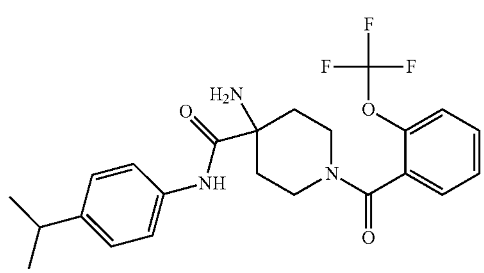 [SMILES: CC(C)c1ccc(NC(=O)C2(N)CCN(C(=O)c3ccccc3OC(F)(F)F)CC2)cc1] | 4-Amino-1-(2-trifluoromethoxy-benzoyl)-piperidine-4-carboxylic acid (4-isopropyl-phenyl)-amide 450.2 | [4-(4-Isopropyl-phenylcarbamoyl)-piperidin-4-yl]-carbamic acid tert-butyl ester and 2-Trifluoromethoxy-benzoyl chloride (commercially available) |
| 124 | 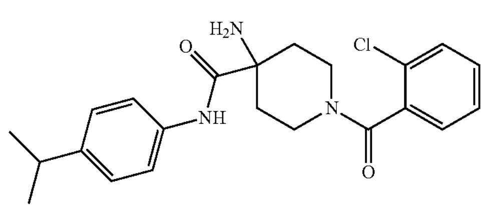 [SMILES: CC(C)c1ccc(NC(=O)C2(N)CCN(C(=O)c3ccccc3Cl)CC2)cc1] | 4-Amino-1-(2-chloro-benzoyl)-piperidine-4-carboxylic acid (4-isopropyl-phenyl)-amide 400.1 | [4-(4-Isopropyl-phenylcarbamoyl)-piperidin-4-yl]-carbamic acid tert-butyl ester and 2-Chloro-benzoyl chloride (commercially available) |
| 125 | 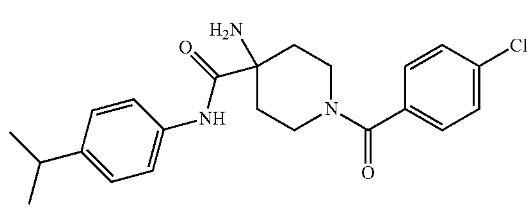 [SMILES: CC(C)c1ccc(NC(=O)C2(N)CCN(C(=O)c3ccc(Cl)cc3)CC2)cc1] | 4-Amino-1-(4-chloro-benzoyl)-piperidine-4-carboxylic acid (4-isopropyl-phenyl)-amide 400.1 | [4-(4-Isopropyl-phenylcarbamoyl)-piperidin-4-yl]-carbamic acid tert-butyl ester and 4-Chloro-benzoyl chloride (commercially available) |

TABLE 3-continued

| Ex | Structure | Chemical Name | Starting material |
|---|---|---|---|
| 126 | 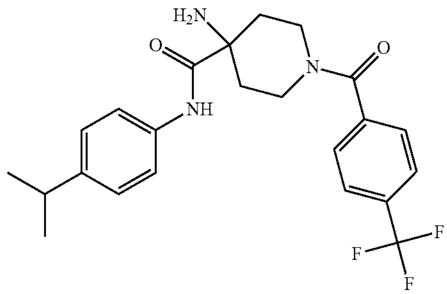 [SMILES: CC(C)c1ccc(NC(=O)C2(N)CCN(C(=O)c3ccc(C(F)(F)F)cc3)CC2)cc1] | 4-Amino-1-(4-trifluoromethyl-benzoyl)-piperidine-4-carboxylic acid (4-isopropyl-phenyl)-amide<br>434.4 | [4-(4-Isopropyl-phenylcarbamoyl)-piperidin-4-yl]-carbamic acid tert-butyl ester and 4-Trifluoromethyl-benzoyl chloride (commerically available) |
| 127 | 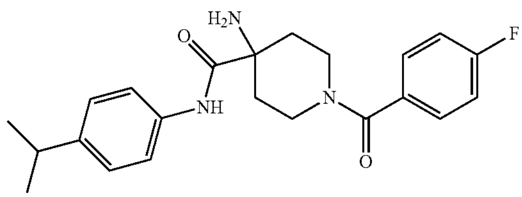 [SMILES: CC(C)c1ccc(NC(=O)C2(N)CCN(C(=O)c3ccc(F)cc3)CC2)cc1] | 4-Amino-1-(4-fluoro-benzoyl)-piperidine-4-carobxylic acid (4-isopropyl-phenyl)-amide<br>384.2 | [4-(4-Isopropyl-phenylcarbamoyl)-piperidin-4-yl]-carbamic acid tert-butyl ester and 4-Fluoro-benzoyl chloride (commercially available) |
| 128 | 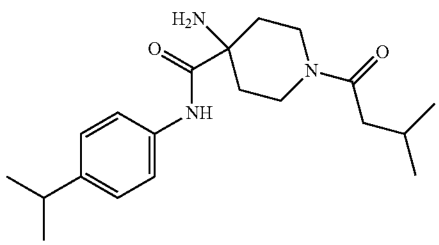 [SMILES: CC(C)CC(=O)N1CCC(N)(C(=O)Nc2ccc(C(C)C)cc2)CC1] | 4-Amino-1-(3-methyl-butyryl)-piperidine-4-carboxylic acid (4-isopropyl-phenyl)-amide<br>346.2 | [4-(4-Isopropyl-phenylcarbamoyl)-piperidin-4-yl]-carbamic acid tert-butyl ester and 3-Methyl-butyryl chloride (commercially available) |
| 129 | 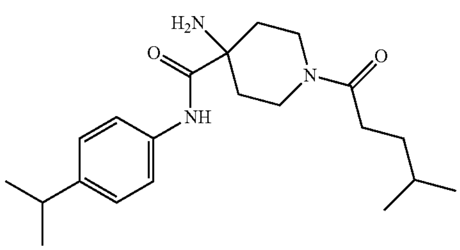 [SMILES: CC(C)CCC(=O)N1CCC(N)(C(=O)Nc2ccc(C(C)C)cc2)CC1] | 4-Amino-1-(4-methyl-pentanoyl)-piperidine-4-carboxylic acid (4-isopropyl-phenyl)-amide<br>360.4 | [4-(4-Isopropyl-phenylcarbamoyl)-piperidin-4-yl]-carbamic acid tert-butyl ester and 4-Methyl-pentanoyl chloride (commercially available) |
| 130 | 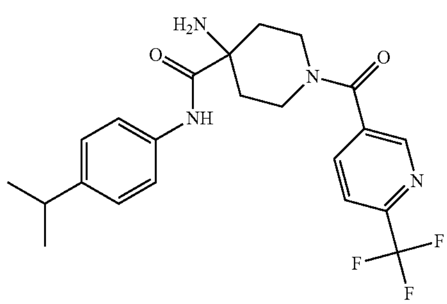 [SMILES: CC(C)c1ccc(NC(=O)C2(N)CCN(C(=O)c3ccc(C(F)(F)F)nc3)CC2)cc1] | 4-Amino-1-(6-trifluoromethyl-pyridine-3-carbonyl)-piperidine-4-carboxylic acid (4-isopropyl-phenyl)-amide<br>435.2 | [4-(4-Isopropyl-phenylcarbamoyl)-piperidin-4-yl]-carbamic acid tert-butyl ester and 6-Trifluoromethyl-nicotinoyl chloride (commercially available) |
| 131 | 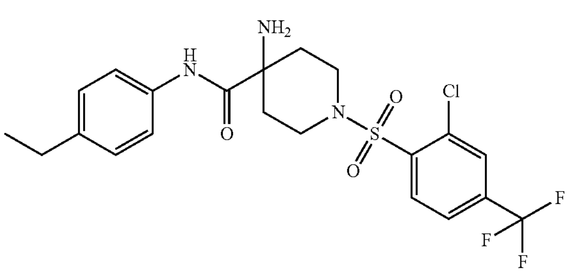 [SMILES: CCc1ccc(NC(=O)C2(N)CCN(S(=O)(=O)c3ccc(C(F)(F)F)cc3Cl)CC2)cc1] | 4-Amino-1-(2-chloro-4-trifluoromethyl-benzenesulfonyl)-piperidine-4-carboxylic acid (4-isopropyl-phenyl)-amide<br>504.1 | [4-(4-Isopropyl-phenylcarbamoyl)-piperidin-4-yl]-carbamic acid tert-butyl ester and 2-Chloro-4-trifluoromethyl-benzenesulfonyl chloride (commercially available) |

Example 132

4-Amino-4-(4-ethyl-phenylcarbamoyl)-piperidine-1-carboxylic acid benzyl ester

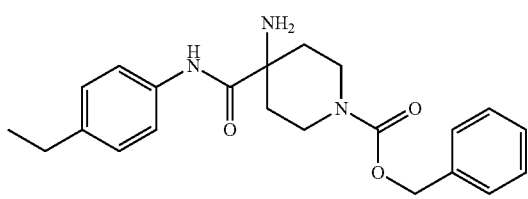 [SMILES: CCc1ccc(NC(=O)C2(N)CCN(C(=O)OCc3ccccc3)CC2)cc1]

Step 1

4-tert-Butoxycarbonylamino-4-(4-ethyl-phenylcarbamoyl)-piperidine-1-carboxylic acid benzyl ester

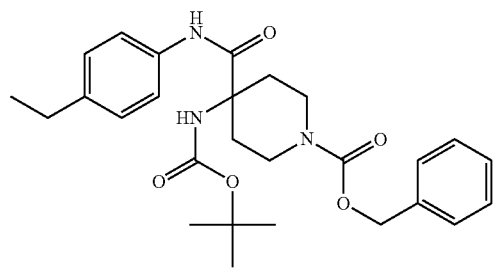

In analogy to the procedure described for the synthesis of 4-tert-Butoxycarbonylamino-4-(4-isopropyl-phenylcarbamoyl)-piperidine-1-carboxylic acid benzyl ester (example 82, step 1) the title compound was prepared from 4-tert-Butoxycarbonylamino-piperidine-1,4-dicarboxylic acid monobenzyl ester (commercially available) and 4-ethylphenylamine. MS (m/e): 482.4 [(M+H)$^+$].

Step 2

In analogy to the procedure described for the removal of the Boc-group (example 77, step 3) the Boc group was removed with HCl in dioxane to afford after purification by preparative HPLC on reversed phase eluting with a gradient formed from acetonitrile, water and NEt$_3$ the title compound as white crystals. MS (m/e): 382.4 [(M+H)$^+$].

Example 133

4-Amino-1-benzenesulfonyl-piperidine-4-carboxylic acid (4-ethyl-phenyl)-amide

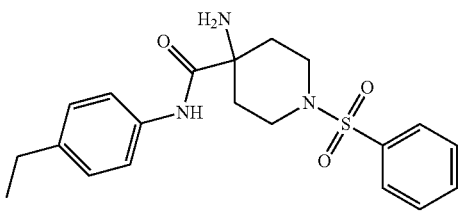 [SMILES: CCc1ccc(NC(=O)C2(N)CCN(S(=O)(=O)c3ccccc3)CC2)cc1]

Step 1

[4-(4-Ethyl-phenylcarbamoyl)-piperidin-4-yl]-carbamic acid tert-butyl ester

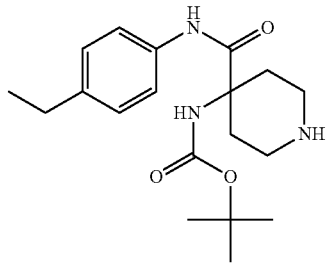

A solution of 2.86 g (5.9 mmol) 4-tert-Butoxycarbonylamino-4-(4-ethyl-phenylcarbamoyl)-piperidine-1-carboxylic acid benzyl ester (example 132, step 1) in 70 mL methanol was hydrogenated over 290 mg Pd/C (10%) with H2 (1 bar) for 2 h at room temperature. After filtration the filtrate was evaporated to dryness to yield after drying under high vacuum 2.05 g (99%) of the title compound as off-white solid. MS (m/e): 348.3 [(M+H)$^+$].

Step 2

A mixture of 29.8 mg (0.086 mmol) [4-(4-Ethyl-phenylcarbamoyl)-piperidin-4-yl]-carbamic acid tert-butyl ester, 16.8 mg (0.095 mmol) Benzenesulfonyl chloride and 17 mg (0.172 mmol) NEt$_3$ in 1 mL DCM was stirred for 1-1.5 h at room temperature. 0.216 mL HCl (4N in dioxane) was added and the mixture was heated to 45° C. over night. After evaporation the residue was subjected to purification by preparative HPLC on reversed phase eluting with a gradient formed from acetonitrile, water and NEt$_3$ to yield after evaporation of the product containing fractions 5.2 mg (9%) of the title compound. MS (m/e): 388.2 [(M+H)$^+$].

In analogy to the procedure described for the synthesis of 4-Amino-1-benzenesulfonyl-piperidine-4-carboxylic acid (4-ethyl-phenyl)-amide (example 133) further piperidine derivatives have been synthesized from the respective starting materials as mentioned in table 4. Table 4 comprises examples 134-159.

TABLE 4

| Ex | Structure | Chemical Name | Starting material |
|---|---|---|---|
| 134 | 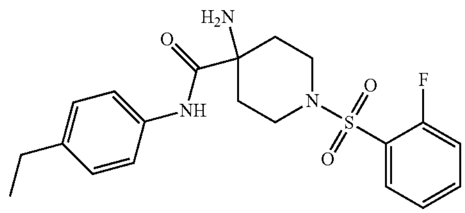 [SMILES: CCc1ccc(NC(=O)C2(N)CCN(S(=O)(=O)c3ccccc3F)CC2)cc1] | 4-Amino-1-(2-fluoro-benzenesulfonyl)-piperidine-4-carboxylic acid (4-ethyl-phenyl)-amide 406.2 | [4-(4-Ethyl-phenylcarbamoyl)-piperidin-4-yl]-carbamic acid tert-butyl ester and 2-Fluoro-benzenesulfonyl chloride (commercially available) |
| 135 | 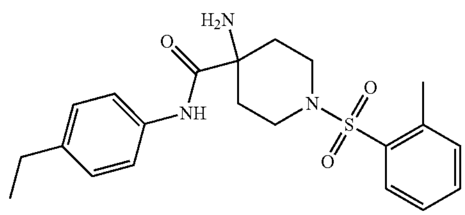 [SMILES: CCc1ccc(NC(=O)C2(N)CCN(S(=O)(=O)c3ccccc3C)CC2)cc1] | 4-Amino-1-(toluene-2-sulfonyl)-piperidine-4-carboxylic acid (4-ethyl-phenyl)-amide 402.2 | [4-(4-Ethyl-phenylcarbamoyl)-piperidin-4-yl]-carbamic acid tert-butyl ester and 2-Methyl-benzenesulfonyl chloride (commercially available) |
| 136 | 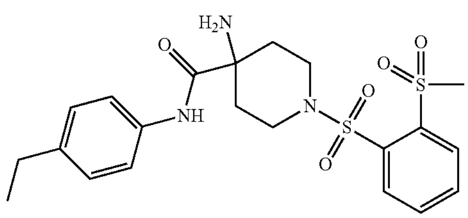 [SMILES: CCc1ccc(NC(=O)C2(N)CCN(S(=O)(=O)c3ccccc3S(C)(=O)=O)CC2)cc1] | 4-Amino-1-(2-methanesulfonyl-benzenesulfonyl)-piperidine-4-carboxylic acid (4-ethyl-phenyl)-amide 466.3 | [4-(4-Ethyl-phenylcarbamoyl)-piperidin-4-yl]-carbamic acid tert-butyl ester and 2-Methanesulfonyl-benzenesulfonyl chloride (commercially available) |
| 137 | 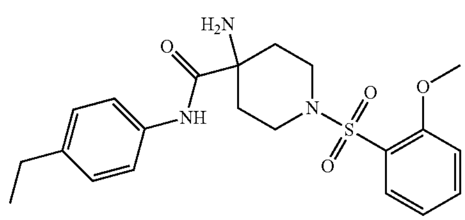 [SMILES: CCc1ccc(NC(=O)C2(N)CCN(S(=O)(=O)c3ccccc3OC)CC2)cc1] | 4-Amino-1-(2-methoxy-benzenesulfonyl)-piperidine-4-carboxylic acid (4-ethyl-phenyl)-amide 418.2 | [4-(4-Ethyl-phenylcarbamoyl)-piperidin-4-yl]-carbamic acid tert-butyl ester and 2-Methoxy-benzenesulfonyl chloride (commercially available) |
| 138 | 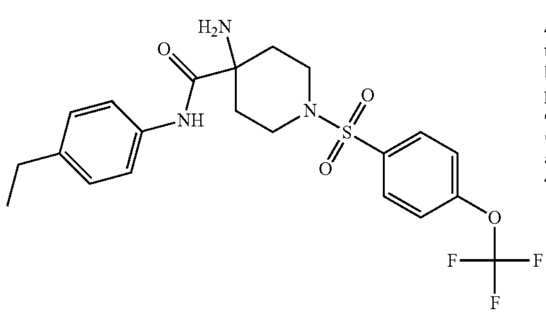 [SMILES: CCc1ccc(NC(=O)C2(N)CCN(S(=O)(=O)c3ccc(OC(F)(F)F)cc3)CC2)cc1] | 4-Amino-1-(4-trifluoromethoxy-benzenesulfonyl)-piperidine-4-carboxylic acid (4-ethyl-phenyl)-amide 472.3 | [4-(4-Ethyl-phenylcarbamoyl)-piperidin-4-yl]-carbamic acid tert-butyl ester and 4-Trifluoromethoxy-benzenesulfonyl chloride (commercially available) |
| 139 | 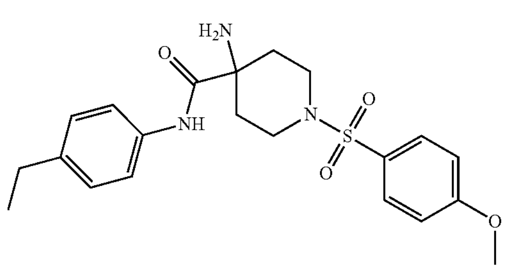 [SMILES: CCc1ccc(NC(=O)C2(N)CCN(S(=O)(=O)c3ccc(OC)cc3)CC2)cc1] | 4-Amino-1-(4-methoxy-benzenesulfonyl)-piperidine-4-carboxylic acid (4-ethyl-phenyl)-amide 418.2 | [4-(4-Ethyl-phenylcarbamoyl)-piperidin-4-yl]-carbamic acid tert-butyl ester and 4-Methoxy-benzenesulfonyl chloride (commercially available) |

TABLE 4-continued

| Ex | Structure | Chemical Name | Starting material |
|---|---|---|---|
| 140 | 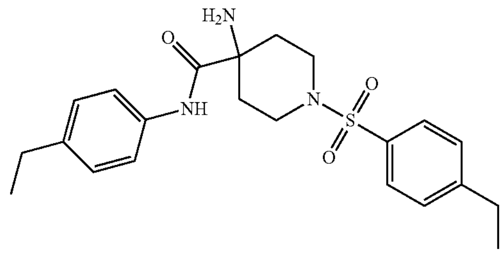 [SMILES: CCc1ccc(NC(=O)C2(N)CCN(S(=O)(=O)c3ccc(CC)cc3)CC2)cc1] | 4-Amino-1-(4-ethyl-benzenesulfonyl)-piperidine-4-carboxylic acid (4-ethyl-phenyl)-amide 416.3 | [4-(4-Ethyl-phenylcarbamoyl)-piperidin-4-yl]-carbamic acid tert-butyl ester and 4-Ethyl-benzenesulfonyl chloride (commercially available) |
| 141 | 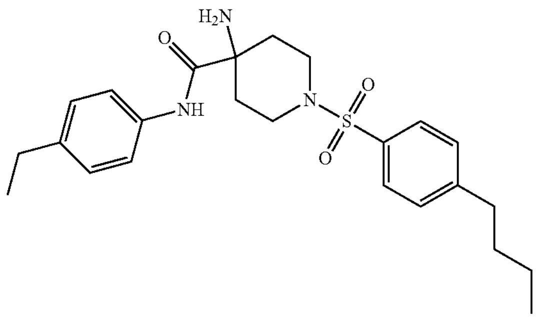 [SMILES: CCCCc1ccc(S(=O)(=O)N2CCC(N)(C(=O)Nc3ccc(CC)cc3)CC2)cc1] | 4-Amino-1-(4-butyl-benzenesulfonyl)-piperidine-4-carboxylic acid (4-ethyl-phenyl)-amide 444.3 | [4-(4-Ethyl-phenylcarbamoyl)-piperidin-4-yl]-carbamic acid tert-butyl ester and 4-Butyl-benzenesulfonyl chloride (commercially available) |
| 142 | 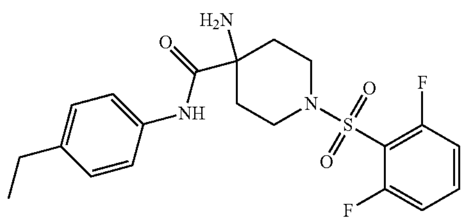 [SMILES: CCc1ccc(NC(=O)C2(N)CCN(S(=O)(=O)c3c(F)cccc3F)CC2)cc1] | 4-Amino-1-(2,6-difluoro-benzenesulfonyl)-piperidine-4-carboxylic acid (4-ethyl-phenyl)-amide 424.2 | [4-(4-Ethyl-phenylcarbamoyl)-piperidin-4-yl]-carbamic acid tert-butyl ester and 2,6-Difluoro-benzenesulfonyl chloride (commercially available) |
| 143 | 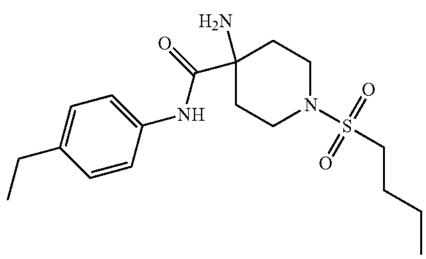 [SMILES: CCCCS(=O)(=O)N1CCC(N)(C(=O)Nc2ccc(CC)cc2)CC1] | 4-Amino-1-(butane-1-sulfonyl)-piperidine-4-carboxylic acid (4-ethyl-phenyl)-amide 368.2 | [4-(4-Ethyl-phenylcarbamoyl)-piperidin-4-yl]-carbamic acid tert-butyl ester and Butane-1-sulfonyl chloride (commercially available) |
| 144 | 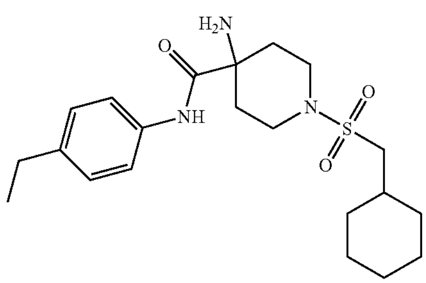 [SMILES: CCc1ccc(NC(=O)C2(N)CCN(S(=O)(=O)CC3CCCCC3)CC2)cc1] | 4-Amino-1-cyclohexyl-methane sulfonyl-piperidine-4-carboxylic acid (4-ethyl-phenyl)-amide 408.3 | [4-(4-Ethyl-phenylcarbamoyl)-piperidin-4-yl]-carbamic acid tert-butyl ester and Cyclohexyl-methanesulfonyl chloride (commercially available) |
| 145 | 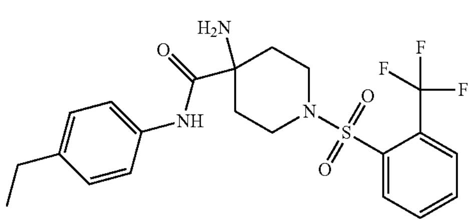 [SMILES: CCc1ccc(NC(=O)C2(N)CCN(S(=O)(=O)c3ccccc3C(F)(F)F)CC2)cc1] | 4-Amino-1-(2-trifluoromethyl-benzenesulfonyl)-piperidine-4-carboxylic acid (4-ethyl-phenyl)-amide 456.3 | [4-(4-Ethyl-phenylcarbamoyl)-piperidin-4-yl]-carbamic acid tert-butyl ester and 2-Trifluoromethyl-benzenesulfonyl chloride (commercially available) |

TABLE 4-continued

| Ex | Structure | Chemical Name | Starting material |
|---|---|---|---|
| 146 | 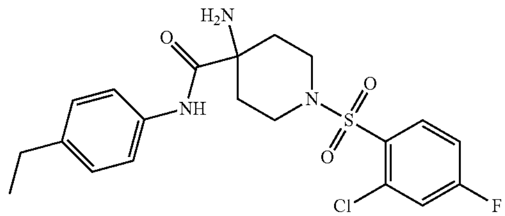 [SMILES: CCc1ccc(NC(=O)C2(N)CCN(S(=O)(=O)c3ccc(F)cc3Cl)CC2)cc1] | 4-Amino-1-(2-chloro-4-fluoro-benzenesulfonyl)-piperidine-4-carboxylic acid (4-ethyl-phenyl)-amide 440.2 | [4-(4-Ethyl-phenylcarbamoyl)-piperidin-4-yl]-carbamic acid tert-butyl ester and 2-Chloro-4-fluoro-benzenesulfonyl chloride (commercially available) |
| 147 | 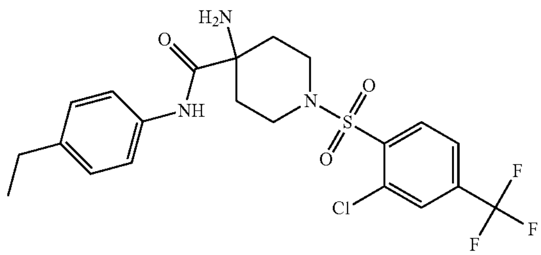 [SMILES: CCc1ccc(NC(=O)C2(N)CCN(S(=O)(=O)c3ccc(C(F)(F)F)cc3Cl)CC2)cc1] | 4-Amino-1-(2-chloro-4-trifluoromethyl-benzenesulfonyl)-piperidine-4-carboxylic acid (4-ethyl-phenyl)-amide 490.2 | [4-(4-Ethyl-phenylcarbamoyl)-piperidin-4-yl]-carbamic acid tert-butyl ester and 2-Chloro-4-trifluoromethyl-benzenesulfonyl chloride (commercially available) |
| 148 | 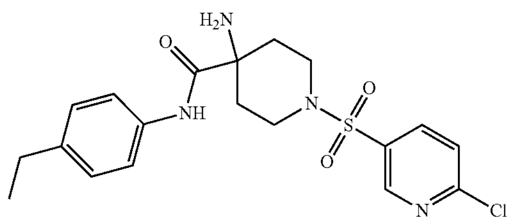 [SMILES: CCc1ccc(NC(=O)C2(N)CCN(S(=O)(=O)c3ccc(Cl)nc3)CC2)cc1] | 4-Amino-1-(6-chloro-pyridine-3-sulfonyl)-piperidine-4-carboxylic acid (4-ethyl-phenyl)-amide 423.2 | [4-(4-Ethyl-phenylcarbamoyl)-piperidin-4-yl]-carbamic acid tert-butyl ester and 6-Chloro-pyridine-3-sulfonyl chloride (commercially available) |
| 149 | 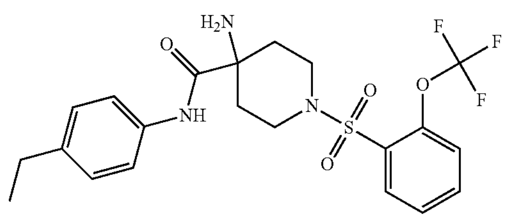 [SMILES: CCc1ccc(NC(=O)C2(N)CCN(S(=O)(=O)c3ccccc3OC(F)(F)F)CC2)cc1] | 4-Amino-1-(2-trifluoromethoxy-benzenesulfonyl)-piperidine-4-carboxylic acid (4-ethyl-phenyl)-amide 472.2 | [4-(4-Ethyl-phenylcarbamoyl)-piperidin-4-yl]-carbamic acid tert-butyl ester and 2-Trifluoromethoxy-benzenesulfonyl chloride (commercially available) |
| 150 | 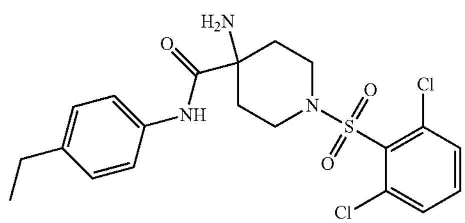 [SMILES: CCc1ccc(NC(=O)C2(N)CCN(S(=O)(=O)c3c(Cl)cccc3Cl)CC2)cc1] | 4-Amino-1-(2,6-dichloro-benzenesulfonyl)-piperidine-4-carboxylic acid (4-ethyl-phenyl)-amide 456.2 | [4-(4-Ethyl-phenylcarbamoyl)-piperidin-4-yl]-carbamic acid tert-butyl ester and 2,6-Dichloro-benzenesulfonyl chloride (commercially available) |
| 151 | 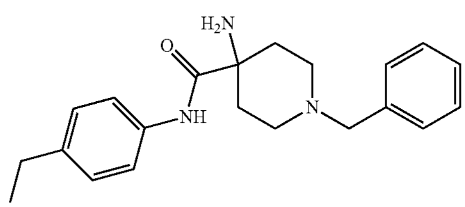 [SMILES: CCc1ccc(NC(=O)C2(N)CCN(Cc3ccccc3)CC2)cc1] | 4-Amino-1-benzyl-piperidine-4-carboxylic acid (4-ethyl-phenyl)-amide 338.3 | [4-(4-Ethyl-phenylcarbamoyl)-piperidin-4-yl]-carbamic acid tert-butyl ester and Bromomethyl-benzene (commercially available) |
| 152 | 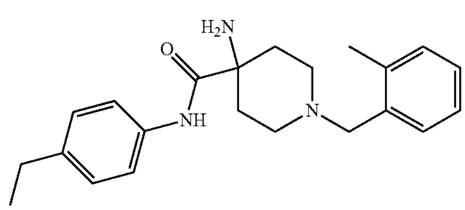 [SMILES: CCc1ccc(NC(=O)C2(N)CCN(Cc3ccccc3C)CC2)cc1] | 4-Amino-1-(2-methyl-benzyl)-piperidine-4-carboxylic acid (4-ethyl-phenyl)-amide 352.4 | [4-(4-Ethyl-phenylcarbamoyl)-piperidin-4-yl]-carbamic acid tert-butyl ester and 1-Bromomethyl-2-methyl-benzene (commercially available) |

TABLE 4-continued

| Ex | Structure | Chemical Name | Starting material |
|---|---|---|---|
| 153 | 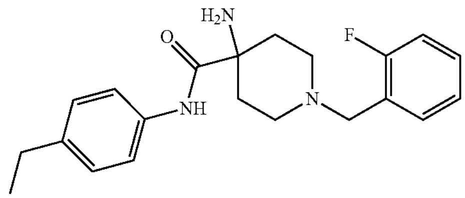 [SMILES: CCc1ccc(NC(=O)C2(N)CCN(Cc3ccccc3F)CC2)cc1] | 4-Amino-1-(2-fluoro-benzyl)-piperidine-4-carboxylic acid (4-ethyl-phenyl)-amide 356.3 | [4-(4-Ethyl-phenylcarbamoyl)-piperidin-4-yl]-carbamic acid tert-butyl ester and 1-Bromomethyl-2-fluoro-benzene (commercially available) |
| 154 | 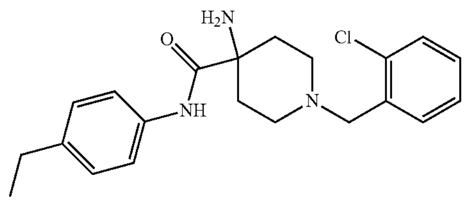 [SMILES: CCc1ccc(NC(=O)C2(N)CCN(Cc3ccccc3Cl)CC2)cc1] | 4-Amino-1-(2-chloro-benzyl)-piperidine-4-carboxylic acid (4-ethyl-phenyl)-amide 372.2 | [4-(4-Ethyl-phenylcarbamoyl)-piperidin-4-yl]-carbamic acid tert-butyl ester and 1-Bromomethyl-2-chloro-benzene (commercially available) |
| 155 | 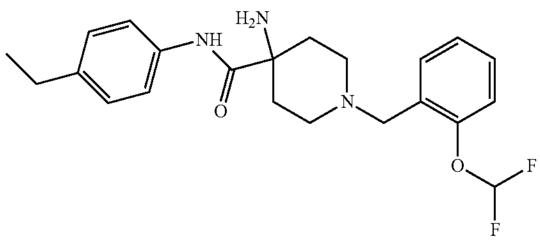 [SMILES: CCc1ccc(NC(=O)C2(N)CCN(Cc3ccccc3OC(F)F)CC2)cc1] | 4-Amino-1-(2-difluoromethoxy-benzyl)-piperidine-4-carboxylic acid (4-ethyl-phenyl)-amide 404.3 | [4-(4-Ethyl-phenylcarbamoyl)-piperidin-4-yl]-carbamic acid tert-butyl ester and 1-Bromomethyl-2-difluoromethoxy-benzene (commercially available) |
| 156 | 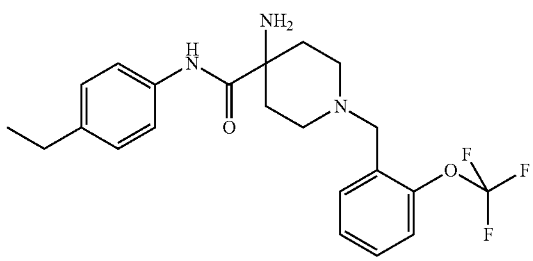 [SMILES: CCc1ccc(NC(=O)C2(N)CCN(Cc3ccccc3OC(F)(F)F)CC2)cc1] | 4-Amino-1-(2-trifluoromethoxy-benzyl)-piperidine-4-carboxylic acid (4-ethyl-phenyl)-amide 422.2 | [4-(4-Ethyl-phenylcarbamoyl)-piperidin-4-yl]-carbamic acid tert-butyl ester and 1-Bromomethyl-2-trifluoromethoxy-benzene (commercially available) |
| 157 | 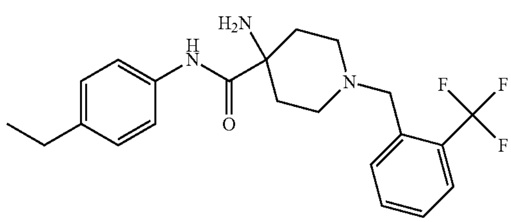 [SMILES: CCc1ccc(NC(=O)C2(N)CCN(Cc3ccccc3C(F)(F)F)CC2)cc1] | 4-Amino-1-(2-trifluoromethyl-benzyl)-piperidine-4-carboxylic acid (4-ethyl-phenyl)-amide 406.4 | [4-(4-Ethyl-phenylcarbamoyl)-piperidin-4-yl]-carbamic acid tert-butyl ester and 1-Bromomethyl-2-trifluoromethyl-benzene (commercially available) |
| 158 | 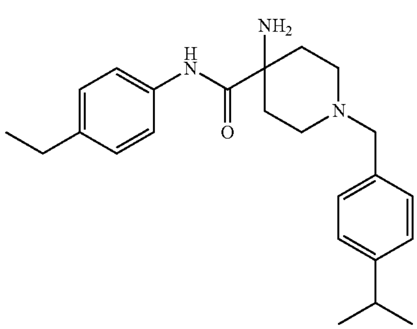 [SMILES: CCc1ccc(NC(=O)C2(N)CCN(Cc3ccc(C(C)C)cc3)CC2)cc1] | 4-Amino-1-(4-isopropyl-benzyl)-piperidine-4-carboxylic acid (4-ethyl-phenyl)-amide 380.5 | [4-(4-Ethyl-phenylcarbamoyl)-piperidin-4-yl]-carbamic acid tert-butyl ester and 1-Bromomethyl-4-isopropyl-benzene (commercially available) |

TABLE 4-continued

| Ex | Structure | Chemical Name | Starting material |
|---|---|---|---|
| 159 | 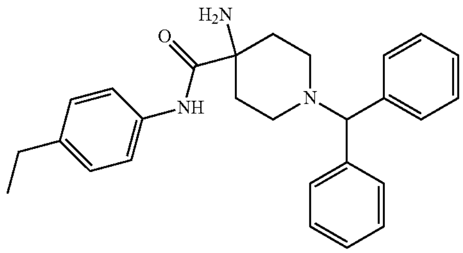 [SMILES: CCc1ccc(NC(=O)C2(N)CCN(C(c3ccccc3)c3ccccc3)CC2)cc1] | 4-Amino-1-benzhydryl-piperidine-4-carboxylic acid (4-ethyl-phenyl) amide 414.3 | [4-(4-Ethyl-phenylcarbamoyl)-piperidin-4-yl]-carbamic acid tert-butyl ester and bromodiphenylmethane (commercially available) |

Example 160

4-Methylamino-1-(toluene-4-sulfonyl)-piperidine-4-carboxylic acid (4-trifluoromethoxy-phenyl)-amide

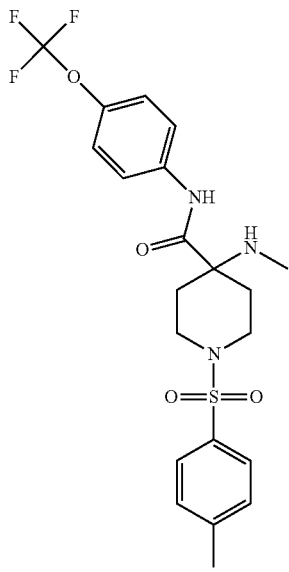 [SMILES: CNC1(C(=O)Nc2ccc(OC(F)(F)F)cc2)CCN(S(=O)(=O)c2ccc(C)cc2)CC1]

A mixture of 42 mg (0.08 mmol) 4-Amino-1-(toluene-4-sulfonyl)-piperidine-4-carboxylic acid (4-trifluoromethoxy-phenyl)-amide; hydrochloride (example 80) and 96 mg (0.68 mmol) methyl iodide and 17.6 mg (0.128 mmol) potassium carbonate in 2 mL DMF was heated to 40° C. for 1.5 h. The mixture was filtered and the filtrate was subjected to purification by preparative HPLC on reversed phase eluting with a gradient formed from acetonitrile, water and NEt$_3$ to yield after evaporation of the product containing fractions 9.6 mg (24%) of the title compound. MS (m/e): 472.3 [(M+H)$^+$].

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |

-continued

|  | Per tablet |
|---|---|
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound according to formula (I),

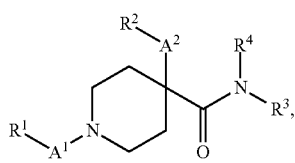

wherein

R$^1$ is selected from the group consisting of: alkyl, cycloalkyl, cycloalkyalkyl, haloalkyl, thiophenyl, substituted thiophenyl, phenyl, substituted phenyl, benzyloxy, substituted benzyloxy, pyridinyl, substituted pyridinyl, pyrimidyl and substituted pyrimidyl, wherein substituted thiophenyl, substituted phenyl, substituted benzyloxy, substituted pyridinyl and substituted pyrimidyl are substituted with one to three substituents independently selected from the group consisting of: alkyl, cycloalkyl, halogen, hydroxy, alkoxy, cycloalkylalkoxy, haloalkyl, haloalkoxy, alkylsulfonyl and cycloalkylsulfonyl;

R² is selected from the group consisting of: hydrogen, alkyl and cycloalkyl;

R³ is selected from the group consisting of: indanyl, substituted indanyl, pyridinyl, substituted pyridinyl, pyrimidyl, substituted pyrimidyl, phenyl and substituted phenyl, wherein substituted indanyl, substituted pyridinyl and substituted pyrimidyl are substituted with one to three substituents independently selected from the group consisting of: alkyl, cycloalkyl, halogen, hydroxy, alkoxy, cycloalkylalkoxy, haloalkyl, haloalkoxy and alkenyl, and wherein substituted phenyl is phenyl substituted with one substituent selected from the group consisting of: alkyl, cycloalkyl, halogen, hydroxy, alkoxy, cycloalkylalkoxy, haloalkyl, haloalkoxy and alkenyl;

R⁴ is selected from the group consisting of: hydrogen, alkyl and cycloalkyl;

one of R⁵ and R⁶ is selected from the group consisting of: hydrogen, alkyl and cycloalkyl, and the other one is selected from the group consisting of: hydrogen, alkyl, cycloalkyl, phenyl and substituted phenyl, wherein substituted phenyl is phenyl substituted with one to three substituents independently selected from the group consisting of: alkyl, cycloalkyl, halogen, hydroxy, alkoxy, cycloalkylalkoxy, haloalkyl, haloalkoxy, alkylsulfonyl and cycloalkylsulfonyl;

R⁷ is selected from the group consisting of: hydrogen, alkyl and cycloalkyl, wherein, when R¹ is benzyloxy, both R² and R⁷ are hydrogen;

A¹ is —S(O)₂—; and

A² is —O— or —NR⁷—;

or a pharmaceutically acceptable salt thereof.

2. A compound according to claim 1, wherein R¹ is substituted phenyl, wherein said phenyl is substituted with one to three substituents independently selected from the group consisting of: alkyl, halogen and haloalkoxy.

3. A compound according to claim 1, wherein R¹ is selected from the group consisting of: 2-methylphenyl, 2-chlorophenyl, 2-fluorophenyl and 2-trifluoromethoxyphenyl.

4. A compound according to claim 1, wherein R³ is substituted phenyl, wherein said phenyl is substituted with one substituent selected from the group consisting of alkyl, halogen, alkoxy, haloalkoxy and alkenyl.

5. A compound according to claim 1, wherein R³ is substituted phenyl, wherein said phenyl is substituted in the 4-position with a substituent selected from the group consisting of alkyl, alkoxy and haloalkoxy.

6. A compound according to claim 1, wherein both R⁵ and R⁶ are hydrogen.

7. A compound according to claim 1, wherein A² is —NR⁷—.

8. A compound according to claim 1, selected from the group consisting of:
1-(2-Chloro-benzenesulfonyl)-4-hydroxy-piperidine-4-carboxylic acid (4-tert-butyl-phenyl)-amide;
4-Hydroxy-1-(toluene-2-sulfonyl)-piperidine-4-carboxylic acid (4-tert-butyl-phenyl)-amide;
1-(2-Chloro-benzyl)-4-hydroxy-piperidine-4-carboxylic acid methyl-(4-trifluoromethoxy-phenyl)-amide;
4-Amino-1-(toluene-4-sulfonyl)-piperidine-4-carboxylic acid (4-tert-butyl-phenyl)-amide;
4-Amino-1-(toluene-4-sulfonyl)-piperidine-4-carboxylic acid (4-tert-butyl-phenyl)-amide hydrochloride;
4-Amino-1-(toluene-4-sulfonyl)-piperidine-4-carboxylic acid (4-trifluoromethoxy-phenyl)-amide;
4-Amino-1-(toluene-4-sulfonyl)-piperidine-4-carboxylic acid (4-trifluoromethoxy-phenyl)-amide hydrochloride;
4-Amino-1-(2-chloro-benzenesulfonyl)-piperidine-4-carboxylic acid (4-ethyl-phenyl)-amide;
4-Amino-1-(2-chloro-benzenesulfonyl)-piperidine-4-carboxylic acid (4-isopropoxy-phenyl)-amide;
4-Amino-1-(2-chloro-benzenesulfonyl)-piperidine-4-carboxylic acid (4-trifluoromethoxy-phenyl)-amide;
4-Amino-1-(2-chloro-benzenesulfonyl)-piperidine-4-carboxylic acid (4-isopropyl-phenyl)-amide;
4-Amino-1-(2-chloro-benzenesulfonyl)-piperidine-4-carboxylic acid (4-isopropyl-phenyl)-amide hydrochloride;
4-Amino-1-(2-fluoro-benzenesulfonyl)-piperidine-4-carboxylic acid (4-isopropyl-phenyl)-amide; and
4-Amino-1-(2-trifluoromethoxy-benzenesulfonyl)-piperidine-4-carboxylic acid (4-ethyl-phenyl)-amide.

9. A pharmaceutical composition comprising a compound according to claim 1 and a therapeutically inert carrier.

10. A compound according to claim 1, selected from the group consisting of:
4-Hydroxy-1-(toluene-4-sulfonyl)-piperidine-4-carboxylic acid (4-isopropyl-phenyl)-amide;
1-(2-Chloro-benzenesulfonyl)-4-hydroxy-piperidine-4-carboxylic acid (4-isopropyl-phenyl)-amide;
4-Hydroxy-1-(4-methoxy-benzenesulfonyl)-piperidine-4-carboxylic acid (4-isopropyl-phenyl)-amide;
1-(2-Chloro-benzenesulfonyl)-4-hydroxy-piperidine-4-carboxylic acid (4-trifluoromethoxy-phenyl)-amide;
4-Hydroxy-1-(toluene-4-sulfonyl)-piperidine-4-carboxylic acid (4-isopropoxy-phenyl)-amide;
1-(2-Chloro-benzenesulfonyl)-4-hydroxy-piperidine-4-carboxylic acid (4-isopropoxy-phenyl)-amide;
4-Hydroxy-1-(toluene-4-sulfonyl)-piperidine-4-carboxylic acid (4-tert-butyl-phenyl)-amide;
1-(2-Chloro-benzenesulfonyl)-4-hydroxy-piperidine-4-carboxylic acid (4-tert-butyl-phenyl)-amide;
4-Hydroxy-1-(4-methoxy-benzenesulfonyl)-piperidine-4-carboxylic acid (4-tert-butyl-phenyl)-amide;
4-Hydroxy-1-(toluene-2-sulfonyl)-piperidine-4-carboxylic acid (4-tert-butyl-phenyl)-amide;
1-(2-Fluoro-benzenesulfonyl)-4-hydroxy-piperidine-4-carboxylic acid (4-tert-butyl-phenyl)-amide;
4-Hydroxy-1-(2-methoxy-benzenesulfonyl)-piperidine-4-carboxylic acid (4-tert-butyl-phenyl)-amide;
4-Hydroxy-1-(2-methanesulfonyl-benzenesulfonyl)-piperidine-4-carboxylic acid (4-tert-butyl-phenyl)-amide;
1-(4-Chloro-2-fluoro-benzenesulfonyl)-4-hydroxy-piperidine-4-carboxylic acid (4-tert-butyl-phenyl)-amide; and
1-(2,4-Difluoro-benzenesulfonyl)-4-hydroxy-piperidine-4-carboxylic acid (4-tert-butyl-phenyl)-amide.

11. A compound according to claim 1, selected from the group consisting of:
1-(2,4-Dimethoxy-benzenesulfonyl)-4-hydroxy-piperidine-4-carboxylic acid (4-tert-butyl-phenyl)-amide;
1-(4-Fluoro-2-methyl-benzenesulfonyl)-4-hydroxy-piperidine-4-carboxylic acid (4-tert-butyl-phenyl)-amide;
4-Hydroxy-1-(2-methoxy-5-methyl-benzenesulfonyl)-piperidine-4-carboxylic acid (4-tert-butyl-phenyl)-amide;
1-(2,5-Dimethoxy-benzenesulfonyl)-4-hydroxy-piperidine-4-carboxylic acid (4-tert-butyl-phenyl)-amide;
1-(2,5-Difluoro-benzenesulfonyl)-4-hydroxy-piperidine-4-carboxylic acid (4-tert-butyl-phenyl)-amide;
1-(2,5-Dimethyl-benzenesulfonyl)-4-hydroxy-piperidine-4-carboxylic acid (4-tert-butyl-phenyl)-amide;
1-(5-Fluoro-2-methyl-benzenesulfonyl)-4-hydroxy-piperidine-4-carboxylic acid (4-tert-butyl-phenyl)-amide;

1-(5-Fluoro-2-methoxy-benzenesulfonyl)-4-hydroxy-piperidine-4-carboxylic acid (4-tert-butyl-phenyl)-amide;

4-Hydroxy-1-(2-methyl-propane-1-sulfonyl)-piperidine-4-carboxylic acid (4-trifluoromethoxy-phenyl)-amide;

1-(2,2-Dimethyl-propane-1-sulfonyl)-4-hydroxy-piperidine-4-carboxylic acid (4-trifluoromethoxy-phenyl)-amide;

4-Hydroxy-1-(thiophene-2-sulfonyl)-piperidine-4-carboxylic acid (4-trifluoromethoxy-phenyl)-amide;

4-Hydroxy-1-(toluene-2-sulfonyl)-piperidine-4-carboxylic acid (4-trifluoromethoxy-phenyl)-amide;

4-Hydroxy-1-(toluene-4-sulfonyl)-piperidine-4-carboxylic acid (4-trifluoromethoxy-phenyl)-amide;

1-(2-Fluoro-benzenesulfonyl)-4-hydroxy-piperidine-4-carboxylic acid (4-trifluoromethoxy-phenyl)-amide; and 4-Hydroxy-1-(3,3,3-trifluoro-propane-1-sulfonyl)-piperidine-4-carboxylic acid (4-trifluoromethoxy-phenyl)-amide.

12. A compound according to claim 1, selected from the group consisting of:

4-Hydroxy-1-(2-trifluoromethyl-benzenesulfonyl)-piperidine-4-carboxylic acid (4-trifluoromethoxy-phenyl)-amide;

1-(2,2-Dimethyl-propane-1-sulfonyl)-4-hydroxy-piperidine-4-carboxylic acid methyl-(4-trifluoromethoxy-phenyl)-amide;

4-Hydroxy-1-(thiophene-2-sulfonyl)-piperidine-4-carboxylic acid methyl-(4-trifluoromethoxy-phenyl)-amide;

4-Hydroxy-1-(toluene-2-sulfonyl)-piperidine-4-carboxylic acid methyl-(4-trifluoromethoxy-phenyl)-amide;

4-Hydroxy-1-(toluene-4-sulfonyl)-piperidine-4-carboxylic acid methyl-(4-trifluoromethoxy-phenyl)-amide;

1-(2-Fluoro-benzenesulfonyl)-4-hydroxy-piperidine-4-carboxylic acid methyl-(4-trifluoromethoxy-phenyl)-amide;

1-(2-Chloro-benzenesulfonyl)-4-hydroxy-piperidine-4-carboxylic acid methyl-(4-trifluoromethoxy-phenyl)-amide;

4-Hydroxy-1-(2-trifluoromethyl-benzenesulfonyl)-piperidine-4-carboxylic acid methyl-(4-trifluoromethoxy-phenyl)-amide;

4-Hydroxy-1-(toluene-2-sulfonyl)-piperidine-4-carboxylic acid ethyl-(4-trifluoromethoxy-phenyl)-amide;

1-(2-Fluoro-benzenesulfonyl)-4-hydroxy-piperidine-4-carboxylic acid ethyl-(4-trifluoromethoxy-phenyl)-amide;

1-(2-Chloro-benzenesulfonyl)-4-methoxy-piperidine-4-carboxylic acid (4-tert-butyl-phenyl)-amide;

4-Amino-1-(toluene-4-sulfonyl)-piperidine-4-carboxylic acid (4-tert-butyl-phenyl)-amide;

4-Amino-1-(toluene-4-sulfonyl)-piperidine-4-carboxylic acid (4-tert-butyl-phenyl)-amide hydrochloride;

4-Amino-1-(toluene-4-sulfonyl)-piperidine-4-carboxylic acid (4-isopropyl-phenyl)-amide; and 4-Amino-1-(toluene-4-sulfonyl)-piperidine-4-carboxylic acid (4-isopropyl-phenyl)-amide hydrochloride.

13. A compound according to claim 1, selected from the group consisting of:

4-Amino-1-(toluene-4-sulfonyl)-piperidine-4-carboxylic acid (4-isopropoxy-phenyl)-amide;

4-Amino-1-(toluene-4-sulfonyl)-piperidine-4-carboxylic acid (4-isopropoxy-phenyl)-amide hydrochloride;

4-Amino-1-(toluene-4-sulfonyl)-piperidine-4-carboxylic acid (4-trifluoromethoxy-phenyl)-amide;

4-Amino-1-(toluene-4-sulfonyl)-piperidine-4-carboxylic acid (4-trifluoromethoxy-phenyl)-amide hydrochloride;

4-Amino-1-(toluene-4-sulfonyl)-piperidine-4-carboxylic acid (4-ethyl-phenyl)-amide;

4-Amino-1-(4-isopropyl-benzenesulfonyl)-piperidine-4-carboxylic acid (4-isopropyl-phenyl)-amide;

4-Amino-1-(4-isopropyl-benzenesulfonyl)-piperidine-4-carboxylic acid (4-isopropyl-phenyl)-amide hydrochloride;

4-Amino-1-(2-chloro-benzenesulfonyl)-piperidine-4-carboxylic acid (3-trifluoromethyl-phenyl)-amide;

4-Amino-1-(2-chloro-benzenesulfonyl)-piperidine-4-carboxylic acid (3-ethyl-phenyl)-amide;

4-Amino-1-(2-chloro-benzenesulfonyl)-piperidine-4-carboxylic acid (4-ethyl-phenyl)-amide;

4-Amino-1-(2-chloro-benzenesulfonyl)-piperidine-4-carboxylic acid (4-fluoro-phenyl)-amide;

4-Amino-1-(2-chloro-benzenesulfonyl)-piperidine-4-carboxylic acid (4-chloro-phenyl)-amide;

4-Amino-1-(2-chloro-benzenesulfonyl)-piperidine-4-carboxylic acid (4-isopropoxy-phenyl)-amide;

4-Amino-1-(2-chloro-benzenesulfonyl)-piperidine-4-carboxylic acid (4-difluoromethoxy-phenyl)-amide; and 4-Amino-1-(2-chloro-benzenesulfonyl)-piperidine-4-carboxylic acid (4-propyl-phenyl)-amide.

14. A compound according to claim 1, selected from the group consisting of:

4-Amino-1-(2-chloro-benzenesulfonyl)-piperidine-4-carboxylic acid indan-5-ylamide;

4-Amino-1-(2-chloro-benzenesulfonyl)-piperidine-4-carboxylic acid (4-vinyl-phenyl)-amide;

4-Amino-1-(2-chloro-benzenesulfonyl)-piperidine-4-carboxylic acid (6-isopropyl-pyridin-3-yl)-amide;

4-Amino-1-(2-chloro-benzenesulfonyl)-piperidine-4-carboxylic acid [4-(2,2,2-trifluoro-1,1-dimethyl-ethoxy)-phenyl]-amide;

4-Amino-1-(2-chloro-benzenesulfonyl)-piperidine-4-carboxylic acid (4-trifluoromethoxy-phenyl)-amide;

4-Amino-1-(2-chloro-benzenesulfonyl)-piperidine-4-carboxylic acid (4-butyl-phenyl)-amide;

4-Amino-1-(2-chloro-benzenesulfonyl)-piperidine-4-carboxylic acid [4-(2,2,2-trifluoro-ethoxy)-phenyl]-amide;

4-Amino-1-(2-chloro-benzenesulfonyl)-piperidine-4-carboxylic acid (4-isopropyl-phenyl)-amide;

4-Amino-1-(2-chloro-benzenesulfonyl)-piperidine-4-carboxylic acid (4-isopropyl-phenyl)-amide hydrochloride;

4-Amino-1-(3-chloro-benzenesulfonyl)-piperidine-4-carboxylic acid (4-isopropyl-phenyl)-amide;

4-Amino-1-(fluoro-benzenesulfonyl)-piperidine-4-carboxylic acid (4-isopropyl-phenyl)-amide;

4-Amino-1-(toluene-2-sulfonyl)-piperidine-4-carboxylic acid (4-isopropyl-phenyl)-amide;

4-Amino-1-(2-methyl-propane-1-sulfonyl)-piperidine-4-carboxylic acid (4-isopropyl-phenyl)-amide;

4-Amino-1-(2-methyl-propane-1-sulfonyl)-piperidine-4-carboxylic acid (4-isopropyl-phenyl)-amide hydrochloride; and 4-Amino-1-(2-chloro-4-trifluoromethyl-benzenesulfonyl)-piperidine-4-carboxylic acid (4-isopropyl-phenyl)-amide.

15. A compound according to claim 1, selected from the group consisting of:

4-Amino-1-benzenesulfonyl-piperidine-4-carboxylic acid (4-ethyl-phenyl)-amide;

4-Amino-1-(2-fluoro-benzenesulfonyl)-piperidine-4-carboxylic acid (4-ethyl-phenyl)-amide;

4-Amino-1-(toluene-2-sulfonyl)-piperidine-4-carboxylic acid (4-ethyl-phenyl)-amide;
4-Amino-1-(2-methanesulfonyl-benzenesulfonyl)-piperidine-4-carboxylic acid (4-ethyl-phenyl)-amide;
4-Amino-1-(2-methoxy-benzenesulfonyl)-piperidine-4-carboxylic acid (4-ethyl-phenyl)-amide;
4-Amino-1-(4-trifluoromethoxy-benzenesulfonyl)-piperidine-4-carboxylic acid (4-ethyl-phenyl)-amide;
4-Amino-1-(4-methoxy-benzenesulfonyl)-piperidine-4-carboxylic acid (4-ethyl-phenyl)-amide;
4-Amino-1-(4-ethyl-benzenesulfonyl)-piperidine-4-carboxylic acid (4-ethyl-phenyl)-amide;
4-Amino-1-(4-butyl-benzenesulfonyl)-piperidine-4-carboxylic acid (4-ethyl-phenyl)-amide;
4-Amino-1-(2,6-difluoro-benzenesulfonyl)-piperidine-4-carboxylic acid (4-ethyl-phenyl)-amide;
4-Amino-1-(butane-1-sulfonyl)-piperidine-4-carboxylic acid (4-ethyl-phenyl)-amide;
4-Amino-1-cyclohexylmethanesulfonyl-piperidine-4-carboxylic acid (4-ethyl-phenyl)-amide;
4-Amino-1-(2-trifluoromethyl-benzenesulfonyl)-piperidine-4-carboxylic acid (4-ethyl-phenyl)-amide;
4-Amino-1-(2-chloro-4-fluoro-benzenesulfonyl)-piperidine-4-carboxylic acid (4-ethyl-phenyl)-amide; and
4-Amino-1-(2-chloro-4-trifluoromethyl-benzenesulfonyl)-piperidine-4-carboxylic acid (4-ethyl-phenyl)-amide.

16. A compound according to claim 1, selected from the group consisting of:
4-Amino-1-(6-chloro-pyridine-3-sulfonyl)-piperidine-4-carboxylic acid (4-ethyl-phenyl)-amide;
4-Amino-1-(2-trifluoromethoxy-benzenesulfonyl)-piperidine-4-carboxylic acid (4-ethyl-phenyl)-amide;
4-Amino-1-(2,6-dichloro-benzenesulfonyl)-piperidine-4-carboxylic acid (4-ethyl-phenyl)-amide; and
4-Methylamino-1-(toluene-4-sulfonyl)-piperidine-4-carboxylic acid (4-trifluoromethoxy-phenyl)-amide.

* * * * *